US012595512B2

(12) United States Patent
Dickerson et al.

(10) Patent No.: US 12,595,512 B2
(45) Date of Patent: *Apr. 7, 2026

(54) METHODS OF TREATING PSORIASIS

(71) Applicant: MiNDERA Corporation, Vista, CA (US)

(72) Inventors: Tobin Dickerson, San Marcos, CA (US); Bradford Taft, San Francisco, CA (US); Byung-In Lee, Encinitas, CA (US)

(73) Assignee: MiNDERA Corporation, Vista, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/812,678

(22) Filed: Aug. 22, 2024

(65) Prior Publication Data

US 2026/0055462 A1     Feb. 26, 2026

Related U.S. Application Data

(63) Continuation of application No. 18/812,671, filed on Aug. 22, 2024, which is a continuation of application No. 18/317,841, filed on May 15, 2023, now abandoned, which is a continuation of application No. PCT/US2021/061033, filed on Nov. 29, 2021.

(60) Provisional application No. 63/119,511, filed on Nov. 30, 2020.

(51) Int. Cl.
*C12Q 1/6883* (2018.01)
*C12Q 1/6869* (2018.01)

(52) U.S. Cl.
CPC ......... *C12Q 1/6883* (2013.01); *C12Q 1/6869* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,683,202 A | 7/1987 | Mullis |
| 6,293,925 B1 | 9/2001 | Safabash et al. |
| 6,503,231 B1 | 1/2003 | Prausnitz et al. |
| 6,663,820 B2 | 12/2003 | Arias et al. |
| 6,743,211 B1 | 6/2004 | Prausnitz et al. |
| 6,749,575 B2 | 6/2004 | Matriano et al. |
| 6,855,131 B2 | 2/2005 | Trautman et al. |
| 6,881,203 B2 | 4/2005 | Delmore et al. |
| 7,332,197 B2 | 2/2008 | Wood et al. |

| | | | |
|---|---|---|---|
| 7,416,541 B2 | 8/2008 | Yuzhakov et al. |
| 9,387,000 B2 | 7/2016 | Corrie et al. |
| 9,540,684 B2 | 1/2017 | Mahmood et al. |
| 10,995,366 B2 | 5/2021 | Mahmood et al. |
| 2002/0032415 A1 | 3/2002 | Trautman et al. |
| 2002/0087182 A1 | 7/2002 | Trautman et al. |
| 2002/0110828 A1 | 8/2002 | Ferea et al. |
| 2003/0027154 A1 | 2/2003 | Narahara et al. |
| 2003/0036710 A1 | 2/2003 | Matriano et al. |
| 2003/0211528 A1 | 11/2003 | Iscove |
| 2004/0146611 A1 | 7/2004 | Arias et al. |
| 2004/0181203 A1 | 9/2004 | Cormier et al. |
| 2005/0178760 A1 | 8/2005 | Chang et al. |
| 2006/0134661 A1 | 6/2006 | Essner |
| 2007/0023386 A1 | 2/2007 | Kravitz et al. |
| 2007/0148654 A1 | 6/2007 | Nakagawa |
| 2007/0148690 A1 | 6/2007 | Shao et al. |
| 2008/0039339 A1 | 2/2008 | Hassibi et al. |
| 2008/0039805 A1 | 2/2008 | Frederickson et al. |
| 2008/0108958 A1 | 5/2008 | Carter et al. |
| 2009/0062752 A1 | 3/2009 | Gonnelli |
| 2010/0003189 A1 | 1/2010 | Tlsty et al. |
| 2010/0106105 A1 | 4/2010 | Yeshurun et al. |
| 2010/0120627 A1 | 5/2010 | Belouchi et al. |
| 2010/0178651 A1 | 7/2010 | Hatzis et al. |
| 2010/0185142 A1 | 7/2010 | Kamen et al. |
| 2010/0286290 A1 | 11/2010 | Lohmann et al. |
| 2011/0028905 A1 | 2/2011 | Takada |
| 2011/0160069 A1 | 6/2011 | Corrie et al. |
| 2011/0191874 A1 | 8/2011 | Carlock et al. |
| 2011/0270221 A1 | 11/2011 | Ross |

(Continued)

FOREIGN PATENT DOCUMENTS

| | | |
|---|---|---|
| AU | 2012213965 A1 | 9/2012 |
| CN | 1688693 A | 10/2005 |

(Continued)

OTHER PUBLICATIONS

Arenkov, Pavel, et al., Protein Microchips: Use for Immunoassay and Enzymatic Reactions. Analytical Biochemistry 278(2):123-131 (2000).

(Continued)

*Primary Examiner* — Carla J Myers

(74) *Attorney, Agent, or Firm* — WILSON SONSINI GOODRICH & ROSATI

(57)     ABSTRACT

The present disclosure provides methods of treating psoriasis. The present disclosure provides methods of using a microneedle device in aid of treating a subject. The present disclosure also provides methods of treating a subject with psoriasis with a microneedle device. The present disclosure provides microneedle devices and kits for extracting biomarkers from a tissue. The present disclosure provides methods selecting a treatment for an autoimmune disease. The present disclosure also provides methods of nucleic acid analysis to prospectively predict a patient's response to a therapeutic.

19 Claims, 16 Drawing Sheets

(56) References Cited

U.S. PATENT DOCUMENTS

| | | | |
|---|---|---|---|
| 2011/0270223 A1 | 11/2011 | Sullivan et al. | |
| 2011/0288389 A9 | 11/2011 | Levinson et al. | |
| 2011/0294996 A1 | 12/2011 | Scheiber et al. | |
| 2011/0295149 A1 | 12/2011 | Mitragotri et al. | |
| 2012/0034598 A1 | 2/2012 | Holmes et al. | |
| 2012/0109613 A1 | 5/2012 | Boyden et al. | |
| 2012/0172820 A1 | 7/2012 | Cannehan et al. | |
| 2014/0066318 A1 | 3/2014 | Frisen et al. | |
| 2014/0287942 A1 | 9/2014 | Mahmood et al. | |
| 2017/0050010 A1 | 2/2017 | Mcallister et al. | |
| 2017/0145489 A1 | 5/2017 | Mahmood et al. | |
| 2018/0001071 A1 | 1/2018 | Simmers | |
| 2019/0184366 A1 | 6/2019 | Henderson | |
| 2019/0284270 A1 | 9/2019 | Johnson et al. | |
| 2019/0367984 A1 | 12/2019 | Wright et al. | |
| 2019/0388473 A1 | 12/2019 | Mata-Fink et al. | |
| 2020/0063188 A1 | 2/2020 | Howell et al. | |
| 2021/0317513 A1 | 10/2021 | Mahmood et al. | |
| 2023/0383352 A1 | 11/2023 | Dickerson et al. | |
| 2024/0425926 A1 | 12/2024 | Dickerson et al. | |

FOREIGN PATENT DOCUMENTS

| | | |
|---|---|---|
| CN | 101370946 A | 2/2009 |
| EP | 2119469 A1 | 11/2009 |
| JP | 2012526087 A | 10/2012 |
| JP | 2018183146 A | 11/2018 |
| WO | WO-0022108 A1 | 4/2000 |
| WO | WO-0175447 A1 | 10/2001 |
| WO | WO-0212891 A1 | 2/2002 |
| WO | WO-2007048074 A1 | 4/2007 |
| WO | WO-2008073629 A2 | 6/2008 |
| WO | WO-2008108004 A1 | 9/2008 |
| WO | WO-2009140735 A1 | 11/2009 |
| WO | WO-2010128158 A1 | 11/2010 |
| WO | WO-2012074085 A1 | 6/2012 |
| WO | WO-2014093934 A1 | 6/2014 |
| WO | WO-2017049035 A1 | 3/2017 |
| WO | WO-2017112536 A1 | 6/2017 |
| WO | WO-2021067667 A1 | 4/2021 |
| WO | WO-2022115383 A1 | 6/2022 |
| WO | WO-2022115714 A1 | 6/2022 |

OTHER PUBLICATIONS

Aryani, Arian, et al., In Vitro application of fibonucleases: comparison of the effects on mRNA and miRNA stability. BMC Research Notes 8(164):1-9 (2015).

Bagel, Jerry, et al., A Machine Learning-Based Test for Predicting Response to Psoriasis Biologics. SKIN The Journal of Cutaneous Medicine 5(6):621-638 (2021).

Chen, Lin-Chi, et al., Analysis of GD2/GM2 Synthase mRNA as a biomarker for small cell lung cancer. Lung Cancer 67(2):216-220 (2010).

Coleman, Robert A., Of Mouse and Man—what Is The Value of The Mouse In Predicting Gene Expression In Humans?. Drug Discovery Today 8(6):233-235 (2003).

Da Rosa, Joel Correa, et al., Shrinking the Psoriasis Assessment Gap: Early Gene-Expression Profiling Accurately Predicts Response to Long-Term Treatment. Journal of Investigative Dermatology 137(2):305-312 (2017).

Day, Philip J, et al., Immobilization of Polynucleotides on Magnetic Particles. Factors Influencing Hybridization Efficiency. Biochemical Journal 278(Pt 3):735-740 (1991).

De Souza, Marilesia Ferreira, et al., Circulating mRNAs and miRNAs as candidate markers for the diagnosis and prognosis of prostate cancer. PLoS ONE 12(9):e0184094, 16 Pages (2017).

Devor, Eric J, et al., Strategies for Attaching Oligonucleotides to Solid Supports. Integrated DNA Technologies :1-24 (2005).

Eckert, Kristin A, et al., DNA Polymerase Fidelity and The Polymerase Chain Reaction. PCR Methods and Applications 1(1):17-24 (1991).

Fodor, Stephen P, et al., Light-Directed, Spatially Addressable Parallel Chemical Synthesis. Science 251(4995):767-773 (1991).

Gonzalo, Victoria, et al., Telomerase mRNA Expression and Immunohistochemical Detection as a Biomarker of Malignant Transformation In Patients With Inflammatory Bowel Disease. Gastroenterology Hepatology 33(4):288-296 (2010).

Goto, Yasufumi, et al., High Molecular Weight-melanoma-associated Antigen as a Biomarker of Desmoplastic Melanoma. Pigment Cell & Melanoma Research 23(1):137-140 (2010).

Guatelli, John C. et al. Isothermal, In Vitro Amplification of Nucleic Acids by a Multienzyme Reaction Modeled After Retroviral Replication. PNAS USA 87(5):1874-1878.

Guo, Zhen, et al., Direct Fluorescence Analysis of Genetic Polymorphisms by Hybridization With Oligonucleotide Arrays on Glass Supports. Nucleic Acids Research 22(24):5456-5465 (1994).

Hojfeldt, Jonas W, et al., A Cleavable Amino-Thiol Linker for Reversible Linking of Amines to DNA. The Journal of Organic Chemistry 71(25):9556-9569 (2006).

Ibrahim, Sherrif F, et al., LB968 Non-Invasive Skin Transcriptome Extraction Using MiNDERA Microneedle Technology. Journal of Investigative Dermatology 137(10):1 Page (2017).

Jacobs, Ian J, et al., Screening for Ovarian Cancer: A Pilot Randomised Controlled Trial. The Lancet 353(9160):1207-1210 (1999).

Jansen, Patrick A M, et al., β-Defensin-2 Protein Is a Serum Biomarker for Disease Activity in Psoriasis and Reaches Biologically Relevant Concentrations in Lesional Skin. PLoS ONE 4(3):e4725, 9 Pages (2009).

Japanese Patent Application No. 2019-162715 Office Action dated Jul. 12, 2021.

Jin, Chun Yan, et al., Mass Producible and Biocompatible Microneedle Patch and Functional Verification of Its Usefulness for Transdermal Drug Delivery. Biomed Microdevices 11(6):1195-1203 (2009).

Johnson, Timothy V, et al., C-Reactive Protein as a Clinically Useful Biomarker of Metastasis of Renal Cell Carcinoma. Molecular Diagnosis & Therapy 14(3):191-193 (2010).

Jung, Monika, et al., Robust MicroRNA Stability In Degraded RNA Preparations From Human Tissue and Cell Samples. Clinical Chemistry 56(6):998-1006 (2010).

Kondkar, Altaf A, et al., Utility of Circulating microRNAs as Clinical Biomarkers for Cardiovascular Diseases. BioMed Research International 2015(821823):10 Pages (2015).

Kunz, M, et al., DNA Microarray Technology and Its Applications In Dermatology. Experimental Dermatology 13(10):593-606 (2004).

Kwoh, D Y, et al., Transcription-based amplification system and detection of amplified human immunodeficiency virus type 1 with a bead-based sandwich hybridization format. Proceedings of the National Academy of Sciences of the United States of America 86(4):1173-1177 (1989).

Lamture, J B, et al., Direct Detection of Nucleic Acid Hybridization on The Surface of a Charge Coupled Device. Nucleic Acids Research 22(11):2121-2125 (1994).

Landegren, U, et al., A Ligase-mediated Gene Detection Technique. Science 241(4869):1077-1080 (1988).

Li, Shengjin, et al., Insulin-Like Growth Factor II mRNA-Binding Protein 3: A Novel Prognostic Biomarker for Oral Squamous Cell Carcinoma. Head Neck 33(3):368-374 (2011).

Liu, Chang-Gong, et al., MicroRNA Expression Profiling Using Microarrays. Nature Protocols 3(4):563-578 (2008).

Liu, Ying, et al., A Genome-Wide Association Study of Psoriasis and Psoriatic Arthritis Identifies New Disease Loci. PLOS Genetics 4(3):e1000041, 14 Pages (2008).

Liu, Zheng, et al., Comparison of Differentially Expressed Genes In T Lymphocytes Between Human Autoimmune Disease and Murine Models of Autoimmune Disease. Clinical Immunology 112(3):225-230 (2004).

Lu, Bin, et al., Oriented Immobilization of Fab' Fragments on Silica Surfaces. Analytical Chemistry 67(1):83-87 (1995).

Macbeath, G, et al., Printing Proteins as Microarrays for High-Throughput Function Determination. Science 289:1760-1763 (2000).

Mathelin, Carole, et al., Serum Biomarkers for Detection of Breast Cancers: A Prospective Study. Breast Cancer Research and Treatment 96(1):83-90 (2006).

(56) References Cited

OTHER PUBLICATIONS

Mattila, P, et al., Fidelity of DNA Synthesis by The Thermococcus Litoralis DNA Polymerase—an Extremely Heat Stable Enzyme With Proofreading Activity. Nucleic Acids Research 19(18):4967-4973 (1991).

Mendoza, L G, et al., High-Throughput Microarray-BasedEnzyme-Linked Immunosorbent Assay (ELISA). BioTechniques 27(4):778-788 (1999).

Minoura, Kaho, et al., MicroRNA Profiling Is More Stable Than Messenger RNA Against RNA Degradation. Cellular and Molecular Biology 68(9):2 Pages (2008).

Miura, Norimasa, et al., Clinical Impact of Serum Transforming Growth Factor-alpha mRNA as a Predictive Biomarker for The Prognosis of Fulminant Hepatitis. Hepatology International 2(2):213-221 (2008).

Miura, Norimasa, et al., Serum Human Telomerase Reverse Transcriptase Messenger RNA as a Novel Tumor Marker for Hepatocellular Carcinoma. Clinical Cancer Research 11(9):3205-3209 (2005).

Nakanishi, K, et al., A Novel Method of Immobilizing Antibodies on a Quartz Crystal Microbalance Using Plasma-polymerized Films for Immunosensors. Analytical Chemistry 68(10):1695-1700 (1996).

Ng, Enders K O, et al., Presence of Filterable and Nonfilterable mRNA in the Plasma of Cancer Patients and Healthy Individuals. Clinical Chemistry 48(8):1212-1217 (2002).

Oh, Jae-Ho, et al., Influence of The Delivery Systems Using a Microneedle Array on The Permeation of a Hydrophilic Molecule, Calcein. European Journal of Pharmaceutics and Biopharmaceutics 69(3):1040-1045 (2008).

Paige, Jeremy S, et al., RNA Mimics of Green Fluorescent Protein. Science 333(6042):642-646 (2011).

PCT/US2013/075187 International Search Report and Written Opinion dated May 9, 2014.

PCT/US2021/061033 International Search Report and Written Opinion dated Apr. 6, 2022.

PCT/US2021/061033 Invitation to Pay Additional Fees dated Jan. 13, 2022.

Polascik, T J, et al., Prostate Specific Antigen: A Decade of Discovery—what We Have Learned and Where We are Going. Journal of Urology 162(2):293-306 (1999).

Pos, Ondrej, et al., Circulating Cell-free Nucleic Acids: Characteristics and Applications. European Journal of Human Genetics 26(7):937-945 (2018).

Quan, et al., Development of Microneedle Array as Cosmetic and Medical Device. Production and Technology. 64(2):63-68 (2012).

Rowe, C A, et al., An Array Immunosensor for Simultaneous Detection of Clinical Analytes. Analytical Chemistry 15;71(2):433-439 (1999).

Sakamoto, Yuichi, et al., WT1 mRNA Level In Peripheral Blood Is a Sensitive Biomarker for Monitoring Minimal Residual Disease In Acute Myeloid Leukemia. The Tohoku Journal of Experimental Medicine 219(2):169-176 (2009).

Sato, Akemi, et al., Establishment of a New Method, Transcription-reverse Transcription Concerted Reaction, for Detection of Plasma hnRNP B1 mRNA, A Biomarker of Lung Cancer. Journal of Cancer Research and Clinical Oncology 134(11):1191-1197 (2008).

Schena, M, et al., Quantitative Monitoring of Gene Expression Patterns With a Complementary DNA Microarray. Science 270(5235):467-470 (1995).

Shaheen, Safa, et al., Differential Expression and Pathway Analysis in Drug-Resistant Triple-Negative Breast Cancer Cell Lines Using RNASeq Analysis. International Journal of Molecular Sciences 19(6):13 Pages (2018).

Sulaiman, Dana Al, et al., Hydrogel-Coated Microneedle Arrays for Minimally Invasive Sampling and Sensing of Specific Circulating Nucleic Acids from Skin Interstitial Fluid. ACS Nano 13(8):9620-9628 (2019).

Tang, Fuchou, et al., mRNA-Seq Whole-Transcriptome Analysis of a Single Cell. Nature Methods 6(5):377-382 (2009).

Tomalin, Lewis E, et al., Short-Term Transcriptional Response to IL-17 Receptor—a Antagonism In The Treatment of Psoriasis. The Journal of Allergy and Clinical Immunology 145(3):922-932 (2020).

Tyagi, S, et al., Molecular Beacons: Probes that Fluoresce Upon Hybridization. Nature Biotechnology 14(3):303-308 (1996).

U.S. Appl. No. 14/106,661 Notice of Allowance dated Oct. 20, 2016.

U.S. Appl. No. 14/106,661 Office Action dated Dec. 22, 2015.

U.S. Appl. No. 14/106,661 Office Action dated Jul. 30, 2015.

U.S. Appl. No. 14/106,661 Office Action dated Sep. 8, 2016.

U.S. Appl. No. 15/367,015 Notice of Allowance dated Jan. 15, 2021.

U.S. Appl. No. 15/367,015 Office Action dated Apr. 2, 2020.

U.S. Appl. No. 15/367,015 Office Action dated Apr. 21, 2017.

U.S. Appl. No. 15/367,015 Office Action dated Apr. 25, 2019.

U.S. Appl. No. 15/367,015 Office Action dated Aug. 10, 2018.

U.S. Appl. No. 15/367,015 Office Action dated Jan. 22, 2018.

U.S. Appl. No. 15/367,015 Office Action dated Oct. 29, 2020.

U.S. Appl. No. 15/367,015 Office Action dated Oct. 3, 2019.

U.S. Appl. No. 18/317,841 Office Action dated Feb. 22, 2024.

Valladares-Ayerbes, Manuel, et al., Evaluation of Plakophilin-3 mRNA as a Biomarker for Detection of Circulating Tumor Cells In Gastrointestinal Cancer Patients. Cancer Epidemiology, Biomarkers & Prevention 19(6):1432-1440 (2010).

Van Ham, S Marieke, et al., Urinary Granzyme a mRNA Is a Biomarker to Diagnose Subclinical and Acute Cellular Rejection In Kidney Transplant Recipients. Kidney International 78(10):1033-1040 (2010).

Vijayendran, R A, et al., A Quantitative Assessment of Heterogeneity for Surface-Immobilized Proteins. Analytical Chemistry 73(3):471-480 (2001).

Visvanathan, Sudha, et al., Psoriatic Skin Molecular and Histopathologic Profiles After Treatment With Risankizumab Versus Ustekinumab. The Journal of Allergy and Clinical Immunology 143(6):2158-2169 (2019).

Wang, Hong, et al., Label-free Hybridization Detection of a Single Nucleotide Mismatch by Immobilization of Molecular Beacons on an Agarose Film. Nucleic Acids Research 30(12):1-9 (2002).

Wetmur, J G., DNA Probes: Applications of The Principles of Nucleic Acid Hybridization. Critical Reviews in Biochemistry and Molecular Biology 26(3-4):227-259 (1991).

Wu, D Y, et al., The Ligation Amplification Reaction (LAR)—amplification of Specific DNA Sequences Using Sequential Rounds of Template-dependent Ligation. Genomics 4(4):560-569 (1989).

Wu, Peng, et al., Diagnostic Devices as Biomaterials: A Review of Nucleic Acid and Protein Microarray Surface Performance Issues. Journal of Biomaterials Science, Polymer Edition 19(6):725-753 (2008).

Yamada, H, et al., Lymphocyte Metallothionein-mRNA as a Sensitive Biomarker of Cadmium Exposure. Industrial Health 39(1):29-32 (2001).

Young Jyoung, JY, et al., Immunosensor for The Detection of Vibrio Cholerae O1 Using Surface Plasmon Resonance. Biosensors and Bioelectronics 21(12):2315-2319 (2006).

Zhu, H, et al., Analysis of Yeast Protein Kinases Using Protein Chips. Nature Genetics 26(3):283-289 (2000).

Co-pending U.S. Appl. No. 19/326,553, inventors Mahmood; Tahir A. et al., filed on Sep. 11, 2025.

U.S. Appl. No. 17/175,606 Office Action dated Jul. 24, 2024.

U.S. Appl. No. 18/812,671 Office Action dated Jun. 26, 2025.

U.S. Appl. No. 18/812,671 Restriction Requirement dated Oct. 24, 2024.

JP2023-533232 Notice for Reasons for Refusal dated Nov. 28, 2026.

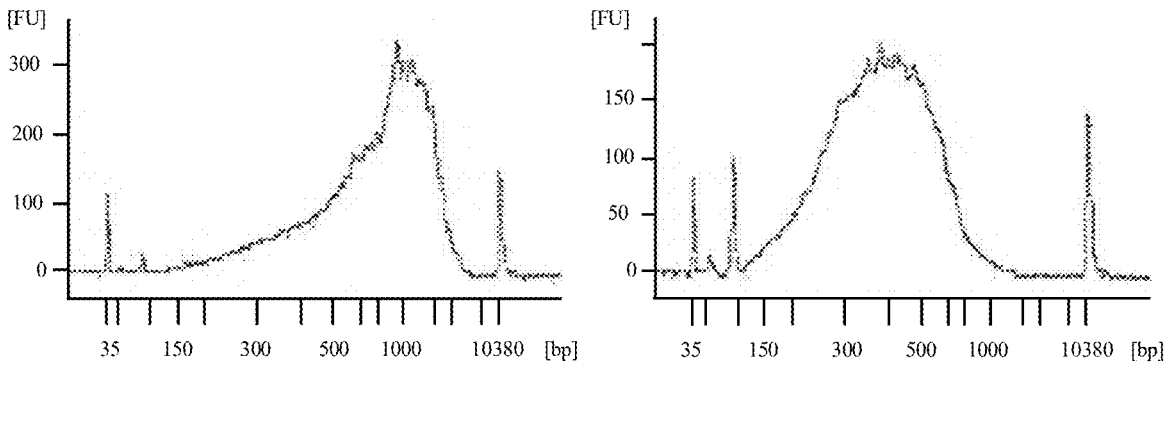
FIG. 5A                    FIG. 5B
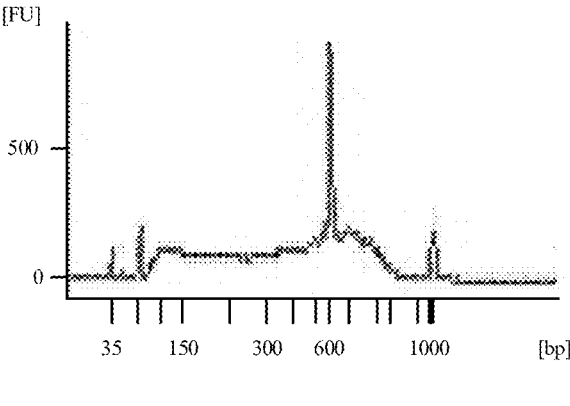
FIG. 5C

600

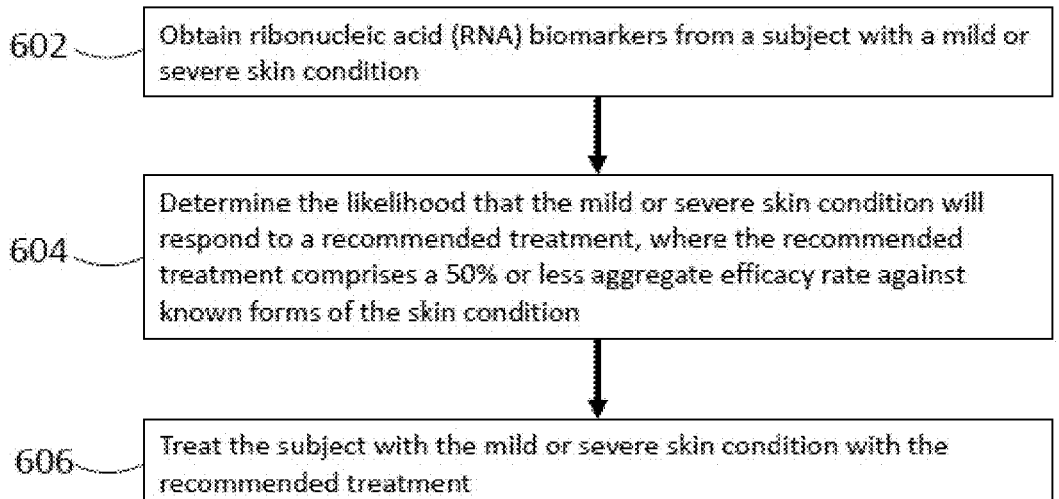

602 — Obtain ribonucleic acid (RNA) biomarkers from a subject with a mild or severe skin condition 604 — Determine the likelihood that the mild or severe skin condition will respond to a recommended treatment, where the recommended treatment comprises a 50% or less aggregate efficacy rate against known forms of the skin condition 606 — Treat the subject with the mild or severe skin condition with the recommended treatment

FIG. 6A

608

610 ─── Contact the skin of a subject with a microneedle device, where the microneedle device comprises one or more nucleic acid probes coupled to a microneedle 612 ─── Apply pressure to the microneedle device such that the microneedle device penetrates the skin of the subject 614 ─── Obtain extracted ribonucleic acid (RNA) molecules from the subject by removing the microneedle device from the skin of the subject 616 ─── Perform high throughput sequencing on the extracted RNA molecules to generate one or more sequence reads for the subject 618 ─── Align the one or more sequence reads for the subject with a known signature of sequence reads, where the known signature of sequence reads is associated with a positive response to the one or more therapeutic drugs, thereby obtaining aligned sequence reads 620 ─── Classify the subject as having a likelihood of positively responding to the one or more therapeutic drugs by applying a trained algorithm to the aligned sequence reads, wherein the trained algorithm has a greater than 70% positive predictive value, a greater than 75% positive predictive value, a greater than 80% positive predictive value, a greater than 85% positive predictive value, a greater than 90% positive predictive value, or a greater than 95% positive predictive value

FIG. 6B

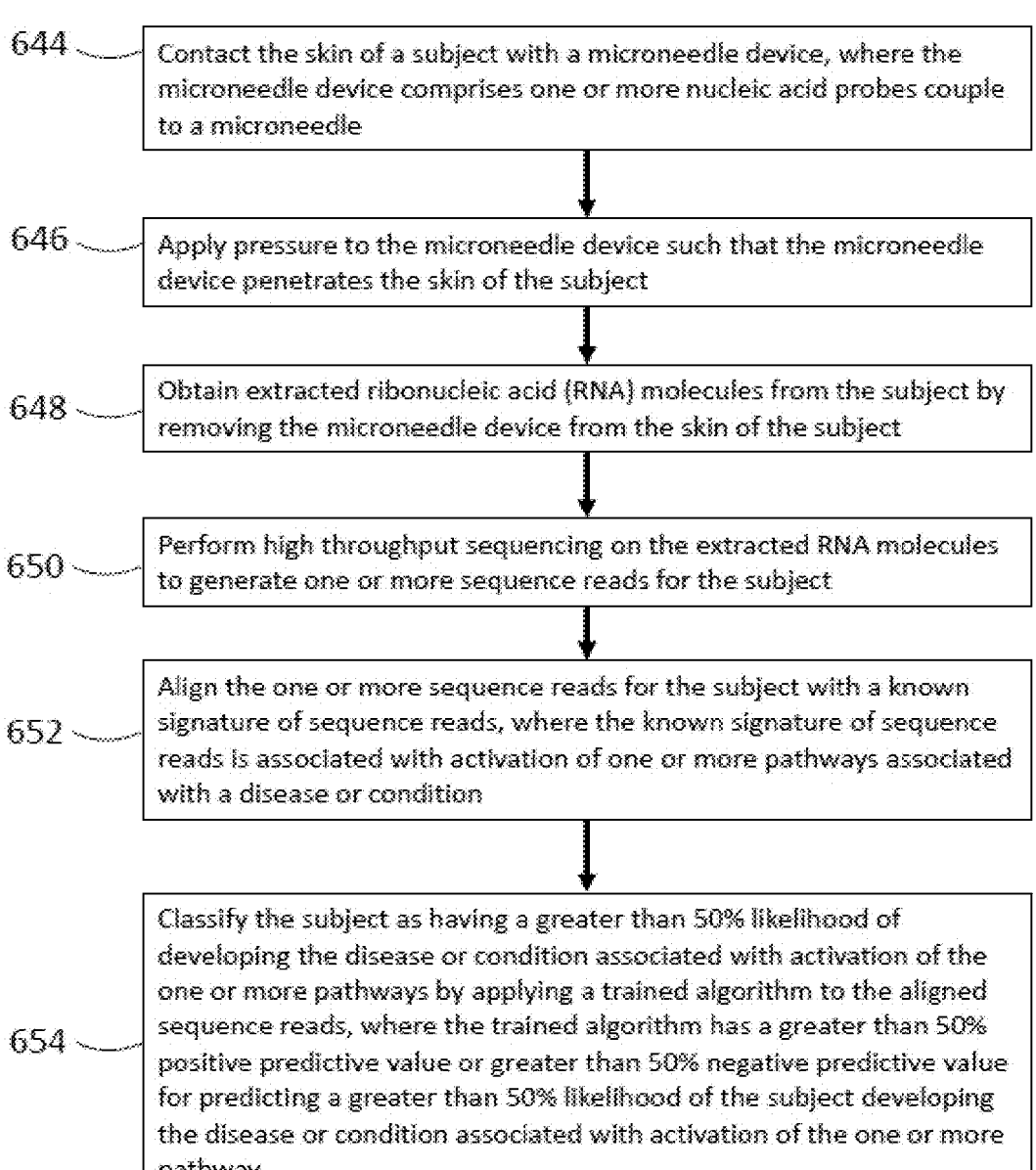

642

644 — Contact the skin of a subject with a microneedle device, where the microneedle device comprises one or more nucleic acid probes couple to a microneedle 646 — Apply pressure to the microneedle device such that the microneedle device penetrates the skin of the subject 648 — Obtain extracted ribonucleic acid (RNA) molecules from the subject by removing the microneedle device from the skin of the subject 650 — Perform high throughput sequencing on the extracted RNA molecules to generate one or more sequence reads for the subject 652 — Align the one or more sequence reads for the subject with a known signature of sequence reads, where the known signature of sequence reads is associated with activation of one or more pathways associated with a disease or condition 654 — Classify the subject as having a greater than 50% likelihood of developing the disease or condition associated with activation of the one or more pathways by applying a trained algorithm to the aligned sequence reads, where the trained algorithm has a greater than 50% positive predictive value or greater than 50% negative predictive value for predicting a greater than 50% likelihood of the subject developing the disease or condition associated with activation of the one or more pathway

FIG. 6C

| Class | |
|---|---|
| 1 | Non-Respond to All |
| 2 | Respond to All |
| 3 | Respond to IL17 & IL23 |
| 4 | Respond to IL17 & TNFalpha |
| 5 | Respond to IL17 Only |
| 6 | Respond to IL23 & TNFalpha |
| 7 | Respond to IL23 Only |
| 8 | Respond to TNFalpha Only |

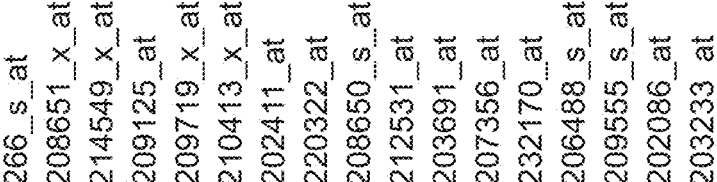
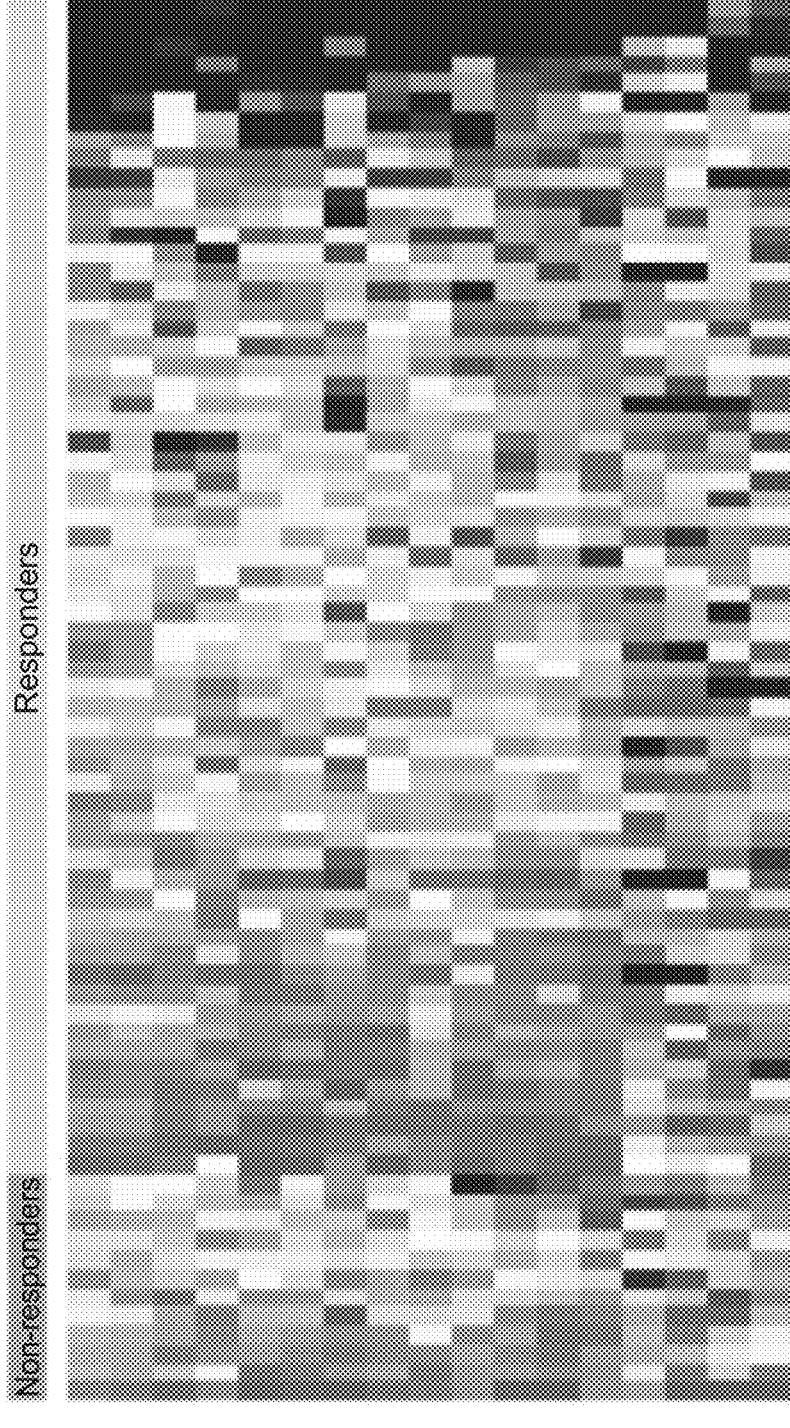
FIG. 12

METHODS OF TREATING PSORIASIS

BACKGROUND

Nearly 4% of the world's population is affected by one of the more than 80 known autoimmune diseases. In the United States alone, 24 million people are afflicted by an autoimmune disease. The cost of treating autoimmune diseases in the United States is estimated to be greater than 100 billion US dollars, annually. Autoimmune diseases can encompass a wide variety of different diseases and conditions that may impact a single tissue or organ, or many tissues or organs simultaneously. Some autoimmune diseases specifically target the skin. While the etiology of any particular autoimmune disease is often unknown, an imbalance in immune regulation is often involved.

For example, psoriasis is a chronic autoimmune disease characterized by raised areas of abnormal skin. It is a chronic condition that can cause thick, scaly patches, or plaques, to form on the skin. It is estimated that more than 8 million people in the United States have psoriasis. Currently, there is no cure for psoriasis, although there are treatments available to control the symptoms.

Microneedle devices comprising arrays of relatively small structures, sometimes referred to as microneedles or micropins, can be used in connection with the delivery of therapeutic agents and other substances through the skin and other surfaces. While treatments exist for autoimmune diseases, patient response is variable. There is a need for new strategies for determining a likelihood that a subject with an autoimmune disease will respond to a therapeutic drug.

To treat a subject's autoimmune disease, a physician may prescribe a therapeutic aimed at inhibiting or blocking a particular immune system biochemical pathway to manage symptoms. Unfortunately, due to the genetic variability of subjects with autoimmune diseases, a single therapeutic may not be an ideal candidate for two subjects with similar autoimmune diseases. This variability between subjects' genetic profiles leads to a trial and error methodology for prescribing therapeutics, often requiring several months of administering a therapeutic that may prove to be ineffective in treating a given subject. This approach is both costly to insurance payers and an ineffective route of managing an autoimmune disease that may have substantial impact on quality of life for the subject.

SUMMARY

An aspect of the present disclosure provides a microneedle device comprising: 1) a microneedle region comprising (i) a microneedle base substrate comprising a first base substrate surface and a second base substrate surface, wherein the first base substrate surface and the second base substrate surface are positioned on opposite sides of the microneedle base substrate; and (ii) a plurality of microneedles protruding from the first base substrate surface; and b) a support substrate adjacent to the microneedle base substrate, the support substrate connected to or integral with the microneedle base substrate and comprising a support substrate depth, wherein the support substrate depth is greater than the minimum distance between the first base substrate surface and the second base substrate surface.

Another aspect of the present disclosure provides a microneedle device comprising: 1) a microneedle region comprising a microneedle base substrate comprising a first base substrate surface with a plurality of microneedles protruding from the first base substrate surface, the microneedle base substrate also comprising a second base substrate surface on a side opposite from the first base substrate surface, the second base substrate surface comprising a recess aligned with at least a portion of the plurality of microneedles; and b) a support substrate adjacent to the microneedle base substrate, the support substrate connected to or integral with the microneedle base substrate.

In some embodiments, the minimum distance between the first base substrate surface and the second base substrate surface of the microneedle base substrate is between about 1 μm to about 500 μm less than the depth of the support substrate. In some embodiments, the minimum distance between the first base substrate surface and the second base substrate surface is between 150 μm to about 350 μm. In some embodiments, the ratio between (a) the minimum distance between the first base substrate surface and the second base substrate surface, and (b) the support substrate depth is at least 1:5. In some embodiments, the microneedle region comprises a perimeter and the support substrate are adjacent to at least half of the perimeter. In some embodiments, the support substrate comprises a first support substrate surface proximal to the plurality of microneedles (at times, referred to herein as "the front surface of the support substrate surface") and a second support substrate surface distal to the plurality of microneedles (at times, referred to herein as "the back surface of the support substrate surface") and positioned opposite to the first support substrate surface, and wherein the second base substrate surface is not coplanar with the second support substrate surface distal to the plurality of microneedles. In some embodiments, the first base substrate surface is not coplanar with a surface of the support substrate. In some embodiments, the plurality of microneedles is plasma treated. In some embodiments, a plurality of probes is coupled to a microneedle of the plurality of microneedles. In some embodiments, the plurality of probes comprises a negative charge. In some embodiments, the plurality of microneedles comprises a polyolefine resin. In some embodiments, the polyolefine resin comprises one or both of Zeonor 1020R or Zeonor 690R. In some embodiments, a microneedle of the plurality of microneedles is non-dissolvable. In some embodiments, a microneedle of the plurality of microneedles is pyramidal. In some embodiments, a microneedle of the plurality of microneedles is solid. In some embodiments, an angle between a base of the microneedle and the microneedle base substrate is between about 60° and about 90°. In some embodiments, the recess aligned with at least a portion of the plurality of microneedles comprises a width that is greater than a width of a mechanical applicator.

Another aspect of the present disclosure provides a kit comprising microneedle device comprising: 1) a microneedle region comprising a microneedle base substrate comprising a first base substrate surface with a plurality of microneedles protruding from the first base substrate surface, the microneedle base substrate also comprising a second base substrate surface on a side opposite from the first base substrate surface, the second base substrate surface comprising a recess aligned with at least a portion of the plurality of microneedles; and b) a support substrate adjacent to the microneedle base substrate, the support substrate connected to or integral with the microneedle base substrate, and (c) a mechanical applicator that fits within the recess aligned with at least a portion of the plurality of microneedles.

In some embodiments, at least one of the plurality of microneedles is coupled to a nucleic acid probe. In some embodiments, the nucleic acid probe comprises a homopoly-meric sequence. In some embodiments, the homopolymeric sequence comprises thymine or uracil. In some embodi-ments, the nucleic acid probe comprises DNA. In some embodiments, the nucleic acid probe comprises thymine. In some embodiments, the nucleic acid probe comprises thy-midine. In some embodiments, the nucleic acid probe is covalently linked to the microneedle. In some embodiments, the support substrate comprises a fiducial marker. In some embodiments, no more than three microneedles of the plu-rality of microneedles are less than 600 µm in length or more than 1050 µm in length.

Another aspect of the present disclosure provides a method of preparing a biological sample from a subject comprising: contacting skin of the subject with any one of the microneedle devices described herein, applying pressure to the microneedle device such that the microneedle device penetrates the skin of the subject; and allowing nucleic acids within the skin of the subject to contact the microneedle device. In some embodiments, the method further comprises extracting nucleic acids, including, for example, RNA, mRNA. In some embodiments, the method further com-prises converting mRNA to cDNA. In some embodiments, the subject is human. In some embodiments, the subject has psoriasis or symptoms of psoriasis. In some embodiments, the subject has a skin condition or symptoms of a skin condition.

Another aspect of the present disclosure provides a method of preparing a biological sample from a subject comprising: a) contacting skin of the subject with a microneedle device, wherein the microneedle device com-prises a plurality of nucleic acid probes coupled to a microneedle; b) applying pressure to the microneedle device such that the microneedle device penetrates the skin of the subject; c) allowing the microneedle device to penetrate the skin of the subject for no more than 10 minutes to obtain a ribonucleic acid (RNA) sample hybridized to the nucleic acid probes, wherein the RNA sample comprises a popula-tion of RNA fragments comprising about 700 bases or more and a population of RNA fragments comprising about 150 bases to about 200 bases, and wherein a ratio of the population of RNA fragments comprising about 700 bases or more to the population of RNA fragments comprising about 150 bases to about 200 bases is greater than 1; and d) removing the microneedle device from the skin of the subject, the microneedle device comprising the RNA sample hybridized to the nucleic acid probes after removal of the microneedle device from the skin of the subject. In some embodiments, the RNA sample is substantially free of contaminants. In some embodiments, the microneedle device is allowed to penetrate the skin of the subject for about 5 minutes. In some embodiments, the microneedle device penetrates the skin of the subject for less than 60 minutes, less than 45 minutes, less than 40 minutes, less than 30 minutes, less than 15 minutes, less than 10 minutes, less than 5 minutes, less than 3 minutes, less than 2 minutes, or less than 1 minute. In some embodiments, the microneedle device penetrates the skin of the subject for greater than 30 seconds, greater than 45 seconds, greater than 1 minutes, greater than 5 minutes, greater than 10 minutes, or greater than 30 minutes.

Another aspect of the present disclosure comprises method of treating a subject with an autoimmune disease of the skin comprising: a) collecting a sample comprising RNA derived from skin from the subject, wherein the subject has not been administered the autoimmune therapeutic drug within 7 days prior to the collecting the sample comprising RNA; b) determining an expression level of at least one gene based on the RNA; c) predicting that a subject with the autoimmune disease of the skin will be responsive to the autoimmune therapeutic drug with a positive predictive value greater than 80% based on the expression level of the at least one gene; and d) based on the predicting in (c), treating the subject with the autoimmune therapeutic drug. In some cases, the PPV is greater than 90%. In some cases, the PPV is greater than 95% for a cohort that has greater than 100 patients. In some instances, the autoimmune therapeutic drug is a biologic or comprises an antibody. In some cases, the autoimmune therapeutic drug is an IL-17 mediated treatment, an IL-23 mediated treatment, or a TNFα mediated treatment. In some cases, the autoimmune therapeutic drug is at least one drug selected from the group consisting of etanercept, infliximab, adalimumab, certolizumab, ustekinumab, secukinumab, ixekizumab, brodalumab, guselkumab, tildrakizumab, and risankizumab. In some embodiments, the at least one gene comprises at least two genes, three genes, four genes, or five genes. In some embodiments, the at least one gene comprises at least two genes, three genes, four genes, five genes, six genes, seven genes, eight genes, nine genes, or ten genes from Table 6, Table 12, or Table 13. In some instances, the at least one gene comprises at least two genes that do not share a common upstream regulator. In some cases, the autoimmune disorder is psoriasis. In some cases, the subject has a PASI greater than 8. In some cases, the subject has a PASI of at least 75 following the treating of the subject with the autoimmune therapeutic drug. In some cases, the RNA comprises mRNA or microRNA, and is converted into cDNA, and then sequenced using next generation sequenc-ing. In some cases, collecting a sample comprising RNA derived from skin from the subject comprises penetrating the skin of the subject with a microneedle device, wherein the microneedle device comprises microneedles conjugated to nucleic acid probes. In some embodiments, a trained algo-rithm is applied to data generated by the next generation sequence of the cDNA. In some embodiments, the algorithm was trained using samples from patients that were admin-istered a single type of drug selected from the group con-sisting of: IL-17 mediated treatment, TNF-alpha mediated treatment and IL-23 mediated treatment. In some embodi-ments, the autoimmune therapeutic drug is an IL-17-medi-ated treatment and the at least one gene comprises at least one gene that is not involved in an IL-17 mediated pathway. In some embodiments, the autoimmune therapeutic drug is an IL-23-mediated treatment and the at least one gene comprises at least one gene that is not involved in an IL-23 mediated pathway. In some embodiments, the autoimmune therapeutic drug is a TNF-α-mediated treatment and the at least one gene comprises at least one gene that is not involved in a TNF-α-mediated pathway.

Another aspect of the present disclosure comprises a method of determining whether a skin lesion of a subject will be responsive to an autoimmune therapeutic drug com-prising: collecting a sample comprising RNA derived from skin from the subject, wherein the subject has not been administered the autoimmune therapeutic drug within 7 days prior to the collecting the sample comprising RNA; con-verting the RNA into cDNA; determining expression of at least one gene based on the cDNA; and predicting whether the subject with the skin lesion will be responsive to the autoimmune therapeutic drug with a positive predictive value greater than 80%. In some instances, the PPV is greater than 90%. In some instances, the PPV is greater than 95% for a cohort that has greater than 100 patients. In some embodiments, the autoimmune therapeutic drug is a biologic or comprises an antibody. In some embodiments, the autoimmune therapeutic drug is an IL-17 mediated treatment, an IL-23 mediated treatment, or a TNFα mediated treatment. In some embodiments, the autoimmune therapeutic drug is at least one drug selected from the group consisting of: etanercept, infliximab, adalimumab, certolizumab, ustekinumab, secukinumab, ixekizumab, brodalumab, guselkumab, tildrakizumab, and risankizumab. In some embodiments, the autoimmune therapeutic drug is at least one drug selected from the group consisting of: certolizumab, ustekinumab, secukinumab, ixekizumab, brodalumab, guselkumab, tildrakizumab, and risankizumab. In some embodiments, the at least one gene comprises at least two genes, three genes, four genes, or five genes. In some embodiments, the at least one gene comprises at least two genes, three genes, four genes, five genes, six genes, seven genes, eight genes, nine genes, or ten genes from Table 6, Table 12, or Table 13. In some instances, the at least one gene comprises at least two genes that do not share a common upstream regulator. In some cases, the autoimmune disorder is psoriasis. In some cases, the subject has a PASI greater than 8. In some cases, the subject has a PASI of at least 75 following the treating of the subject with the autoimmune therapeutic drug. In some cases, the RNA comprises mRNA or microRNA, and is converted into cDNA, and then sequenced using next generation sequencing. In some cases, collecting a sample comprising RNA derived from skin from the subject comprises penetrating the skin of the subject with a microneedle device, wherein the microneedle device comprises microneedles conjugated to nucleic acid probes. In some embodiments, a trained algorithm is applied to data generated by the next generation sequence of the cDNA. In some embodiments, the algorithm was trained using samples from patients that were administered a single type of drug selected from the group consisting of IL-17 mediated treatment, TNF-alpha mediated treatment and IL-23 mediated treatment.

Another aspect of the present disclosure provides a method of determining whether a skin lesion of a subject will be responsive to an autoimmune therapeutic drug, comprising: penetrating skin of the subject with a microneedle device, wherein the microneedle device comprises one or more nucleic acid probes coupled to a microneedle; removing the microneedle device from the skin of the subject, thereby obtaining RNA molecules from the subject; performing high throughput sequencing on the RNA molecules to generate sequence reads; aligning the sequence reads with a signature of sequence reads associated with a positive response to an autoimmune disease therapeutic drug to obtain aligned sequence reads; and applying a trained algorithm to the aligned sequence reads, wherein the trained algorithm has a greater than 80% positive predictive value for predicting response to the autoimmune disease therapeutic drug.

Another aspect of the present disclosure provides a method of determining whether a skin lesion of a subject will be responsive to an autoimmune therapeutic drug comprising: penetrating skin of the subject with a microneedle device, wherein the microneedle device comprises one or more nucleic acid probes coupled to a solid microneedle; removing the microneedle device from the skin of the subject, thereby obtaining RNA molecules from the subject; performing high throughput sequencing on the RNA molecules to generate sequence reads; and aligning the sequence reads with a signature of sequence reads associated with a positive response to an autoimmune disease therapeutic drug to obtain aligned sequence reads; using the aligned sequence reads to determine an expression level of at least one RNA molecule; and applying a trained algorithm to the expression level of the at least one RNA molecule, wherein the trained algorithm predicts whether the subject with the skin lesion will be responsive to an IL-17 mediated treatment, an IL-23 mediated treatment, a TNFα mediated treatment, or any combination thereof. In some embodiments, the subject will be responsive to the to the IL-17 mediated treatment, the IL-23 mediated treatment, and the TNFα-mediated treatment. In some embodiments, the at least one gene comprises at least two genes, three genes, four genes, or five genes. In some embodiments, the at least one gene comprises at least two genes, three genes, four genes, five genes, six genes, seven genes, eight genes, nine genes, or ten genes from Table 6, Table 12, or Table 13. In some instances, the at least one gene comprises at least two genes that do not share a common upstream regulator. In some cases, the autoimmune disorder is psoriasis. In some cases, the subject has a PASI greater than 8. In some cases, the subject has a PASI of at least 75 following the treating of the subject with the autoimmune therapeutic drug. In some cases, the RNA comprises mRNA or microRNA, and is converted into cDNA, and then sequenced using next generation sequencing. In some embodiments, the recommended treatment comprises one or more autoimmune therapeutic drugs for an autoimmune disease or condition. In some embodiments, the recommended treatment comprises etanercept, infliximab, adalimumab, certolizumab, ustekinumab, secukinumab, ixekizumab, brodalumab, guselkumab, tildrakizumab, risankizumab, or any combination thereof.

In some embodiments, the method described herein further comprises performing high throughput sequencing on the RNA biomarkers to generate one or more sequence reads for the subject; aligning the one or more sequence reads for the subject with a known signature of sequence reads, wherein the known signature of sequence reads is associated with a positive response to the recommended treatment, thereby obtaining aligned sequence reads; and classifying the subject as having a likelihood of positively responding to the recommended treatment by applying a trained algorithm to the aligned sequence reads, wherein the trained algorithm comprises a greater than 50% positive predictive value for predicting a positive response to the recommended treatment. In some embodiments, the trained algorithm has greater than 50% negative predictive value.

Another aspect of the present disclosure provides a method of determining whether a subject with an autoimmune disorder of the skin will be responsive to an autoimmune therapeutic drug comprising: extracting mRNA from skin of the subject; sequencing the mRNA from the skin of the subject; and predicting whether the subject with the autoimmune disorder will be responsive to etanercept, adalimumab, infliximab, certolizumab, secukinumab, ixekizumab, broadalumab, guselkumab, tildrakizumab, and risankizumab with a positive predictive value greater than 80%.

Another aspect of the present disclosure provides a method of determining whether a skin lesion of a subject will be responsive to an IL-23 mediated treatment comprising: contacting skin of the subject with a microneedle device, wherein the microneedle device comprises one or more nucleic acid probes coupled to a solid microneedle such that the microneedle device penetrates the skin of the subject; removing the microneedle device from the skin of the subject, thereby obtaining RNA molecules from the subject; performing high throughput sequencing on the RNA molecules to generate sequence reads; and aligning the sequence reads with a signature of sequence reads associated with a positive response to an autoimmune disease therapeutic drug to obtain aligned sequence reads; and applying a trained algorithm to the aligned sequence reads, wherein the trained algorithm predicts whether the subject with the skin lesion will be responsive to an IL-23 mediated treatment and the aligned sequence reads correspond to at least one gene from Table 13.

Another aspect of the present disclosure provides a method of determining whether a skin lesion of a subject will be responsive to an IL-17, IL-23, or TNF-alpha mediated treatment comprising: contacting skin of the subject with a microneedle device, wherein the microneedle device comprises one or more nucleic acid probes coupled to a solid microneedle such that the microneedle device penetrates the skin of the subject; removing the microneedle device from the skin of the subject, thereby obtaining RNA molecules from the subject; performing high throughput sequencing on the RNA molecules to generate sequence reads; and aligning the sequence reads with a signature of sequence reads associated with a positive response to an autoimmune disease therapeutic drug to obtain aligned sequence reads; and applying a trained algorithm to the aligned sequence reads, wherein the trained algorithm predicts whether the subject with the skin lesion will be responsive to an IL-17 mediated treatment, a TNF-alpha-mediated treatment, or IL-23 mediated treatment and the aligned sequence reads correspond to at least one gene from Tables 6, 12 or 13. In some embodiments, subject is treated with IL-17 mediated treatment, wherein the aligned sequence reads correspond to at least one gene, two genes, three genes, four genes, five genes, or six genes from the table 12. In some embodiments, subject is treated with TNF-alpha mediated treatment, wherein the aligned sequence reads correspond to at least one gene, two genes, three genes, four genes, five genes, or six genes from the table 6. In some embodiments, subject is treated with IL-23 mediated treatment, wherein the aligned sequence reads correspond to at least one gene, two genes, three genes, four genes, five genes, or six genes from the table 13.

In some cases, the at least one gene is at least one gene, two genes, three genes, four genes, five genes, or six genes from the group consisting of CNFN, CTSC, GBAP1, CRABP2, PCDH7, PPIG, RAB31, C3, and EGR. In some cases, the at least one gene is at least one gene, two genes, three genes, four genes, five genes, or six genes from the group consisting of CNFN, CTSC, GBAP1, CRABP2, PCDH7, and PPIG. In some cases, the at least one gene is at least one gene, two genes, three genes, four genes, five genes, or six genes from the group consisting of PCDH7, PPIG, RAB31, C3, and EGR.

In some cases, the at least one gene is at least one gene, two genes, or three genes from the group consisting of CNFN, CTSC, GBAP1, and CRABP2. In some cases, the at least one gene is at least one gene, two genes, or three genes from the group consisting of PPIG, RAB31, C3, and EGR. In some cases, the at least one gene is at least one gene, two genes, or three genes from the group consisting of PCDH7, PPIG, RAB31, and C3. In some cases, the at least one gene is at least one gene, two genes, or three genes from the group consisting of GBAP1, CRABP2, PCDH7, PPIG.

In some cases, the at least one gene is at least one gene, two genes, three genes, four genes, five genes, or six genes from the group consisting of SERPINB3, SERPINB4, S100A7A, PI3, KRT6A, LCN2, DEFB4A, DEFB4B, SPRR1A, IL36G, MX1, IFI27, CD36, CD24, and IL4R. In some cases, the at least one gene is at least one gene, two genes, three genes, four genes, five genes, or six genes from the group consisting of KRT6A, SPRR1A, CD36, IL4R, LCN2, and IFI27. In some cases, the at least one gene is at least one gene, two genes, three genes, four genes, five genes, or six genes from the group consisting of CD36, IL4R, S100A7A, SERPINB4, MX1, and SERPINB3. In some cases, the at least one gene is at least one gene, two genes, three genes, four genes, five genes, or six genes from the group consisting of LCN2, IFI27, DEFB4A, IL36G, CD24, and PI3.

In some cases, the at least one gene is at least one gene, two genes, or three genes from the group consisting of IL4R, LCN2, and IFI27. In some cases, the at least one gene is at least one gene, two genes, or three genes from the group consisting of PI3, IFI27, and SERPINB3. In some cases, the at least one gene is at least one gene, two genes, or three genes from the group consisting of IL4R, S100A7A, and MX1. In some cases, the at least one gene is at least one gene, two genes, or three genes from the group consisting of CD36, LCN2, and SERPINB4.

In some cases, the at least one gene is at least one gene, two genes, three genes, four genes, five genes, or six genes from the group consisting of MTCO1P12, MTATP6P1, CLSTN1, PDPN, LDLRAD2, and GSTM3. In some cases, the at least one gene is at least one gene, two genes, three genes, four genes, five genes, or six genes from the group consisting of AL158847.1, DAD1, LDLRAD2, ZNF395, MGMT, and AL136982.4. In some cases, the at least one gene is at least one gene, two genes, three genes, four genes, five genes, or six genes from the group consisting of NREP, PPIF, PRIM1, AL136982.5, MTATP6P1, and SMPD3. In some cases, the at least one gene is at least one gene, two genes, three genes, four genes, five genes, or six genes from the group consisting of PDPN, TXNRD1, GSTM3, GPSM1, GLRX, and USP2.

In some cases, the at least one gene is at least one gene, two genes, or three genes from the group consisting of MTCO1P12, CLSTN1, and GSTM3. In some cases, the at least one gene is at least one gene, two genes, or three genes from the group consisting of NREP, PPIF, and PRIM1. In some cases, the at least one gene is at least one gene, two genes, or three genes from the group consisting of AL136982.5, MTATP6P1, and SMPD3. In some cases, the at least one gene is at least one gene, two genes, or three genes from the group consisting of PDPN, TXNRD1, and GSTM3.

Also provided herein, are microneedle devices, methods, and systems for characterizing a subject's autoimmune disease and the likelihood that a subject may respond positive to a given therapeutic to treat said subject's autoimmune disease.

An aspect of the present disclosure comprises a microneedle device comprising: a microneedle region comprising (i) a plurality of microneedles protruding from a front surface of a microneedle base substrate, (ii) a back surface of said microneedle base substrate; and (iii) a minimum distance between said front surface of said microneedle base substrate and said back surface of said microneedle base substrate; and a support substrate adjacent to at least one side of said microneedle base substrate, said support substrate connected to or integral with said microneedle base substrate and comprising a support substrate depth, wherein said support substrate depth is greater than said minimum distance between said front surface of said microneedle base substrate and said back surface of said microneedle base substrate.

Another aspect of the present disclosure comprises a microneedle device comprising: a microneedle region comprising a plurality of microneedles protruding from a front surface of a microneedle base substrate, said microneedle base substrate also comprising a back surface, said back surface comprising a recess directly behind at least a portion of said microneedle region; and a support substrate adjacent to at least one side of said microneedle base substrate, said support substrate connected to or integral with said microneedle base substrate. In some embodiments, said minimum distance between said front surface of said microneedle base substrate and said back surface of said microneedle base substrate is between about 1 μm to about 500 μm less than said depth of said support substrate. In some embodiments, said minimum distance between said front surface of said microneedle base substrate and said back surface of said microneedle base substrate is between 150 μm to about 350 μm. In some embodiments, said minimum distance between said front surface of said microneedle base substrate and said back surface of said microneedle base substrate and said support substrate depth comprise an about 1:5 ratio. In some embodiments, said minimum distance between said front surface of said microneedle base substrate and said back surface of said microneedle base substrate and said support substrate depth comprise at least about a 0.1:5 ratio, at least about a 0.5:5 ratio, at least about 1:5 ratio, at least about 2:5 ratio, at least 3:5 ratio, at least 4:5 ratio, at least 1:1 ratio, at least 1:2 ratio, at least 1:3 ratio, at least 1:4 ratio, at least about a 1:10 ratio, at least about a 1:15 ratio, at least about a 1:20 ratio, at least about 1:25 ratio, or at least about 1:50 ratio. In some embodiments, said minimum distance between said front surface of said microneedle base substrate and said back surface of said microneedle base substrate and said support substrate depth comprise at most about a 0.1:5 ratio, at most about a 0.5:5 ratio, at most about 1:5 ratio, at most about 2:5 ratio, at most 3:5 ratio, at most 4:5 ratio, at most 1:1 ratio, at most 1:2 ratio, at most 1:3 ratio, at most about 1:4 ratio, at most about a 1:10 ratio, at most about a 1:15 ratio, at most about a 1:20 ratio, at most about 1:25 ratio, or at most about 1:50 ratio. In some embodiments, said minimum distance between said front surface of said microneedle base substrate and said back surface of said microneedle base substrate and said support substrate depth comprise at least about a 2:1 ratio, at least about a 3:1 ratio, at least about 3:2 ratio, at least about 4:1 ratio, at least 5:1 ratio, at least 5:3 ratio, at least 6:1 ratio, at least 7:1 ratio, at least 10:1 ratio, at least 15:1 ratio, at least about a 20:1 ratio, at least about a 25:1 ratio, or at least about a 50:1 ratio. In some embodiments, said minimum distance between said front surface of said microneedle base substrate and said back surface of said microneedle base substrate and said support substrate depth comprise at most about a 2:1 ratio, at most about a 3:1 ratio, at most about 3:2 ratio, at most about 4:1 ratio, at most 5:1 ratio, at most 5:3 ratio, at most about 6:1 ratio, at most 7:1 ratio, at most 10:1 ratio, at most 15:1 ratio, at most about a 20:1 ratio, at most about a 25:1 ratio, or at most about a 50:1 ratio. In some embodiments, said microneedle region comprises a perimeter and said support substrate is adjacent to at least half of said perimeter. In some embodiments, said back surface of said microneedle base substrate is not coplanar with a back surface of said support substrate. In some embodiments, said front surface of said microneedle base substrate is not coplanar with a surface of said support substrate. In some embodiments, said plurality of microneedles is plasma treated. In some embodiments, a plurality of probes is coupled to a microneedle of said plurality of microneedles. In some embodiments, said plurality of probes comprises a negative charge. In some embodiments, said plurality of microneedles comprises a polyolefine resin. In some embodiments, said polyolefine resin comprises one or both of Zeonor 1020R or Zeonor 690R. In some embodiments, a microneedle of said plurality of microneedles is non-dissolvable. In some embodiments, a microneedle of said plurality of microneedles is pyramidal. In some embodiments, a microneedle of said plurality of microneedles is solid. In some embodiments, an angle between a base of said microneedle and said microneedle base substrate is between about 60° and about 90°. In some embodiments, said recess directly behind said at least a portion of said microneedle region comprises a width that is greater than a width of a mechanical applicator.

Another aspect of the present disclosure comprises a kit comprising (a) said device of some aspects described herein; and (b) a mechanical applicator that fits within said recess directly behind said at least a portion of said microneedle region. In some embodiments, at least one of said plurality of microneedles is coupled to a nucleic acid probe. In some embodiments, said nucleic acid probe comprises a homopolymeric sequence. In some embodiments, said homopolymeric sequence comprises thymine or uracil. In some embodiments said nucleic acid probe is covalently linked to said microneedle. In some embodiments, said support substrate comprises a fiducial marker. In some embodiments, no more than three microneedles of said plurality of microneedles are less than 600 μm in length or more than 1050 μm in length.

Another aspect of the present disclosure comprises a method of preparing a biological sample from a subject comprising: contacting skin of said subject with a microneedle device, wherein said microneedle device comprises a plurality of nucleic acid probes coupled to a microneedle; applying pressure to said microneedle device such that said microneedle device penetrates said skin of said subject; allowing said microneedle device to penetrate said skin of said subject for no more than 10 minutes to obtain a ribonucleic acid (RNA) sample hybridized to said nucleic acid probes, wherein said RNA sample comprises a population of RNA fragments comprising about 700 bases or more and a population of RNA fragments comprising about 150 bases to about 200 bases, and wherein a ratio of said population of RNA fragments comprising about 700 bases or more to said population of RNA fragments comprising about 150 bases to about 200 bases is greater than 1; and removing said microneedle device from said skin of said subject, said microneedle device comprising said RNA sample hybridized to said nucleic acid probes after removal of said microneedle device from said skin of said subject. In some embodiments, said RNA sample is substantially free of contaminants. In some embodiments, the method comprises allowing said microneedle device to penetrate said skin of said subject for about 5 minutes.

Another aspect of the present disclosure comprises a method of predicting an individual patient's response to a class of biologic drugs, by the mechanism of action of that class of agent, to optimize treatment selection. By using a machine learning approach, a classifier is trained to predict the response of a patient to either the IL-17, IL-23, or TNF class of biologics using baseline transcriptomic biomarkers (e.g., certain genes) and with high positive predictive value, For example, by using a machine learning-derived classifier to predict response to the anti-IL-17 and anti-IL-23 biologics in patients with psoriasis with high level of positive predictive value.

Another aspect of the present disclosure comprises an algorithm for the prediction of response to biologics (for example, anti-IL-17, anti-IL-23) used for the treatment of patients with psoriasis, by comparing baseline transcriptomes with clinical response to biologic drugs after initial treatment, for example, at 12 weeks after.

Another aspect of the present disclosure provides a method of determining whether a skin lesion of a subject will be responsive to an autoimmune therapeutic drug, comprising: penetrating skin of the subject with a microneedle device, wherein the microneedle device comprises one or more nucleic acid probes coupled to a microneedle; removing the microneedle device from the skin of the subject, thereby obtaining RNA molecules from the subject; performing high throughput sequencing on the RNA molecules to generate sequence reads; quantifying the RNA molecules comprising sequence reads associated with a positive response to an autoimmune disease therapeutic drug to determine an expression level of at least one gene; and applying a trained algorithm to the expression level, wherein the trained algorithm has a greater than 80% positive predictive value for predicting response to the autoimmune disease therapeutic drug.

Another aspect of the present disclosure provides a method of determining whether a skin lesion of a subject will be responsive to an autoimmune therapeutic drug comprising: penetrating skin of the subject with a microneedle device, wherein the microneedle device comprises one or more nucleic acid probes coupled to a solid microneedle; removing the microneedle device from the skin of the subject, thereby obtaining RNA molecules from the subject; performing high throughput sequencing on the RNA molecules to generate sequence reads; and quantifying the RNA molecules comprising sequence reads associated with a positive response to an autoimmune disease therapeutic drug to determine an expression level of at least one gene; and applying a trained algorithm to the expression level of the at least one RNA molecule, wherein the trained algorithm predicts whether the subject with the skin lesion will be responsive to an IL-17 mediated treatment, an IL-23 mediated treatment, a TNFα mediated treatment, or any combination thereof. In some embodiments, the subject will be responsive to the to the IL-17 mediated treatment, the IL-23 mediated treatment, and the TNFα-mediated treatment. In some embodiments, the at least one gene comprises at least two genes, three genes, four genes, or five genes. In some embodiments, the at least one gene comprises at least two genes, three genes, four genes, five genes, six genes, seven genes, eight genes, nine genes, or ten genes from Table 6, Table 12, or Table 13. In some instances, the at least one gene comprises at least two genes that do not share a common upstream regulator. In some cases, the autoimmune disorder is psoriasis. In some cases, the subject has a PASI greater than 8. In some cases, the subject has a PASI of at least 75 following the treating of the subject with the autoimmune therapeutic drug. In some cases, the RNA comprises mRNA or microRNA, and is converted into cDNA, and then sequenced using next generation sequencing. In some embodiments, the recommended treatment comprises one or more autoimmune therapeutic drugs for an autoimmune disease or condition. In some embodiments, the recommended treatment comprises etanercept, infliximab, adalimumab, certolizumab, ustekinumab, secukinumab, ixekizumab, brodalumab, guselkumab, tildrakizumab, risankizumab, or any combination thereof.

In some embodiments, the method described herein further comprises performing high throughput sequencing on the RNA biomarkers to generate one or more sequence reads for the subject; quantifying the RNA molecules comprising one or more sequence reads for the subject with a known signature of sequence reads, wherein the known signature of sequence reads is associated with a positive response to the recommended treatment, thereby obtaining aligned sequence reads; and classifying the subject as having a likelihood of positively responding to the recommended treatment by applying a trained algorithm to the aligned sequence reads, wherein the trained algorithm comprises a greater than 50% positive predictive value for predicting a positive response to the recommended treatment. In some embodiments, the trained algorithm has greater than 50% negative predictive value.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 5A-C illustrate quality of different RNA samples collected with a microneedle device as described herein-measured in length of RNA fragments contained in the sample. FIG. 5A illustrates an undegraded sample. FIGS. 5B and 5C illustrate degraded samples.

FIG. 6A illustrates an example flow diagram for a method of treating one or more subjects with a mild or severe form of a skin condition, as described in some embodiments herein.

FIG. 6B shows an example flow diagram for a method of preparing a biological sample and identifying one or more therapeutic drugs for one or more subjects, as described in some embodiments herein.

FIG. 6C shows an example flow diagram for identifying the activation of one or more pathways that may be associated with a disease or condition in a subject.

FIG. 8A: 43 patients treated with IL-23i; FIG. 8B: 31 patients treated with IL-17i; FIG. 8C: 11 patients treated with TNFαi. X-axis: predicted responder or non-responder; Y-axis: Week 12 PASI changes. Red dot: median PASI change value.

FIG. 12 shows heatmap generated from expression data for the 17 genes identified as correlating to response to anti-IL-17 biologic treatment.

DETAILED DESCRIPTION

Overview

Figure 1:
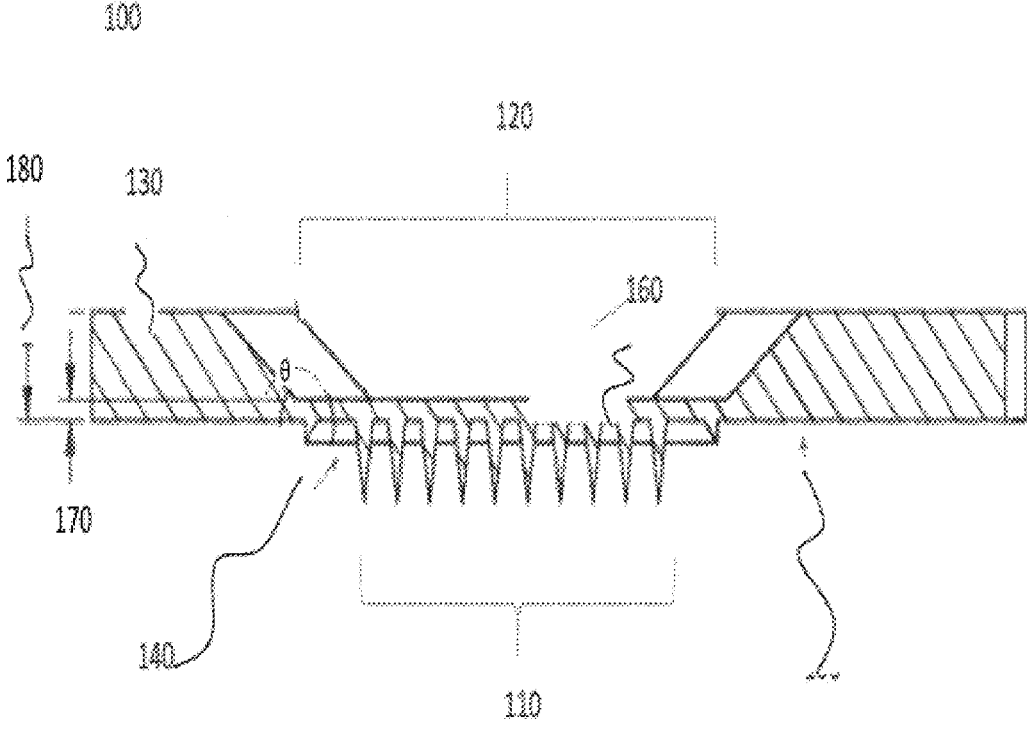
FIG. 1 illustrates a cross section of a microneedle device as described herein.

Described herein are microneedle devices comprising features that result in precise, patient-friendly sample collection, including microneedle devices comprising features that may minimize pain during the sample collection process. The devices described herein can be specifically designed such that they can be fabricated by scalable processes. Features such as the varying thickness of the distinct areas of the devices described herein can result in uniform and precise microneedle devices. The specific features of the microneedle devices described herein may further result in sharper microneedles that are not described in the current state of the art. These sharp microneedles may result in an enhanced user or patient (e.g. the subject) experience wherein the user may experience much less pain as compared to microneedle devices of the current state of the art. Combining the precision of the microneedle devices with the enhanced user experience can result in more precise and accurate analysis of biological samples (e.g. the user's skin).

Generally, the microneedle devices provided herein may contain probes attached to the microneedle. In some cases, these probes are configured to bind to one or more biomarkers within a sample or tissue (e.g., skin) of a subject in such a manner as to permit extraction of the biomarker for further analysis. The extracted biomarkers can be analyzed, alone or in combination (e.g. generating a genetic signature or gene expression profile) to provide a diagnosis or prediction of a response to a drug or other therapeutic treatment with respect to the subject.

Further provided herein are methods and systems for determining a gene expression profile from a subject. In some cases, the gene expression profile is useful for determining an appropriate treatment regimen for an autoimmune disease. Thus, the methods of the disclosure are useful for personalized medicine, wherein treatment is tailored to a subject based on the particular characteristics of the disease in the subject.

In some embodiments, the present disclosure provides a microneedle device. In some embodiments, the microneedle device comprises a microneedle region and a support substrate. The microneedle region may comprise a plurality of microneedles protruding from a front or first surface of a microneedle base substrate 110, a back surface (or second base substrate surface) of the microneedle base substrate 160; and a minimum distance between the front surface of the microneedle base substrate and the back surface of the microneedle base substrate 170. In some embodiments, the minimum distance between the front surface of the microneedle base substrate and the back surface of the microneedle base substrate 170 configures the device such that during some methods of manufacturing the device, a molten medium (e.g. the polyolefin resins described herein) will fill a mold of the microneedles prior to filling the mold of other sections of the device. In some embodiments, the minimum distance between the front surface of the microneedle base substrate and the back surface of the microneedle base substrate 170 configures the device such that the device comprises uniform and/or sharp microneedles. In some embodiments, the uniform and/or sharp microneedles result in an enhanced user experience for a subject using the device. In some embodiments, the enhanced user experience comprises lessened pain experienced by the subject using the device.

This disclosure provides microneedle devices for detection and acquisition of biomarkers from a subject in situ. The microneedle-based device may contain one or more microneedles that can be pierced into biological barriers such as the skin or mucous membrane. Often, the microneedles are non-invasive, or minimally-invasive. When a plurality of microneedles is present, the device can also have a planar substrate which supports the microneedles. The substrate can be made of the same material as that of the microneedle. It can also be made of a different material.

Microneedle Devices

Microneedle devices of the present disclosure may comprise a base substrate comprising a microneedle region, and a support substrate. FIG. 1 illustrates a side view of an exemplary microneedle device 100, comprising microneedles, 110, on a microneedle base substrate, 120. The microneedle base substrate comprises a front surface (used interchangeably herein with the term "first base substrate surface"), 140, wherein the microneedles, 110, protrude from the front surface (or first base substrate surface), and a back surface (used interchangeably herein with the term "second base substrate surface"), 160. The device may comprise a support substrate, 130, adjacent to at least one side of the interior microneedle base substrate, 120, the support substrate connected to or integral with the microneedle base substrate. In some embodiments, an angle is formed between the back surface of the microneedle base substrate, 160 and the adjacent support substrate, 130.

In some embodiments, the angle formed between the back surface of the microneedle base substrate, 160, and the adjacent support substrate, 130, is a right angle or obtuse angle, e.g., about 90° to about 179°. The angle (θ) formed between the back surface of the microneedle base substrate, 160, and the adjacent support substrate, 130, generally refers to an angle that spans a region of space interior to the device; while the adjacent support substrate generally comprises a complementary angle (α) spanning the substrate and that is often an acute angle (e.g., between 1° and 90°). In some embodiments, the angle (θ) formed between the back surface of the microneedle base substrate and the adjacent support substrate is about 110°. In some embodiments, the angle (θ) formed between the back surface of the microneedle base substrate and the adjacent support substrate is about 90° to about 100°, about 90° to about 110°, about 90° to about 120°, about 90° to about 130°, about 90° to about 140°, about 90° to about 150°, about 90° to about 160°, about 90° to about 170°, about 90° to about 179°, about 100° to about 110°, about 100° to about 120°, about 100° to about 130°, about 100° to about 140°, about 100° to about 150°, about 100° to about 160°, about 100° to about 170°, about 100° to about 179°, about 110° to about 120°, about 110° to about 130°, about 110° to about 140°, about 110° to about 150°, about 110° to about 160°, about 110° to about 170°, about 110° to about 179°, about 120° to about 130°, about 120° to about 140°, about 120° to about 150°, about 120° to about 160°, about 120° to about 170°, about 120° to about 179°, about 130° to about 140°, about 130° to about 150°, about 130° to about 160°, about 130° to about 170°, about 130° to about 179°, about 140° to about 150°, about 140° to about 160°, about 140° to about 170°, about 140° to about 179°, about 150° to about 160°, about 150° to about 170°, about 150° to about 179°, about 160° to about 170°, about 160° to about 179°, or about 170° to about 179°. In some embodiments, the angle formed is between the back surface of the microneedle base substrate and the adjacent support substrate is about 90°, about 100°, about 110°, about 120°, about 130°, about 140°, about 150°, about 160°, about 170°, or about 179°. In some embodiments, the angle formed between the back surface of the microneedle base substrate and the adjacent support substrate is at least about 90°, about 100°, about 110°, about 120°, about 130°, about 140°, about 150°, about 160°, or about 170°. In some embodiments, the angle formed between the back surface of the microneedle base substrate and the adjacent support substrate is at most about 100°, about 110°, about 120°, about 130°, about 140°, about 150°, about 160°, about 170°, or about 179°.

The resulting shape of the support substrate, 130, may also influence the speed and uniformity of the flow of polymer and/or resin into the section mold resembling the structure of the device during manufacturing of the device. In some embodiments, the resulting shape of the support substrate, 130, is circular. In some embodiments, the resulting shape of the support substrate, 130, is linear.

In some cases, the arrangement of the microneedles is a circular pattern with a radius of the microneedle section being about 0.95 mm to about 4.15 mm. In some embodiments, the radius is about 4.0 mm. In some embodiments, the radius is about 0.95 mm to about 1.4 mm, about 0.95 mm to about 1.75 mm, about 0.95 mm to about 2.15 mm, about 0.95 mm to about 2.55 mm, about 0.95 mm to about 2.95 mm, about 0.95 mm to about 3.35 mm, about 0.95 mm to about 3.75 mm, about 0.95 mm to about 4.15 mm, about 1.4 mm to about 1.75 mm, about 1.4 mm to about 2.15 mm, about 1.4 mm to about 2.55 mm, about 1.4 mm to about 2.95 mm, about 1.4 mm to about 3.35 mm, about 1.4 mm to about 3.75 mm, about 1.4 mm to about 4.15 mm, about 1.75 mm to about 2.15 mm, about 1.75 mm to about 2.55 mm, about 1.75 mm to about 2.95 mm, about 1.75 mm to about 3.35 mm, about 1.75 mm to about 3.75 mm, about 1.75 mm to about 4.15 mm, about 2.15 mm to about 2.55 mm, about 2.15 mm to about 2.95 mm, about 2.15 mm to about 3.35 mm, about 2.15 mm to about 3.75 mm, about 2.15 mm to about 4.15 mm, about 2.55 mm to about 2.95 mm, about 2.55 mm to about 3.35 mm, about 2.55 mm to about 3.75 mm, about 2.55 mm to about 4.15 mm, about 2.95 mm to about 3.35 mm, about 2.95 mm to about 3.75 mm, about 2.95 mm to about 4.15 mm, about 3.35 mm to about 3.75 mm, about 3.35 mm to about 4.15 mm, or about 3.75 mm to about 4.15 mm. In some embodiments, the radius is about 0.95 mm, about 1.4 mm, about 1.75 mm, about 2.15 mm, about 2.55 mm, about 2.95 mm, about 3.35 mm, about 3.75 mm, or about 4.15 mm. In some embodiments, the radius is at least about 0.95 mm, about 1.4 mm, about 1.75 mm, about 2.15 mm, about 2.55 mm, about 2.95 mm, about 3.35 mm, or about 3.75 mm. In some embodiments, the radius is at most about 1.4 mm, about 1.75 mm, about 2.15 mm, about 2.55 mm, about 2.95 mm, about 3.35 mm, about 3.75 mm, or about 4.15 mm.

In some cases, the arrangement of the microneedles is a linear square pattern with total edge length of about 2.14 mm to about 9.34 mm. In some embodiments, the distance is about 4.0 mm. In some embodiments, the distance is about 2.14 mm to about 3.04 mm, about 2.14 mm to about 3.94 mm, about 2.14 mm to about 4.84 mm, about 2.14 mm to about 5.74 mm, about 2.14 mm to about 6.64 mm, about 2.14 mm to about 7.54 mm, about 2.14 mm to about 8.44 mm, about 2.14 mm to about 9.34 mm, about 3.04 mm to about 3.94 mm, about 3.04 mm to about 4.84 mm, about 3.04 mm to about 5.74 mm, about 3.04 mm to about 6.64 mm, about 3.04 mm to about 7.54 mm, about 3.04 mm to about 8.44 mm, about 3.04 mm to about 9.34 mm, about 3.94 mm to about 4.84 mm, about 3.94 mm to about 5.74 mm, about 3.94 mm to about 6.64 mm, about 3.94 mm to about 7.54 mm, about 3.94 mm to about 8.44 mm, about 3.94 mm to about 9.34 mm, about 4.84 mm to about 5.74 mm, about 4.84 mm to about 6.64 mm, about 4.84 mm to about 7.54 mm, about 4.84 mm to about 8.44 mm, about 4.84 mm to about 9.34 mm, about 5.74 mm to about 6.64 mm, about 5.74 mm to about 7.54 mm, about 5.74 mm to about 8.44 mm, about 5.74 mm to about 9.34 mm, about 6.64 mm to about 7.54 mm, about 6.64 mm to about 8.44 mm, about 6.64 mm to about 9.34 mm, about 7.54 mm to about 8.44 mm, about 7.54 mm to about 9.34 mm, or about 8.44 mm to about 9.34 mm. In some embodiments, the distance is about 2.14 mm, about 3.04 mm, about 3.94 mm, about 4.84 mm, about 5.74 mm, about 6.64 mm, about 7.54 mm, about 8.44 mm, or about 9.34 mm. In some embodiments, the distance is at least about 2.14 mm, about 3.04 mm, about 3.94 mm, about 4.84 mm, about 5.74 mm, about 6.64 mm, about 7.54 mm, or about 8.44 mm. In some embodiments, the distance is at most about 3.04 mm, about 3.94 mm, about 4.84 mm, about 5.74 mm, about 6.64 mm, about 7.54 mm, about 8.44 mm, or about 9.34 mm.

In some embodiments, the surface from which the microneedles protrude from, and which is applied to the tissue of interest may be termed the bottom surface or front surface. In some embodiments, the surface that is opposite to the surface from which the microneedles protrude from, 160, may be termed the back or top surface.

In some embodiments, the microneedle base substrate, 120, is defined by the presence of microneedles. The microneedle base substrate, 120, may be thinner and/or narrower than the support substrate, 130, e.g. the distance between the front surface of the microneedle base substrate, 140, and back surface of the microneedle base substrate, 160, termed $D_{BS}$ (170 in FIG. 1) is less than the distance between the respective, adjacent surfaces of the support substrate, 130, termed $D_{SS}$ (180 in FIG. 1). The difference in depth between the microneedle base substrate, 120, and the support substrate, 130, may create a recess in the device, the recess located adjacent to the microneedle base substrate, 120. This structural feature is particularly advantageous because having a narrow microneedle base substrate, 120, improves the flow and/or penetration of a polymer/resin used to fabricate the device into a mold resembling the structure of the device during manufacturing, specifically the flow and/or penetration of the polymer/resin into the section of the mold corresponding to the microneedles is increased due to this structural feature of a difference in depth between the microneedle base substrate, 120, and the support substrate, 130, resulting in more uniform and sharper microneedles. Sharper microneedles may cause less tissue damage when inserted, and therefore, may result in less pain to a subject. More uniform microneedles result in more standard and scalable manufacturing methods.

In some embodiments, the narrower microneedle base substrate may also concentrate pressure through the microneedles when the device is applied to skin or other tissues. In some cases, the minimum distance between the front surface of the microneedle base substrate, 140, and the back surface of the microneedle base substrate, 150 is between about 1 μm to about 500 μm less than the distance from the front surface of the support substrate to the back surface of the support substrate.

In some embodiments, the difference in depth between the microneedle base substrate ($D_{BS}$) and the support substrate ($D_{SS}$) is about 1 µm to about 550 µm. In some embodiments, the difference in depth between the microneedle base substrate ($D_{BS}$) and the support substrate ($D_{SS}$) is about 250 µm. In some embodiments, the difference in depth between the microneedle base substrate ($D_{BS}$) and the support substrate ($D_{SS}$) is about 1 µm to about 50 µm, about 1 µm to about 100 µm, about 1 µm to about 150 µm, about 1 µm to about 200 µm, about 1 µm to about 250 µm, about 1 µm to about 300 µm, about 1 µm to about 350 µm, about 1 µm to about 400 µm, about 1 µm to about 450 µm, about 1 µm to about 500 µm, about 1 µm to about 550 µm, about 50 µm to about 100 µm, about 50 µm to about 150 µm, about 50 µm to about 200 µm, about 50 µm to about 250 µm, about 50 µm to about 300 µm, about 50 µm to about 350 µm, about 50 µm to about 400 µm, about 50 µm to about 450 µm, about 50 µm to about 500 µm, about 50 µm to about 550 µm, about 100 µm to about 150 µm, about 100 µm to about 200 µm, about 100 µm to about 250 µm, about 100 µm to about 300 µm, about 100 µm to about 350 µm, about 100 µm to about 400 µm, about 100 µm to about 450 µm, about 100 µm to about 500 µm, about 100 µm to about 550 µm, about 150 µm to about 200 µm, about 150 µm to about 250 µm, about 150 µm to about 300 µm, about 150 µm to about 350 µm, about 150 µm to about 400 µm, about 150 µm to about 450 µm, about 150 µm to about 500 µm, about 150 µm to about 550 µm, about 200 µm to about 250 µm, about 200 µm to about 300 µm, about 200 µm to about 350 µm, about 200 µm to about 400 µm, about 200 µm to about 450 µm, about 200 µm to about 500 µm, about 200 µm to about 550 µm, about 250 µm to about 300 µm, about 250 µm to about 350 µm, about 250 µm to about 400 µm, about 250 µm to about 450 µm, about 250 µm to about 500 µm, about 250 µm to about 550 µm, about 300 µm to about 350 µm, about 300 µm to about 400 µm, about 300 µm to about 450 µm, about 300 µm to about 500 µm, about 300 µm to about 550 µm, about 350 µm to about 400 µm, about 350 µm to about 450 µm, about 350 µm to about 500 µm, about 350 µm to about 550 µm, about 400 µm to about 450 µm, about 400 µm to about 500 µm, about 400 µm to about 550 µm, about 450 µm to about 500 µm, about 450 µm to about 550 µm, or about 500 µm to about 550 µm. In some embodiments, the difference in depth between the microneedle base substrate and the support substrate is about 1 µm, about 50 µm, about 100 µm, about 150 µm, about 200 µm, about 250 µm, about 300 µm, about 350 µm, about 400 µm, about 450 µm, about 500 µm, or about 550 µm. In some embodiments, the difference in depth between the microneedle base substrate ($D_{BS}$) and the support substrate ($D_{SS}$) is at least about 1 µm, about 50 µm, about 100 µm, about 150 µm, about 200 µm, about 250 µm, about 300 µm, about 350 µm, about 400 µm, about 450 µm, or about 500 µm. In some embodiments, the difference in depth between the microneedle base substrate and the support substrate is at most about 50 µm, about 100 µm, about 150 µm, about 200 µm, about 250 µm, about 300 µm, about 350 µm, about 400 µm, about 450 µm, about 500 µm, or about 550 µm.

In some cases, the minimum distance between the front surface of the microneedle base substrate and the back surface of the microneedle base substrate ($D_{BS}$) is between 150 µm to about 350 µm. In some cases, the ratio of the distance between the front and back of the interior section and the front and back of the peripheral section is about a 1:2, 1:3, 1:4, 1:5, 1:6, 1:7, 1:8, 1:9, or 1:10 ratio.

In some cases, the microneedle section, or region, comprises a perimeter and the peripheral region, or support substrate, is adjacent to at least half of the perimeter. In some cases, the back surface of the microneedle base substrate is not coplanar with a back surface of the support substrate. In some cases, the front surface of the microneedle base substrate is not coplanar with a surface of the support substrate.

Figure 2:
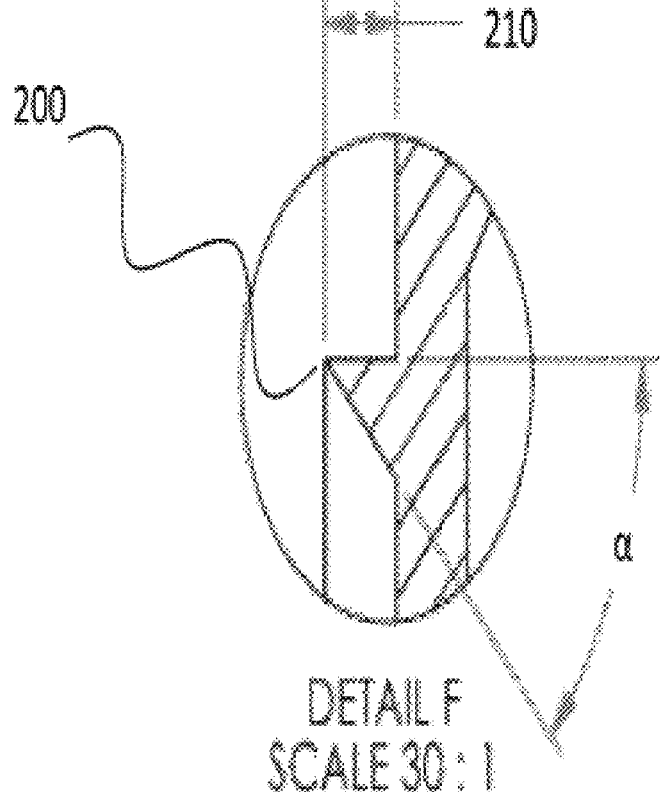
FIG. 2 illustrates a detail from the cross section of FIG. 1.

FIG. 2 provides a detail view of the circled region in FIG. 1. In some embodiments, the interior section may also have a ridge, 200, which surrounds the microneedle region. The ridge may protrude from the surface from which the microneedles protrude from. In some embodiments, the height of the ridge, HR (210 in FIG. 2), may be about 250 µm. In some embodiments, the height of the ridge, HR may be about 50 µm, 100 µm, 150 µm, 200 µm, 250 µm, 254 µm, 300 µm, 350 µm, 400 µm, or 450 µm. In some cases, the ridge surrounding the interior section may increase or maintain surface tension of a tissue, such as skin, when the device is applied to the tissue. In some cases, the angle formed between the ridge and the bottom surface is about 5° to about 85°. In some cases, the angle formed between the ridge and the bottom surface is about 45°. In some cases, the angle formed between the ridge and the bottom surface is about 5° to about 10°, about 5° to about 20°, about 5° to about 30°, about 5° to about 40°, about 5° to about 50°, about 5° to about 60°, about 5° to about 70°, about 5° to about 80°, about 5° to about 85°, about 10° to about 20°, about 10° to about 30°, about 10° to about 40°, about 10° to about 50°, about 10° to about 60°, about 10° to about 70°, about 10° to about 80°, about 10° to about 85°, about 20° to about 30°, about 20° to about 40°, about 20° to about 50°, about 20° to about 60°, about 20° to about 70°, about 20° to about 80°, about 20° to about 85°, about 30° to about 40°, about 30° to about 50°, about 30° to about 60°, about 30° to about 70°, about 30° to about 80°, about 30° to about 85°, about 40° to about 50°, about 40° to about 60°, about 40° to about 70°, about 40° to about 80°, about 40° to about 85°, about 50° to about 60°, about 50° to about 70°, about 50° to about 80°, about 50° to about 85°, about 60° to about 70°, about 60° to about 80°, about 60° to about 85°, about 70° to about 80°, about 70° to about 85°, or about 80° to about 85°. In some cases, the angle formed between the ridge and the bottom surface is about 5°, about 10°, about 20°, about 30°, about 40°, about 50°, about 60°, about 70°, about 80°, or about 85°. In some cases, the angle formed between the ridge and the bottom surface is at least about 5°, about 10°, about 20°, about 30°, about 40°, about 50°, about 60°, about 70°, or about 80°. In some cases, the angle formed between the ridge and the bottom surface is at most about 10°, about 20°, about 30°, about 40°, about 50°, about 60°, about 70°, about 80°, or about 85°.

In some embodiments, the microneedle section may also have a bottom surface which is lower than the bottom surface of the support substrate, e.g., the bottom surface of the microneedle section may protrude farther from the device compared to the bottom surface of the support substrate. In some cases, a bottom surface may overlap the base of the microneedles. In some cases, the bottom surface of the interior section may protrude by about 250 µm. In some cases, the bottom surface of the interior section may protrude by about 0 µm, 50 µm, 100 µm, 150 µm, 200 µm, 250 µm, 300 µm, 350 µm, 400 µm, or 450 µm. In some cases, the protruding bottom surface of the interior section may increase or maintain surface tension of a tissue such as skin when the device is applied to the tissue.

Figure 3:
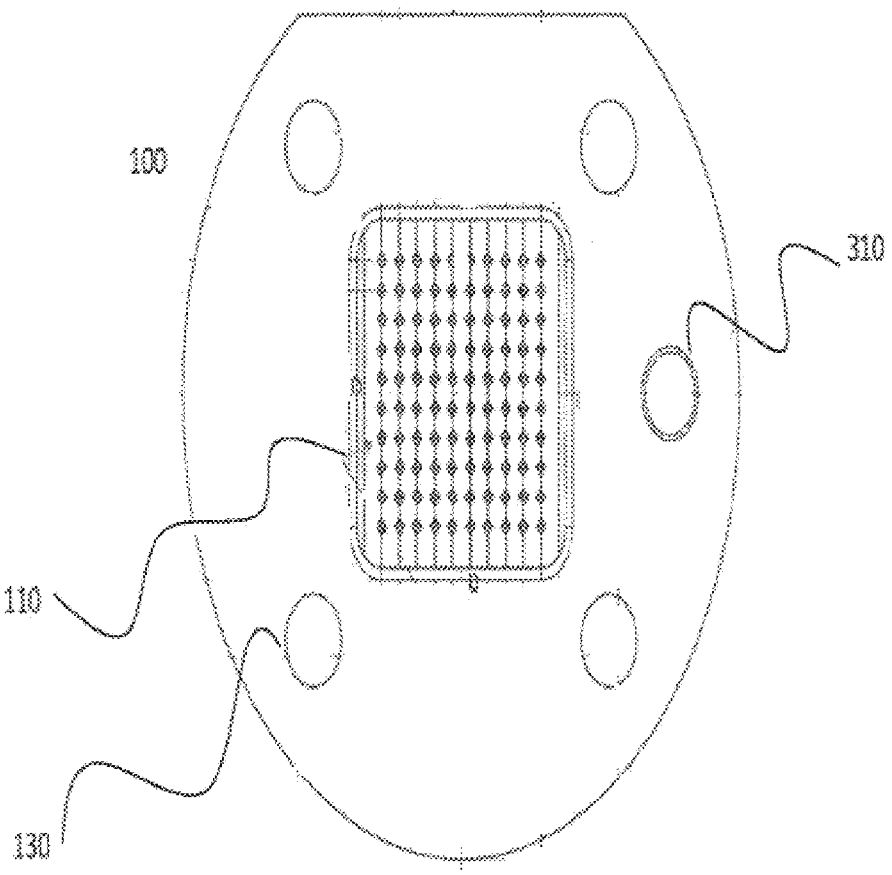
FIG. 3 illustrates a front view of a microneedle device as described herein.

In some embodiments, the support substrate, 130, may be formed of the same material as the microneedle section and the microneedles. The support substrate may be thicker than the interior section. In some cases, the peripheral section comprises a fiducial marker. FIG. 3 provides a front view of microneedle device 100, with a fiducial marker, 310.

In some embodiments, a device of the present disclosure may be manufactured using a mold. In some cases, a device may be manufactured by displacing a resin (e.g., polyolefin resin) into a mold for the device. The mold may comprise a plurality of cavities for forming a plurality of microneedles, cavity for forming an interior section comprising the plurality of microneedles; and one or more cavities for forming one or more peripheral sections adjacent to the interior section, wherein a width of the interior section is less than a width of the peripheral sections. In some cases, the polyolefin resin may generate the plurality of microneedles prior to generating the interior section. In some cases, the molded resin may be plasma treated to modify a surface.

In some embodiments, a device of the present disclosure may be manufactured using injection molding. In some cases, a device may be manufactured by injecting heated (e.g. molten) material (e.g. a polyolefin resin described herein) into a mold of the device. The mold may comprise a plurality of cavities for forming a plurality of microneedles, cavity for forming an interior section comprising the plurality of microneedles, and one or more cavities for forming one or more peripheral sections adjacent to the interior section, wherein a width (e.g. depth and/or thickness) of the interior section is less than a width of the peripheral sections. In some cases, the heated material may generate the plurality of microneedles prior to generating the interior or microneedle section.

In some cases, the entire device may be plasma treated, while in other cases a portion of the device, for example the microneedles, is plasma treated. In some cases, the method of plasma treating the device or portion thereof comprises the steps of providing the device or portion thereof, placing the device or portion thereof into the plasma vacuum chamber, closing the plasma vacuum chamber creating a sufficient vacuum seal, evacuating all of the gas present in the chamber, pumping a plasma treatment gas into the plasma vacuum chamber to a desirable pressure, enabling the generation of gas plasma for a desirable period of time at a desirable power, evacuating the chamber of the plasma treated gas and removing the device or portion thereof.

In some cases, the entire device may be excimer laser treated, while in other cases a portion of the device, for example the microneedles, is excimer laser treated. In some cases, the method of excimer laser treating the device or portion thereof comprises the steps of providing the device or portion thereof, placing the device or portion thereof into the excimer laser treating chamber, closing the excimer laser treating chamber, evacuating all of the gas present in the chamber, pumping a suitable excimer laser treatment gas into the excimer laser treating chamber to provide sufficient absorption of radiative laser energy by the device or portion thereof, enabling the radiative emission of an excimer laser for a desirable period of time at a desirable power, evacuating the excimer laser treatment gas and removing the device or portion thereof.

In some cases, one or more probes of the plurality of probes are attached to one or more microneedles of the plurality of microneedles. The probes may be covalently or non-covalently attached. In some cases, the probes are attached via a linker or a spacer. In some cases, the probes are attached to a microneedle as to achieve a maximum packing density on the surface of the microneedle.

Probes

In some embodiments, the microneedles comprise probes that can bind and extract biomarkers from a tissue. A plurality of probes can be attached to a microneedle of the disclosure. In some cases, the probes comprise polynucleotides (e.g., DNA, RNA, cDNA, cRNA, etc.). Often the polynucleotide probes are designed to bind or hybridize a specific polynucleotide biomarker. This disclosure also provides methods and devices for detecting peptide or protein biomarkers. In these embodiments, the probes attached to the microneedles can specifically recognize and bind to target peptides or proteins of interest. The probes can be any substance capable of binding to a specific peptide or protein biomarker. They can be, e.g., a protein (e.g., an antibody, antigen, or fragment thereof), carbohydrate, or a polynucleotide. The polynucleotide may possess sequence specificity for the biomarker, e.g., by having a complementary sequence.

In some embodiments, the probes to be used often depend on the biomarker or biomarkers to be detected. Thus, depending the nature and number of biomarkers to be detected, the number of probes immobilized to a microneedle can be 2, 3, 4, 5, 6, 7, 8, 9, 10, or more. In some cases, the total number of probes immobilized to a microneedle can be from about 1 probe to about 1,000 probes, from about 1 probe to about 10,000 probes, from about 1 probe to about 100,000 probes, from about 1 probe to about 1,000,000 probes, from about 1 probe to about 10,000,000, from about 1 probe to about 100,000,000 probes, from about 1,000 probes to about 100,000,000 probes, from about 10,000 probes to about 100,000,000 probes, or from about 10,000,000 probes to about 100,000,000 probes. In some cases, the total number of probes in a microneedle is at least about 10, about 20, about 50, about 100, about 500, about 1000, about 10000, about 100000, about 1,000,000, about 10,000,000, or about 100,000,000 probes. In some cases, the total number of probes in a microneedle is less than about 10, about 100, about 1000, about 10000, about 100000, about 1,000,000, about 10,000,000, or about 100,000,000 probes.

In some embodiments, a probe for the biomarker can be immobilized to multiple microneedles in the device of the disclosure, particularly for detection of a biomarker of low concentration, as described further herein. In some cases, a single microneedle comprises multiple different probes capable of binding or detecting the same biomarker. In some cases, a single microneedle comprises at least 2 different probes, at least 3 different probes, at least 4 different probes, at least 6 different probes, at least 8 different probes, at least 10 different probes, at least 15 different probes, at least 20 different probes, or at least 50 different probes. In some cases, the same microneedle comprises more than 50 different types of probes for the same biomarker.

In some cases, the same microneedle comprises a plurality of different probes. The different probes can be specific for the same biomarker or for a different biomarker. A microneedle can comprise at least 2 different probes, at least 10 different probes, at least 100 different probes, at least 200 different probes at least 500 different probes, at least 1,000 different probes, at least 5,000 different probes, or at least 10,000 different probes.

In some cases, the individual probes of the plurality of probes are identical (e.g., identical copies of the same polynucleotide or antibody). In some embodiments, a microneedle can be associated with numerous copies of the same probe (e.g., greater than 2, 5, 10, 50, 100, 1000, 5000, 7500, 10000, or 50000 copies of the same probe). For example, a microneedle can comprise a plurality of copies of a polynucleotide probe designed to hybridize the same polymorphism or biomarker. In some cases, a microneedle may comprise a plurality of copies of an antibody probe designed to bind the same epitope.

In some cases, a probe may bind to a class of biomarkers, for example mRNAs. A probe which binds to mRNAs may comprise a polynucleotide with a homopolymeric sequence or a polynucleotide that comprises a homopolymeric sequence. In some cases, the probe comprises one or more thymine residues. For example, in some cases, the probe comprises at least 1, at least 5, at least 10, at least 20, at least 25, at least 30, at least 40, at least 50, at least 100, or at least 200 thymine residues (e.g., a thymidine residue). In some cases, the probe binds to a poly-A tail of an mRNA molecule. In some cases, the probe comprises a homopolymeric sequence. In these cases, the homopolymeric sequence is configured to bind to a complementary homopolymeric sequence. In some cases, a probe comprises a sequence of thymines which bind to the poly A tails of the mRNAs. A probe may comprise any fragment of a sequence of consecutive thymines. In some embodiments, the sequence of consecutive thymines comprises about 250 consecutive thymines. In some embodiments, the sequence of consecutive thymines comprises about 200 consecutive thymines. In some embodiments, the sequence of consecutive thymines comprises about 150 consecutive thymines. In some embodiments, the sequence of consecutive thymines comprises about 100 consecutive thymines. In some embodiments, the sequence of consecutive thymines comprises about 50 consecutive thymines. In some embodiments, the sequence of consecutive thymines comprises about 50 and 250 consecutive thymines. In some cases, a probe may comprise thymines interspersed with other bases.

In some cases, a microneedle comprises polynucleotide probes. The probes may be designed to detect different biomarkers (e.g. nucleic acid molecules, proteins) associated with the same disease, disorder or condition. In some cases, a first probe may recognize a polymorphism (e.g., DNA polymorphism, RNA polymorphism) associated with a disease and a second probe may recognize a different polymorphism associated with the same disease. For example, a first nucleic acid probe on a microneedle can be designed to detect a first polymorphism of an RNA biomarker associated with onchocerciasis, a skin condition. A second nucleic acid probe on a microneedle can be designed to detect a second polymorphism of an RNA biomarker associated with onchocerciasis. A polymorphism can be, for example, a single nucleotide polymorphism (SNP). Genetic and genomic variations can comprise a single SNP or a plurality of SNPs. SNPs can occur at a single locus, or at many loci. Individuals who carry a particular SNP on an allele at one locus can predictably carry additional SNPs at other loci. A correlation of SNPs can provide an association between alleles predisposing an individual to disease or condition. In some cases, the different polynucleotide probes are designed to detect different biomarkers associated with different conditions. For example, one probe may detect a biomarker of a disease (e.g. polynucleotides), while the other probe may detect a housekeeping gene or gene product (e.g. polypeptides). In some cases, the microneedles are attached to polynucleotides, polypeptides, or a mixture of polynucleotides and polypeptides. In some cases, the probes may comprise a negative charge. In some cases, a plurality of probes may comprise a residual negative charge. In some cases, the microneedles of the devices described herein are packed with probes at the maximum packing density for the microneedle. The residual negative charge generated from a maximum-packed microneedle can be strong enough to prevent the packed probes from non-specific binding to biomarkers that are not of interest.

In some cases, a microneedle can also be associated with a plurality of different protein or antibody probes. For example, a first antibody probe on a microneedle can be designed to detect a first epitope of an antigen associated with, for example, a skin cancer. A second antibody probe can be designed to detect a second epitope associated with the antigen. Or, in some cases, the second antibody probe can detect an epitope associated with a different skin condition and/or different antigen.

In some cases, the present disclosure provides a microneedle device comprising a set of microneedles, wherein each microneedle in the set comprises identical probes or set of probes. In some embodiments, an identical probe is attached to a plurality of microneedles of a device. An identical probe can be attached to, for example, about 1% of the microneedles, about 5% of the microneedles, about 10% of the microneedles, about 50% of the microneedles, about 90% of the microneedles, about 95% of the microneedles, or about 100% of the microneedles. In some embodiments, an identical probe is attached to no greater than 5% of the microneedles, no greater than 10% of the microneedles, no greater than 25% of the microneedles, no greater than 50% of the microneedles, no greater than 95% of the microneedles, or no greater than 99% of the microneedles.

In some cases, a plurality of microneedles may comprise at least one microneedle attached to a first probe and at least one microneedle attached to a second probe that is different from the first probe. For example, as described herein, the first probe may be a polynucleotide or polypeptide (e.g., antibody, protein) that specifically binds a biomarker of a disease or disorder and the second probe may be a polynucleotide or polypeptide that specifically binds a different biomarker associated with the same disease or disorder. In some cases, the first probe may be a polynucleotide or polypeptide (e.g., antibody, protein) that specifically binds a biomarker of a disease or disorder and the second probe may be a polynucleotide or polypeptide that specifically binds a different biomarker associated with a different disease, disorder, or condition. In some cases, the different disease, condition, or disorder is associated with the same organ. For example, the first probe may be associated with a first disease, disorder, or condition associated with skin; and the second probe may be associated with a second disease, disorder, or condition associated with skin or eye. In some cases, the device may comprise an array of microneedles, wherein each microneedle comprises a probe that detects a biomarker associated with a different disease, disorder, or condition associated with the same organ. The array of microneedles may comprise greater than 2, 3, 4, 5, 6, 7, 8, 9, 10, 20, 30, 40, 50, 75, 100, 150, 200, 500, or 1000 microneedles associated with different diseases, disorders, or conditions. In some cases, the different diseases, disorders, or conditions are associated with different organs (e.g., greater than 1, 2, 3, 4, 5, 6, 7, 8, 9, 10, 15, or 20 organs).

In some cases, the microneedle device comprises a plurality of arrays of microneedles; often, the plurality of arrays of microneedles are suitable for multiplexed reactions. In some cases, the plurality of arrays comprises two or more arrays of microneedles, wherein the arrays are designed to detect a different biomarker. In some cases, a first array of microneedles may be designed to detect a biomarker associated with disease, disorder, or condition, and the second array of microneedles is designed to detect a different biomarker associated with the same disease, disorder, or condition. In some cases, a first array of microneedles may be designed to detect a biomarker associated with disease, disorder, or condition, and a second array of microneedles may be designed to detect a different biomarker associated with a different disease, disorder, or condition. In some cases, a first array of microneedles may be designed to detect a plurality of biomarkers associated with a disease, disorder, or condition; and a second array of microneedles may be designed to detect a plurality of biomarkers associated with a different disease, disorder, or condition. In some cases, the second array of microneedles may be designed to detect control biomarkers (e.g., housekeeping genes), either positive controls or negative controls.

In some embodiments, the probes are covalently attached to the microneedles. In some embodiments, the probes are attached to the microneedles at about 70%, 75%, 80%, 85%, 90%, 95%, 96%, 97%, 98%, 99%, or 100% of a maximum packing density. A maximum packing density may be determined by the chemical structure of the microneedle surface. In some cases, a high density of probes may decrease non-specific binding. For example, a high density of polynucleotide probes will discourage non-specific polynucleotide binding due to the residual negative charge. In some cases, the microneedles may be treated to facilitate a high density of probe attachment. For example, the microneedles may be plasma treated. The plasma treatment may comprise treatment with an oxygen, nitrogen, or carbon dioxide plasma to modify the surface.

Microneedles

A microneedle can have a plurality of shapes, for example, a microneedle can be round, conical, triangular, square, rectangular, pentagonal, hexagonal, heptagonal, octagonal, pyramidal, or any other suitable shape. A microneedle can be a sharp microneedle, a blunt microneedle, or any combination thereof. For example, a device of the present disclosure comprising a plurality of sharp microneedles can be used to penetrate the skin of a subject thereby contacting the probe(s) on the microneedle with, for example, a biomarker. A sharp microneedle can be used to disrupt tissue of a biological sample, such as a layer of cells or the outer membrane of a cell. A blunt microneedle can be used to touch the surface of the skin of a subject thereby contacting the microneedle with, for example, a cell-surface biomarker on the skin. In some cases, the present disclosure provides microneedle devices that comprise microneedles with different shapes (e.g., sharp and blunt microneedles). In some cases, the microneedles may be solid rather than hollow.

In some cases, the present disclosure provides microneedle devices in which all needles have a same shape. In some cases, all microneedles on a device have the same shape and dimensions, within a 5%, 4%, 3%, 2%, 1.5%, 1%, 0.75%, 0.5%, or 0.25% error. In some cases, no more than three microneedles of a plurality of microneedles do not meet the height tolerance. For example, if a desired microneedle height is 950 µm, then a height tolerance may be no less than 600 µm in length and no more than 1050 µm in length.

In some embodiments, a microneedle may have a shape that allows non-specifically bound material to be wiped off needle upon microneedles' exit from skin. In some cases, the non-specifically bound material may be wiped off via shearing forces generated as the microneedle is drawn through the skin.

Figure 4:
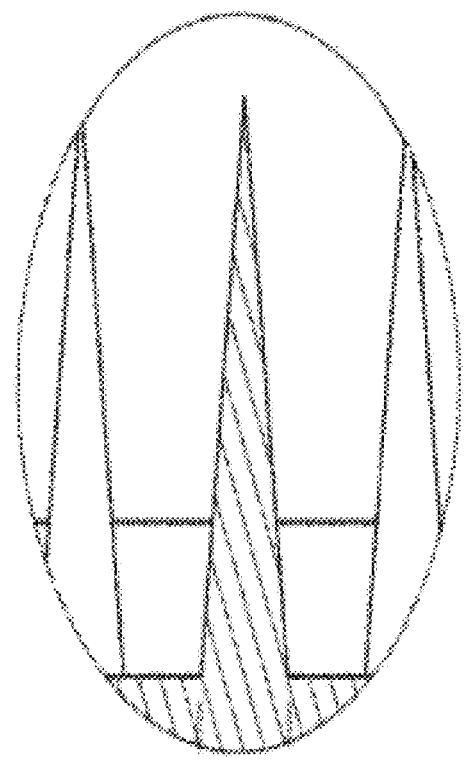
FIG. 4 illustrates a microneedle of a microneedle device as described herein.

In some embodiments, while the needle-shaped microneedles can be blunt-pointed objects, they are preferably sharp-pointed objects. In some embodiments, the microneedles have a circular cone structure with a diameter of the base generally in the range of 10 µm to 500 µm, preferably in the range of 20 µm to 200 µm. FIG. 4 illustrates a surface of a device of the present disclosure with a plurality of microneedles wherein the diameter of the base is less than 10 mm in width.

In some embodiments, a microneedle of the disclosure can comprise a plurality of different diameters or base widths. The shape of the base of a microneedle can be, for example, round, rectangular, triangular, square, pentagonal, hexagonal, heptagonal, or other geometric shape. A microneedle of the disclosure can have a diameter or base width that is no greater than 500 µm, no greater than 400 µm, no greater than 300 µm, no greater than 200 µm, no greater than 100 µm, no greater than 50 µm, no greater than 40 µm, no greater than 30 µm, no greater than 20µηι, no greater than 10 µm, no greater than 1000 nm, no greater than 900 nm, no greater than 800 nm, no greater than 700 nm, no greater than 600 nm, no greater than 500 nm, no greater than 400 nm, no greater than 300 nm, no greater than 200 nm, or no greater than 100 nm.

In some cases, a microneedle with a circular cone structure may have an angle of the edge of the cone to the base of the cone from 70° to about 90°, from 71° to 89°, from 72° to 88°, from 73° to 86°, from 73° to 84°, from 73° to 80°, from 74° to 78°, from 74° to 76°, or from 75.5° to 76°. In some cases a microneedle with a circular cone structure may have an angle from the edge of the cone to the base of the cone of about 73°, 73.25°, 73.5°, 73.75°, 74°, 74.25°, 74.5°, 74.75°, 75°, 75.25°, 75.5°, 75.75°, 76°, 76.25°, 76.5°, 76.75°, or 77°. In some cases a microneedle with a circular cone structure may have an angle of the edge of the cone to the base of less than 73°, 73.25°, 73.5°, 73.75°, 74°, 74.25°, 74.5°, 74.75°, 75°, 75.25°, 75.5°, 75.75°, 76°, 76.25°, 76.5°, 76.75°, or 77°.

In some embodiments, the substrate and the microneedles of the arrays can be made of various biodegradable or non-biodegradable materials. Examples of the material for the microneedles or substrate include poly(methyl methacrylate), silicon, silicon dioxide, ceramic, metal (such as stainless steel, titanium, nickel, molybdenum, chromium, and cobalt), and synthetic or natural resin material. Some embodiments use a biodegradable polymer such as polylactic acid, polyglycolide, polylactic acid-co-polyglycolide, pullulan, capronolactone, polyurethane or polyanhydride. In some other embodiments, a non-degradable material is employed to fabricate the microneedle array, e.g., a polymer polycarbonate, a synthetic or natural resin material such as polymethacrylic acid, ethylenevinylacetate, polytetrafluoroethylene, polysulfone, or polyoxymethylene. In some embodiments, the microneedles may be non-dissolvable. In some cases, the microneedle is fabricated with a thermoplastic polymer.

In some embodiments, the substrate and the microneedles of the arrays can be made of various thermoplastic polymers. Non-limiting examples of thermoplastic polymers include acrylic polymers, such as poly(methyl methacrylate) (PMMA), nylon, polyethylene, polypropylene, polystyrene, polyvinyl chloride, or Teflon. In some cases, a device of the present disclosure is fabricated with a thermoplastic polymer selected from the group consisting of polycarbonate, poly(methyl methacrylate), polyethylene and polypropylene.

Non-limiting examples of non-degradable polymers include, for example, silicone, hydrogels such as crosslinked poly(vinyl alcohol) and poly(hydroxy ethylmethacrylate), ethylene-vivyl acetate, acyl substituted cellulose acetates and alkyl derivatives thereof, partially and completely hydrolyzed alkylene-vinyl acetate copolymers, unplasticized polyvinyl chloride, crosslinked homo- and copolymers of polyvinyl acetate, crosslinked polyesters of acrylic acid and/or methacrylic acid, polyvinyl alkyl ethers, polyvinyl fluoride, polycarbonate, polyurethane, polyamide, polysulphones, styrene acrylonitrile copolymers, crosslinked poly (ethylene oxide), poly(alkylenes), poly(vinyl imidazole), poly(esters), poly(ethylene terephthalate), polyphosphazenes, and chlorosulphonated polyolefines, and combinations thereof. In some embodiments the polymer comprises ethylene vinyl acetate.

Further non-limiting examples of biodegradable polymers include polyesters such as 3-hydroxypropionate, 3-hydroxybutyrate, 3-hydroxyvalerate, 3-hydroxycaproate, 3-hydroxyheptanoate, 3-hydroxyoctanoate, 3-hydroxynonanoate, 3-hydroxydecanoate, 3-hydroxyundecanoate, 3-hydroxydodecanoate, 4-hydroxybutyrate, 5-hydroxyvalerate, polylactide or polylactic acid including poly(d-lactic acid), poly(1-lactic acid), poly(d,1-lactic acid), polyglycolic acid and polyglycolide, poly(lactic-co-glycolic acid), poly (lactide-co-glycolide), poly(ε-caprolactone) and polydioxanone. Polysaccharides including starch, glycogen, cellulose and chitin can also be used as biodegradable materials.

In some embodiments the substrate and the microneedles of the arrays can be made of a polyolefin resin. Examples of polyolefin resins include thermoplastic polyolefins: polyethylene (PE), polypropylene (PP), polymethylpentene (PMP), and polybutene-1 (PB-1). Further examples of polyolefin resins include polyolefin elastomers (POE): polyisobutylene (PIB), ethylene propylene rubber (EPR), and ethylene propylene diene monomer (M-class) rubber (EPDM rubber). In some cases, the polyolefin resin may be a Cyclo Olefin Polymer such as Zeonor or Zeonex. In some cases, the Zeonor is Zeonor 1020R, Zeonor 690R or Zeonor 1060R.

In some embodiments, the microneedles employed in the present disclosure have a length (height) that is typically in the range of 20 μm to 1 mm, preferably in the range of 50 μm to 500 μm. The height of the needles may range from about 400 μm to about 1000 μm.

A microneedle device of the present disclosure may comprise any number of microneedles. In some embodiments, a device of the present disclosure comprises at least 1 microneedle, at least 100 microneedles, at least 200 microneedles, at least 300 microneedles, at least 400 microneedles, at least 500 microneedles, at least 1000 microneedles, at least 3000 microneedles, or at least 5000 microneedles.

In some embodiments, a device of the present disclosure comprises at most 10000 microneedles, at most 5000 microneedles, at most 2500 microneedles, at most 2000 microneedles, at most 1000 microneedles, at most 500 microneedles, at most 400 microneedles, at most 300 microneedles, at most 100 microneedles, at most 90 microneedles, at most 50 microneedles, at most 40 microneedles, at most 30 microneedles, at most 20 microneedles, at most 15 microneedles, at most 10 microneedles, at most 9 microneedles, at most 8 microneedles, at most 7 microneedles, at most 6 microneedles, at most 5 microneedles, at most 4 microneedles, at most 3 microneedles, at most 2 microneedles, or 1 microneedle.

In some embodiments, a device of the disclosure comprises from about 1 microneedle to about 100 microneedles, from about 1 microneedle to about 200 microneedles, from about 1 microneedle to about 1000 microneedles, from about 10 microneedles to about 200 microneedles, from about 50 microneedles to about 150 microneedles, or from about 1 microneedle to about 5000 microneedles.

In some embodiments, a device of the disclosure comprises 100 microneedles. In some embodiments, a device of the disclosure comprises from 90 to 110 microneedles. In some embodiments, a device of the disclosure comprises from 80 to 120 microneedles. In some embodiments, a device of the disclosure comprises 50 to 150 microneedles.

In some embodiments, for devices containing a plurality of microneedles, the microneedles can be present on the devices in rows. In some embodiments, the rows can be spaced at virtually equal intervals to the space of the needles aligned in the row. In some embodiments, the rows can be spaced at irregular intervals.

In some embodiments the density of the microneedles in the device may be at least about $10/cm^2$, about $15/cm^2$, about $20/cm^2$, about $25/cm^2$, about $30/cm^2$, about $35/cm^2$, about $40/cm^2$, about $45/cm^2$, about $50/cm^2$, about $55/cm^2$, about $60/cm^2$, about $65/cm^2$, about $70/cm^2$, about $75/cm^2$, about $80/cm^2$, about $85/cm^2$, about $90/cm^2$, about $95/cm^2$, about $100/cm^2$, about $110/cm^2$, about $120/cm^2$, about $130/cm^2$, about $140/cm^2$, about $150/cm^2$, or about $200/cm^2$. In some embodiments the density of the microneedles in the device may be less than about $10/cm^2$, about $15/cm^2$, about $20/cm^2$, about $25/cm^2$, about $30/cm^2$, about $35/cm^2$, about $40/cm^2$, about $45/cm^2$, about $50/cm^2$, about $55/cm^2$, about $60/cm^2$, about $65/cm^2$, about $70/cm^2$, about $75/cm^2$, about $80/cm^2$, about $85/cm^2$, about $90/cm^2$, about $95/cm^2$, about $100/cm^2$, about $110/cm^2$, about $120/cm^2$, about $130/cm^2$, about $140/cm^2$, about $150/cm^2$, or about $200/cm^2$.

In some embodiments, a distance between the center of two microneedles on a device of the disclosure can be calculated to determine a density of the microneedles in the device. In some embodiments, the center-to-center distance between two microneedles can be less than 1000 μm, less than 900 μm, less than 800 μm, less than 700 μm, less than 600 μm, less than 500 μm, less than 400 μm, less than 300 μm, less than 200 μm, or less 100 μm. In some embodiments, the center-to-center distance between two microneedles can be no greater than 100 μm, no greater than 200 μm, no greater than 300 μm, no greater than 400 μm, no greater than 500 μm, no greater than 600 μm, no greater than 700 μm, no greater than 800 μm, no greater than 900 μm, or no greater than 1000 μm.

In some embodiments, microneedles of the disclosure can comprise a plurality of different diameters or base widths. The shape of the base of a microneedle can be, for example, round, rectangular, triangular, square, pentagonal, hexagonal, heptagonal, or other geometric shape. A microneedle of the disclosure can have a diameter or base width that is no greater than 500 μm, no greater than 400 μm, no greater than 300 μm, no greater than 200 μm, no greater than 100 μm, no greater than 50 μm, no greater than 40 μm, no greater than 30 μm, no greater than 20 μm, no greater than 10 μm, no greater than 1000 nm, no greater than 900 nm, no greater than 800 nm, no greater than 700 nm, no greater than 600 nm, no greater than 500 nm, no greater than 400 nm, no greater than 300 nm, no greater than 200 nm, or no greater than 100 nm.

Kits

In some embodiments, the present disclosure provides kits comprising a microneedle device as described herein. In some cases, a kit may comprise a microneedle device as described herein, wherein the microneedle device comprises a recess behind the microneedle region, and an applicator which fits within the recess. In some cases, the applicator is a mechanical applicator. In some cases, the microneedle device comprises a microneedle region comprising a plurality of microneedles protruding from a front surface of a microneedle base substrate, the microneedle base substrate also comprising a back surface, the back surface comprising a recess directly behind at least a portion of the microneedle region; and a support substrate adjacent to at least one side of the microneedle base substrate, the support substrate connected to or integral with the microneedle base substrate.

Methods

In some embodiments, the present disclosure provides a method of obtaining a biological sample from a tissue, such as the skin of a subject. A subject can be of any age. For example, a subject can be an elderly adult, an adult, an adolescent, a pre-adolescent, a child, a toddler, or an infant. A subject can be a mammal, a bird, a fish, a reptile, or an amphibian. Non-limiting examples of a subject include humans, primates, dogs, cats, horses, pigs, and mice. A subject may be a patient. In some embodiments, the subject is a human.

In some cases, the method comprises contacting a device of the present disclosure with a tissue of a subject. In some cases, the subject may contact the device with their tissue, for example by applying the device to their skin. In some cases, the device may be applied to a subject's tissue by someone else. In some cases, the tissue may be skin, and the skin may be cleaned prior to application of the device.

In some cases, the method comprises contacting a device of the present disclosure with a tissue, such as skin, of a subject. In some cases, the tissue is an in situ tissue. In some cases, the tissue is a biopsy. In some cases, the tissue is skin tissue. Pressure may be applied to the device, thus causing the microneedles to penetrate the tissue. In some cases, pressure is applied by hand, for example thumb pressure. In other cases, pressure may be applied by an applicator. The pressure may be less than about 1 N/mm2, 5 N/mm2, 10 N/mm2, 50 N/mm2, 100 N/mm2, 200 N/mm2, 200 N/mm2, or within a range of about 1 N/mm2 and about 200 N/mm2. The applicator may be a manual applicator, or a mechanical or electronic applicator which provides a uniform pressure. In some cases, one end of the applicator has a width that is less than the width of the recess behind the microneedle section. The surface of the device distal to the microneedles may be referred to as the back surface. The pressure may be applied to the entire back surface, or may be concentrated on the back surface of the interior section of the device 120.

In some embodiments, the microneedle device may be retained in the tissue for up to 1 minute, 2 minutes, 3 minutes, 4 minutes, 5 minutes, 6 minutes, 7 minutes, 8 minutes, 9 minutes, 10 minutes, 12 minutes, 14 minutes, 16 minutes, 18 minutes, 20 minutes, 22 minutes, 24 minutes, 26 minutes, 28 minutes, or 30 minutes. The residence time of the microneedles inside the tissue allows the probes to contact and bind to biomarkers, for example nucleic acid molecules, in the tissue. In some cases, the residence time of microneedles inside the tissue may be optimized for a particular tissue, biomarker or probe. For example, a biomarker such as an RNA biomarker may start to degrade after a given period of time, and thus a residence time long enough to allow binding but short enough to minimize degradation would be preferred. In some cases, a residence time of about 1 minute to about 10 minutes may be preferred for RNA biomarkers. In some cases, a residence time of less than 5 minutes may be preferred for RNA biomarkers. In some cases, a residence time of about 5 minutes may be preferred for RNA biomarkers. In some cases, a residence time of no more than 10 minutes may be preferred for RNA biomarkers. In some cases, a residence time of about 2 minutes to about 9 minutes may be preferred for RNA biomarkers. In some cases, a residence time of about 3 minutes to about 8 minutes may be preferred for RNA biomarkers. In some cases, a residence time of about 4 minutes to about 7 minutes may be preferred for RNA biomarkers. In some cases, a residence time of about 5 minutes to about 6 minutes may be preferred for RNA biomarkers. In some cases, a residence time of about 5 minutes to about 7 minutes may be preferred for RNA biomarkers. In some cases, a residence time of about 5 minutes to about 8 minutes may be preferred for RNA biomarkers. In some cases, a residence time of about 5 minutes to about 9 minutes may be preferred for RNA biomarkers. In some cases, a residence time of about 5 minutes to about 10 minutes may be preferred for RNA biomarkers.

In some cases, the optimal residence time of the microneedles inside the tissue is determined by the cycle threshold (Ct) for detection of a target biomarker. In some cases, for RNA biomarkers, the Ct is lowest at about 5 minutes. In some cases, for RNA biomarkers, the Ct of a sample collected after a residence time of 10 minutes is higher than the Ct of a sample collected after a residence time of 5 minutes. In some cases, an increase of Ct from a minimum Ct indicates degradation of the sample may be occurring.

In some cases, the optimal residence time generates a high-quality biomarker sample. In some cases, for RNA biomarkers, the quality of the RNA sample is determined by a ratio of larger RNA fragments (e.g. RNA fragments comprising about 700 bases or more) comprised in the RNA sample to smaller RNA fragments (e.g. fragments comprising about 150 bases to about 200 bases) comprised in the RNA sample. In some cases, a residence time of no more than 10 minutes generates an RNA sample wherein the RNA sample comprises a population of large RNA fragments, e.g. RNA fragments comprising about 700 bases or more, and a population of small RNA fragments, e.g. fragments comprising about 150 bases to about 200 bases, and wherein a ratio of the population of large RNA fragments, e.g. RNA fragments comprising about 700 bases or more, and the small RNA fragments, e.g. fragments comprising about 150 bases to about 200 bases, is greater than 1. In some cases, a residence time of no more than 9 minutes generates an RNA sample wherein the RNA sample comprises a population of large RNA fragments, e.g. RNA fragments comprising about 700 bases or more, and a population of small RNA fragments, e.g. fragments comprising about 150 bases to about 200 bases, and wherein a ratio of the population of large RNA fragments, e.g. RNA fragments comprising about 700 bases or more, and the small RNA fragments, e.g. fragments comprising about 150 bases to about 200 bases, is greater than 1. In some cases, a residence time of no more than 8 minutes generates an RNA sample wherein the RNA sample comprises a population of large RNA fragments, e.g. RNA fragments comprising about 700 bases or more, and a population of small RNA fragments, e.g. fragments comprising about 150 bases to about 200 bases, and wherein a ratio of the population of large RNA fragments, e.g. RNA fragments comprising about 700 bases or more, and the small RNA fragments, e.g. fragments comprising about 150 bases to about 200 bases, is greater than 1. In some cases, a residence time of no more than 7 minutes generates an RNA sample wherein the RNA sample comprises a population of large RNA fragments, e.g. RNA fragments comprising about 700 bases or more, and a population of small RNA fragments, e.g. fragments comprising about 150 bases to about 200 bases, and wherein a ratio of the population of large RNA fragments, e.g. RNA fragments comprising about 700 bases or more, and the small RNA fragments, e.g. fragments comprising about 150 bases to about 200 bases, is greater than 1. In some cases, a residence time of no more than 6 minutes generates an RNA sample wherein the RNA sample comprises a population of large RNA fragments, e.g. RNA fragments comprising about 700 bases or more, and a population of small RNA fragments, e.g. fragments comprising about 150 bases to about 200 bases, and wherein a ratio of the population of large RNA fragments, e.g. RNA fragments comprising about 700 bases or more, and the small RNA fragments, e.g. fragments comprising about 150 bases to about 200 bases, is greater than 1. In some cases, a residence time of no more than 5 minutes generates an RNA sample wherein the RNA sample comprises a population of large RNA fragments, e.g. RNA fragments comprising about 700 bases or more, and a population of small RNA fragments, e.g. fragments comprising about 150 bases to about 200 bases, and wherein a ratio of the population of large RNA fragments, e.g. RNA fragments comprising about 700 bases or more, and the small RNA fragments, e.g. fragments comprising about 150 bases to about 200 bases, is greater than 1. In some cases, a residence time of no more than 4 minutes generates an RNA sample wherein the RNA sample comprises a population of large RNA fragments, e.g. RNA fragments comprising about 700 bases or more, and a population of small RNA fragments, e.g. fragments comprising about 150 bases to about 200 bases, and wherein a ratio of the population of large RNA fragments, e.g. RNA fragments comprising about 700 bases or more, and the small RNA fragments, e.g. fragments comprising about 150 bases to about 200 bases, is greater than 1. In some cases, a residence time of no more than 3 minutes generates an RNA sample wherein the RNA sample comprises a population of large RNA fragments, e.g. RNA fragments comprising about 700 bases or more, and a population of small RNA fragments, e.g. fragments comprising about 150 bases to about 200 bases, and wherein a ratio of the population of large RNA fragments, e.g. RNA fragments comprising about 700 bases or more, and the small RNA fragments, e.g. fragments comprising about 150 bases to about 200 bases, is greater than 1. In some cases, a residence time of about 5 minutes generates an RNA sample wherein the RNA sample comprises a population of large RNA fragments, e.g. RNA fragments comprising about 700 bases or more, and a population of small RNA fragments, e.g. fragments comprising about 150 bases to about 200 bases, and wherein a ratio of the population of large RNA fragments, e.g. RNA fragments comprising about 700 bases or more, and the small RNA fragments, e.g. fragments comprising about 150 bases to about 200 bases, is greater than 1.

In some embodiments, after allowing a time for the probes to contact and bind the biomarkers, the device is removed from the tissue. Removal of the microneedles from the tissue may generate sheering pressures that remove non-specifically bound contaminants from the microneedles. In some cases, contaminants comprise any compound not intended for further genomic analysis.

In some embodiments, once removed from skin the device and extracted RNA biomarkers may be placed into a storage buffer, a transport buffer, or an analysis buffer. The device and extracted RNA biomarkers may be stored at −80° C., −20° C., −4° C., 4° C. or room temperature. Alternatively, the device may be placed into a buffer to dissociate the extracted RNA biomarkers from the device, and the extracted RNA biomarkers may be stored at −80° C., −20°

C., −4° C., 4° C. or room temperature. The extracted RNA biomarkers (with or without the device) may be sent to a laboratory for further analysis.

In some embodiments, the present disclosure provides a method for preparing a sample for genomic or transcriptomic analysis. The method may comprise, contacting a device of the present disclosure with skin of a subject, extracting nucleic acid biomarkers from the skin onto the device, washing the nucleic acid biomarkers from the device to produce a sample solution. The nucleic acids of the sample solution may be analyzed by polymerase chain reaction. In some cases, the extracted nucleic acids of the sample solution may be amplified and analyzed by next generation sequencing (NGS). NGS of extracted mRNAs may allow determination of gene expression in the contacted skin of the subject.

In some embodiments, the present disclosure provides a method of determining whether a skin lesion on a subject suffering thereof will be responsive to an autoimmune therapeutic drug. For example, the present disclosure provides a method of preparing a biological sample and identifying one or more autoimmune disease therapeutic drugs for a subject, the method comprising contacting skin of the subject with a microneedle device, wherein the microneedle device comprises one or more nucleic acid probes coupled to a solid microneedle and applying pressure to the microneedle device such that the microneedle device penetrates the skin of the subject. Extracted ribonucleic acid (RNA) molecules from the subject may be obtained by removing the microneedle device from the skin of the subject. Performing high throughput sequencing on the extracted RNA molecules can generate one or more sequence reads for the subject, which may be aligned with a known signature of sequence reads, wherein the known signature of sequence reads is associated with a positive response to the autoimmune disease therapeutic drug, thereby obtaining aligned sequence reads; and used to classify the subject as having a greater than 50%, 60%, 70%, 80% or 90% likelihood of positively responding to the autoimmune disease therapeutic drug by applying a trained algorithm to the aligned sequence reads. In some cases, the trained algorithm has a greater than 50%, 60%, 70%, 80% or 90% positive predictive value or greater than 50%, 60%, 70%, 80% or 90% negative predictive value. The autoimmune disease therapeutic drug may be an IL-17 mediated treatment, an IL-23 mediated treatment, an TNFα mediated treatment, or a combination thereof. The method may comprise the steps of extracting and sequencing mRNAs as described above, and comparing a gene signature of the lesion to known gene expression signatures using a trained algorithm, or analyzing the gene signature of the lesion using a trained algorithm. In some cases, the trained algorithm may have a greater than 50% positive predictive value or greater than 50% negative predictive value for predicting a greater than 50% likelihood of positive response to the autoimmune disease therapeutic drug. Comparing the gene expression signatures may allow classification of the contacted skin lesion as likely to be responsive to a treatment, wherein the treatment is either IL-17 mediated treatment, IL-23 mediated treatment, TNFα mediated treatment, or a combination thereof. Examples of autoimmune disease therapeutics include etanercept, infliximab, adalimumab, certolizumab, ustekinumab, secukinumab, ixekizumab, brodalumab, guselkumab, tildrakizumab, and risankizumab.

In some embodiments, the present disclosure provides a method for determining a likelihood that a subject with an autoimmune disease will respond to a therapeutic drug for an autoimmune disease the method comprising obtaining a biological sample from the subject; extracting one or more nucleic acid molecules from the biological sample; performing high throughput sequencing on the nucleic acid molecules to generate one or more sequence reads for the subject; and performing a genomic analysis on the sequence reads. The genomic analysis may comprise: determining an expression level of genes encoded by the sequence reads; comparing the expression level to a known positive-response genetic signature specific to a treatment for the autoimmune disease; and generating a treatment score from the comparison, wherein the treatment score is specific to a response to the treatment in the patient.

In some embodiments, the present disclosure provides a method of treating a skin lesion of a subject, the method comprising contacting the skin lesion with a device as described herein, extracting mRNAs from the skin lesion, using NGS to determine the gene expression signature, comparing the signature to known signatures or using a trained algorithm to select a treatment for the subject, and administering the selected treatment to the subject. In some cases, selecting a treatment comprises comparing an expression level of a known positive-response genetic signature specific to a treatment for the autoimmune disease.

This disclosure provides non-invasive and/or minimally invasive devices, methods, and systems that provide a subject specific dataset for disease diagnosis or guided clinical intervention. Further described herein are microneedle devices and methods and systems of using the same. For example, the methods of the invention described herein may comprise, in some embodiments, determining a gene expression profile, precise classification of a disease or condition, prospective guided therapy and/or clinical intervention for the diseases or conditions, retrospective analysis and modeling of past treatments, identifying an activated pathway for a disease or condition, or any combination thereof for one or more subjects. The microneedle devices described herein may provide precise, minimally and/or non-invasive sample collection that may be used in downstream analysis as described elsewhere herein, particularly in the aforementioned methods. Thus, the methods of the disclosure are useful for providing a means for practicing personalized medicine, wherein treatment is tailored to a subject based on characteristics of the disease in the subject (e.g. the gene expression profile of the subject suffering from the disease).

Generally, the microneedle devices may facilitate the collection of a subject's biological sample in situ for further analysis. In some cases, the microneedle device may comprise one or more microneedle features configured to puncture the skin or mucosal membrane of the subject. In some cases, the mucosal membrane may comprise oral mucosa, ophthalmic mucosal membranes, or any combination thereof. When a plurality of microneedles is present, the device may comprise a planar substrate which supports the microneedles. The substrate can be made of the same material as that of the microneedle. It can also be made of a different material. In some instances, the microneedles may further comprise probes adhered to the microneedle. These probes may be configured to bind to one or more biomarkers within a sample or tissue (e.g., skin) of a subject in such a manner as to permit extraction of the biomarker for further analysis. The extracted biomarkers may be analyzed, alone or in combination (e.g. generating a genetic signature or gene expression profile) to provide a diagnosis or prediction of a response to a drug or other therapeutic treatment with respect to the subject. Treating a Subject for a Mild, Moderate, or Severe Form of a Skin Condition In some cases, known treatments for known diseases may not be efficacious against a particular form of a disease as compared to an alternative form of the same disease. Differences between forms of the disease may arise as a result of varying genetic signatures from each particular form. In some embodiments, the methods described herein may provide targeted, specialized, personalized, or otherwise highly efficacious treatments or recommendation of treatments for subjects suffering from particular forms of known diseases.

In some embodiments, the present disclosure provides a method of determining whether a mild, moderate, or severe form of a skin condition of a subject suffering thereof will be responsive to a recommended treatment 600, as seen in FIG. 6. In some cases, the method of determining whether a skin condition of a subject suffering thereof will be responsive to recommended treatment may comprise: (a) obtaining ribonucleic acid (RNA) biomarkers from a subject (as described elsewhere herein) 602; (b) determining the likelihood that the skin condition will respond to a recommended treatment, wherein the recommended treatment comprises a 50% or less aggregate efficacy rate against known forms of the skin condition 604; and (c) treating the subject with the recommended treatment 606.

In some cases, the step of determining (i.e., step (b) of the above) may further comprise: (i) performing high throughput sequencing on the RNA biomarkers to generate one or more sequence reads for the subject; (ii) aligning the one or more sequence reads for the subject with a known signature of sequence reads, wherein the known signature of sequence reads is associated with a positive response to the recommended treatment, thereby obtaining aligned sequence reads; and (iii) classifying the subject as having a greater than 50% likelihood of positively responding to the recommended treatment by applying a trained algorithm to the aligned sequence reads, wherein the trained algorithm comprises a greater than 50% positive predictive value for predicting a greater than 50% likelihood of positive response to the recommended treatment. In some cases, the RNA biomarkers may comprise RNA molecules. In some instances, the RNA biomarkers are transcribed from one or more of the follow genes listed in Table 6, Table 12, or Table 13.

In some embodiments, the trained algorithm may further comprise a greater than 50% negative predictive value for predicting a greater than 50% likelihood of positive response to the recommended treatment. In some cases, the positive predictive value may be greater than 50%, 60%, 70%, 80% or 90%. In some instances, the negative predictive value may be or greater than 50%, 60%, 70%, 80% or 90%.

In some embodiments, the recommended treatment may comprise one or more autoimmune therapeutic drugs for an autoimmune disease or condition. In some cases, the autoimmune disease or condition may be psoriasis. In some instances, the recommended treatment may comprise etanercept, infliximab, adalimumab, certolizumab, ustekinumab, secukinumab, ixekizumab, brodalumab, guselkumab, tildrakizumab, risankizumab, or any combination thereof.
Recommending a Treatment by Positive Predictive Value In some cases, one or more subject suffering from a similar disease or condition may respond to a treatment with varying efficacy. In some embodiments, the efficacy may comprise a responder, non-responder, or adverse responder. In particular, genetic variability between subjects suffering from similar disease or condition may further stratify the varying efficacy of treatment intended to broadly treat a general form of the disease or condition. Aspects of the disclosure provided herein, in some embodiments, comprise a method of preparing a biological sample and identifying one or more therapeutic drugs to effectively tailor treatment to the particular genetic variant of a subject's disease or condition 608, as seen in FIG. 6B.

In some embodiments, this disclosure provides a method of treating a subject with an autoimmune disease of the skin (e.g., psoriasis) or recommending a treatment to such subject comprising collecting a sample comprising RNA derived from skin from the subject. Such collecting of a sample of RNA may involve use of a microneedle device or may involve lysis of a tissue biopsy or cell sample and extraction of nucleic acids (e.g., RNA) using an RNA extraction protocol. In some cases, the subject has not been administered the autoimmune therapeutic drug prior to collecting the sample. For example, in some embodiments, the subject has not been administered the autoimmune therapeutic drug greater than 1 day, 2 days, 3 days, 4 days, 5 days, 6 days, 7 days, 10 days, 15 days or 20 days prior to collecting the sample from the subject. In some cases, the method further comprises determining an expression level of at least one gene based on the RNA; predicting that a subject with the autoimmune disease of the skin will be responsive to the autoimmune therapeutic drug with a positive predictive value greater than 70%, a positive predictive value, a greater than 75% positive predictive value, a greater than 80% positive predictive value, a greater than 85% positive predictive value, a greater than 90% positive predictive value, or a greater than 95% positive predictive value based on the expression level of the at least one gene; and/or based on the predicting, treating the subject with the autoimmune therapeutic drug. In some cases, the positive predictive value is determined using a cohort of a specific size. For example, the method may have a positive predictive value provided herein when evaluated in a cohort of greater than 5, 10, 25, 50, 100, 150, 200, 250, 500, or 1000 patients.

In some embodiments, this disclosure provides a method of determining whether a skin lesion of a subject will be responsive to an autoimmune therapeutic drug comprising collecting a sample comprising RNA derived from skin from the subject. Such collecting of a sample of RNA may involve use of a microneedle device or may involve lysis of a tissue biopsy or cell sample and extraction of nucleic acids (e.g., RNA) using an RNA extraction protocol. In some cases, the subject has not been administered the autoimmune therapeutic drug prior to collecting the sample. For example, in some embodiments, the subject has not been administered the autoimmune therapeutic drug greater than 1 day, 2 days, 3 days, 4 days, 5 days, 6 days, 7 days, 10 days, 15 days or 20 days prior to collecting the sample from the subject. In some cases, the method further comprises converting the RNA into cDNA and determining an expression level of at least one gene based on the cDNA. In some cases, the method further comprises predicting that a subject with the skin lesion will be responsive to the autoimmune therapeutic drug with a positive predictive value greater than 70%, a positive predictive value, a greater than 75% positive predictive value, a greater than 80% positive predictive value, a greater than 85% positive predictive value, a greater than 90% positive predictive value, or a greater than 95% positive predictive value based on the expression level of the at least one gene; and/or based on the predicting, treating the subject with the autoimmune therapeutic drug. In some cases, the positive predictive value is determined using a cohort of a specific size. For example, the method may have a positive predictive value provided herein when evaluated in a cohort of greater than 5, 10, 25, 50, 100, 150, 200, 250, 500, or 1000 patients.

In some embodiments, this disclosure provides a method of determining whether a skin lesion of a subject will be responsive to an autoimmune therapeutic drug comprising penetrating skin of the subject with a microneedle device, wherein the microneedle device comprises one or more nucleic acid probes coupled to a microneedle. RNA molecules are obtained from the subject by removing the microneedle device from the skin of the subject. In some cases, high throughput sequencing on the RNA molecules is performed to generate sequence reads. The sequence reads are aligned with a signature of sequence reads associated with a positive response to an autoimmune disease therapeutic drug to obtain aligned sequence reads. A trained algorithm is applied to the aligned sequence reads, wherein the trained algorithm has a greater than 70%, 80%, 85%, 90% or 95% positive predictive value for predicting response to the autoimmune disease therapeutic drug. In some cases, the aligned sequence reads is used to determine an expression level of at least one RNA molecule; and a trained algorithm is applied to the expression level of the at least one RNA molecule, wherein the trained algorithm predicts whether the subject with the skin lesion will be responsive to an IL-17 mediated treatment, an IL-23 mediated treatment, a TNFα mediated treatment, or any combination thereof. In some cases, high throughput sequencing is performed on the RNA biomarkers to generate one or more sequence reads for the subject. The one or more sequence reads is aligned with a known signature of sequence reads, wherein the known signature of sequence reads is associated with a positive response to the recommended treatment, thereby obtaining aligned sequence reads. The subject is classified as having a likelihood of positively responding to the recommended treatment by applying a trained algorithm to the aligned sequence reads, wherein the trained algorithm comprises a greater than 50%, 60%, 70%, 80%, 85%, 90% or 95% positive predictive value for predicting a positive response to the recommended treatment. In some case, the trained algorithm also has a greater than 50%, 60%, 70%, 80%, 85%, 90% or 95% negative predictive value. In some cases, the recommended treatment comprises one or more autoimmune therapeutic drugs for an autoimmune disease or condition, including, for example, etanercept, infliximab, adalimumab, certolizumab, ustekinumab, secukinumab, ixekizumab, brodalumab, guselkumab, tildrakizumab, and risankizumab. In some cases, the autoimmune disease or condition is psoriasis, acne, atopic dermatitis (i.e., eczema), Raynaud's phenomenon, rosacea, skin cancer (e.g., basal cell carcinoma, squamous cell carcinoma and melanoma), or vitiligo.

In some embodiments, this disclosure provides a method of determining whether a subject with an autoimmune disorder of the skin will be responsive to an autoimmune therapeutic drug comprising extracting mRNA from skin of the subject, sequencing the mRNA from the skin of the subject; and predicting whether the subject with the autoimmune disorder will be responsive to etanercept, adalimumab, infliximab, certolizumab, secukinumab, ixekisumab, broadalumab, guselkumab, tildrakizumab, and risankizumab with a positive predictive value greater than 50%, 60%, 70%, 80%, 85%, 90% or 95%.

In some cases, the at least one gene is at least one gene from Table 6, Table 12, and/or Table 13. In some cases, the at least one gene is at least two genes from Table 6, Table 12, and/or Table 13. In some cases, the at least one gene is at least three genes from Table 6, Table 12, and/or Table 13. In some cases, the at least one gene is at least four genes from Table 6, Table 12, and/or Table 13. In some cases, the at least one gene is at least five genes from Table 6, Table 12, and/or Table 13. In some cases, the at least one gene is at least six genes from Table 6, Table 12, and/or Table 13. In some cases, the at least one gene is at least ten genes from Table 6, Table 12, and/or Table 13. In some cases, the at least one gene is at least fifteen genes from Table 6, Table 12, and/or Table 13. In some cases, the at least one gene is at least twenty genes from Table 6, Table 12, and/or Table 13. In some cases, the at least one gene is at least 25 genes from Table 6, Table 12, and/or Table 13. In some cases, the at least one gene is at least 50 genes from Table 6, Table 12, and/or Table 13.

In some cases, the at least one gene is at least one gene, two genes, three genes, four genes, five genes, or six genes from the group consisting of CNFN, CTSC, GBAP1, CRABP2, PCDH7, PPIG, RAB31, C3, and EGR. In some cases, the at least one gene is at least one gene, two genes, three genes, four genes, five genes, or six genes from the group consisting of CNFN, CTSC, GBAP1, CRABP2, PCDH7, and PPIG. In some cases, the at least one gene is at least one gene, two genes, three genes, four genes, five genes, or six genes from the group consisting of PCDH7, PPIG, RAB31, C3, and EGR.

In some cases, the at least one gene is at least one gene, two genes, or three genes from the group consisting of CNFN, CTSC, GBAP1, and CRABP2. In some cases, the at least one gene is at least one gene, two genes, or three genes from the group consisting of PPIG, RAB31, C3, and EGR. In some cases, the at least one gene is at least one gene, two genes, or three genes from the group consisting of PCDH7, PPIG, RAB31, and C3. In some cases, the at least one gene is at least one gene, two genes, or three genes from the group consisting of GBAP1, CRABP2, PCDH7, PPIG.

In some cases, the at least one gene is at least one gene, two genes, three genes, four genes, five genes, or six genes from the group consisting of SERPINB3, SERPINB4, S100A7A, PI3, KRT6A, LCN2, DEFB4A, DEFB4B, SPRR1A, IL36G, MX1, IF127, CD36, CD24, and IL4R. In some cases, the at least one gene is at least one gene, two genes, three genes, four genes, five genes, or six genes from the group consisting of KRT6A, SPRR1A, CD36, IL4R, LCN2, and IF1I27. In some cases, the at least one gene is at least one gene, two genes, three genes, four genes, five genes, or six genes from the group consisting of CD36, IL4R, S100A7A, SERPINB4, MX1, and SERPINB3. In some cases, the at least one gene is at least one gene, two genes, three genes, four genes, five genes, or six genes from the group consisting of LCN2, IFI27, DEFB4A, IL36G, CD24, and PI3.

In some cases, the at least one gene is at least one gene, two genes, or three genes from the group consisting of IL4R, LCN2, and IF1I27. In some cases, the at least one gene is at least one gene, two genes, or three genes from the group consisting of PI3, IF127, and SERPINB3. In some cases, the at least one gene is at least one gene, two genes, or three genes from the group consisting of IL4R, S100A7A, and MX1. In some cases, the at least one gene is at least one gene, two genes, or three genes from the group consisting of CD36, LCN2, and SERPINB4.

In some cases, the at least one gene is at least one gene, two genes, three genes, four genes, five genes, or six genes from the group consisting of MTCO1P12, MTATP6P1, CLSTN1, PDPN, LDLRAD2, and GSTM3. In some cases, the at least one gene is at least one gene, two genes, three genes, four genes, five genes, or six genes from the group consisting of AL158847.1, DAD1, LDLRAD2, ZNF395, MGMT, and AL136982.4. In some cases, the at least one gene is at least one gene, two genes, three genes, four genes, five genes, or six genes from the group consisting ofNREP, PPIF, PRIM1, AL136982.5, MTATP6P1, and SMPD3. In some cases, the at least one gene is at least one gene, two genes, three genes, four genes, five genes, or six genes from the group consisting of PDPN, TXNRD1, GSTM3, GPSM1, GLRX, and USP2.

In some cases, the at least one gene is at least one gene, two genes, or three genes from the group consisting of MTCO1P12, CLSTN1, and GSTM3. In some cases, the at least one gene is at least one gene, two genes, or three genes from the group consisting of NREP, PPIF, and PRIM1. In some cases, the at least one gene is at least one gene, two genes, or three genes from the group consisting of AL136982.5, MTATP6P1, and SMPD3. In some cases, the at least one gene is at least one gene, two genes, or three genes from the group consisting of PDPN, TXNRD1, and GSTM3.

The gene or genes used to detect a response to treatment may, in some cases, engage in a common pathway, such as an IL-17-mediated pathway, TNF-alpha pathway, or IL-23 pathway. In some cases, the at least one gene comprises at least 2, 3, 4, 5, 6, 7, 10, 15, or 20 genes that do not share a common upstream regulator or do not share a common pathway. In some cases, the genes have some relationship with the recommended treatment, e.g., the genes may be involved with a particular pathway (e.g., IL-17, I1-23, or TNF-alpha mediated pathway). In some cases, at least one gene does not have a known relationship with a recommended treatment. For example, the gene used to evaluate a response to treatment for a particular therapeutic may not be involved in the pathway targeted by the therapeutic. In some cases, the autoimmune therapeutic drug is an IL-17-mediated treatment and the at least one gene comprises at least one gene that is not involved in an IL-17 mediated pathway. In some cases, the autoimmune therapeutic drug is an IL-23-mediated treatment and the at least one gene comprises at least one gene that is not involved in an IL-23 mediated pathway. In some cases, the autoimmune therapeutic drug is a TNF-alpha-mediated treatment and the at least one gene comprises at least one gene that is not involved in a TNF-alpha-mediated pathway.

In some cases, a trained algorithm is applied to expression level of the at least one gene in order to predict the subject's likelihood of responding to the therapeutic. In some cases, the algorithm is trained using samples from patients that were administered a single type of drug. For example, the patients may have been administered an IL-17 mediated treatment, TNF-alpha mediated treatment or an IL-23 mediated treatment.

In some cases, the methods comprise use of a microneedle device. In some cases, the method of preparing a biological sample and identifying one or more therapeutic drugs may comprise: (a) contacting skin of a subject with a microneedle device, wherein the microneedle device comprises one or more nucleic acid probes coupled to a microneedle, as described elsewhere herein 610; (b) applying pressure to the microneedle device such that the microneedle device penetrates the skin of the subject 612; (c) obtaining extracted RNA molecules from the subject by removing the microneedle device from the skin of the subject 614; (d) performing high throughput sequencing on the extracted RNA molecules to generate one or more sequence reads for the subject 616; (e) aligning the one or more sequence reads for the subject with a known signature of sequence reads, wherein the known signature of sequence reads is associated with a positive response to the one or more therapeutic drugs, thereby obtaining aligned sequence reads 618; and classifying the subject as having a likelihood of positively responding to the one or more therapeutic drugs by applying a trained algorithm to the aligned sequence reads, wherein the trained algorithm has a greater than 70% positive predictive value, a greater than 75% positive predictive value, a greater than 80% positive predictive value, a greater than 85% positive predictive value, a greater than 90% positive predictive value, or a greater than 95% positive predictive value 620. In some embodiments, the method of preparing a biological sample and identifying one or more therapeutic drugs may further comprise administering the one or more therapeutic drugs to the subject. In some instances, the autoimmune disease or condition is psoriasis.

In some cases, the subject has a PASI of at least 8, at least 9, at least 10, at least 15. In some cases, the subject has a PASI of at least 8 and at least a PASI 75, 80, 90, 95, or 100 after treatment with the recommended drug. In some cases, the subject has a PASI of at least 10 and a PASI 75, 80, 90, 95, or 100 after treatment. In some embodiments, the trained algorithm may further comprise a greater than 50% negative predictive value for predicting a greater than 50% likelihood of positive response to the one or more therapeutic drugs. In some cases, the positive predictive value may be greater than 50%, 60%, 70%, 80% or 90%. In some instances, the negative predictive value may be or greater than 50%, 60%, 70%, 80% or 90%. In some embodiments, the extracted RNA molecules may be transcribed from one or more of the following genes listed in Table 6, Table 12, or Table 13. In some embodiments, the recommended treatment may comprise one or more autoimmune therapeutic drugs for an autoimmune disease or condition. In some cases, the autoimmune disease or condition may be psoriasis. In some instances, the recommended treatment may comprise etanercept, infliximab, adalimumab, certolizumab, ustekinumab, secukinumab, ixekizumab, brodalumab, guselkumab, tildrakizumab, risankizumab, or any combination thereof.

Response to a Treatment

In some cases, the variability of gene expression between one or more subjects may be predictive of the response of a particular treatment for a disease or condition, particularly psoriasis. Aspects of the invention disclosed herein, in some embodiments, provide a method for determining the response to a treatment for a disease or condition in a subject afflicted with the disease or condition. In some embodiments, the method may further comprise recommending an additional treatment specific to the score. In some cases, the method may further comprise administering the treatment or the additional treatment to the subject. In some instances, the one or more nucleic acid molecules may comprise deoxyribonucleic acid (DNA) molecules. In some cases, the one or more nucleic acid molecules comprise RNA molecules. In some cases, the RNA molecules may comprise messenger RNA (mRNA) molecules.

In some embodiments, the disease or condition may be an autoimmune disease. In some cases, the autoimmune disease may be psoriasis.

Determining a Mild, Moderate or Severe Form of a Known Disease or Condition

In some cases, particular forms of a disease (e.g., severe, moderate, normal, etc.) may comprise different gene signatures. Certain known treatments for known diseases or conditions are not as efficacious against a particular form of a disease as compared to an alternate form of the same disease that may comprise. In some instances, the method may further comprise recommending a treatment specific to the score. In some cases, the method may further comprise administering the treatment to the subject. In some cases, the disease or condition may be an autoimmune disease. In some instances, the autoimmune disease may be psoriasis. In some cases, the one or more nucleic acid molecules may comprise DNA molecules. In some embodiments, the one or more nucleic acid molecules may comprise RNA molecules. In some cases, the RNA molecules may comprise mRNA molecules.

In some embodiments, the at least five genes from Table 6, Table 12, or Table 13 may comprise genes associated with one or more pathways. In some cases, the at least five genes from Table 6, Table 12, or Table 13 may comprise at least 2 genes associated with activation of the one or more pathways.

Identifying Activation of Biological Pathways Associated with a Disease or Condition Aspects of the disclosure, in some embodiments, provide methods for identifying the activation of one or more pathways that may be associated with a disease or condition in a subject 642, as seen in FIG. 6C. In some embodiments, the method for identifying the activation of one or more pathways that may be associated with a disease or condition in a subject may comprise the steps of (a) contacting skin of the subject with a microneedle device, wherein the microneedle device comprises one or more nucleic acid probes coupled to a microneedle 644; (b) applying pressure to the microneedle device such that the microneedle device penetrates the skin of the subject 646; (c) obtaining extracted RNA molecules from the subject by removing the microneedle device form the skin of the subject 648; (d) performing high throughput sequencing on the extracted RNA molecules to generate one or more sequence reads for the subject 650; (e) aligning the one or more sequence reads for the subject with a known signature of sequence reads, wherein the known signature of sequence reads may be associated with activation of one or more pathways associated with a disease or condition 652; and (f) classifying the subject as having a greater than 50% likelihood of developing the disease or condition associated with activation of the one or more pathways by applying a trained algorithm to the aligned sequence reads, wherein the trained algorithm has a greater than 50% positive predictive value or greater than 50% negative predictive value for predicting a greater than 50% likelihood of developing the disease associated with activation of the one or more pathways 654. In some cases, the method may further comprise recommending a treatment specific to the activation of the one or more pathways. In some cases, the method may further comprise administering the treatment specific to the activation of the one or more pathways to the subject. In some instances, the microneedle may be a solid microneedle.

In some embodiments, the trained algorithm may further comprise a greater than 50% negative predictive value for predicting a greater than 50% likelihood of developing the disease or condition associated with activation of the one or more pathways. In some cases, the positive predictive value may be greater than 50%, 60%, 70%, 80% or 90%. In some instances, the negative predictive value may be or greater than 50%, 60%, 70%, 80% or 90%.

In some embodiments, the disease or condition may be an autoimmune disease or condition. In some cases, the autoimmune disease or condition may be psoriasis. In some embodiments, the extracted RNA molecules may be transcribed from one or more genes comprising at least one gene associated with activation of the one or more pathways. In some cases, the one or more genes may comprise at least two genes associated with activation of the one or more pathways. In some cases, the one or more genes may comprise any one of the genes listed in Table 6, Table 12 or Table 13.

Subjects

As used herein, the term "subject" refers to any animal, including mammals and non-mammals), for example, humans, non-human primates (e.g., rhesus macaques, crab-eating macaques, stump-tailed macaques, pig-tailed macaques, squirrel monkeys, owl monkeys, baboons, chimpanzees, marmosets and spider monkeys, etc.), rodents (e.g., mice, rats, guinea pigs, etc.), dogs, cats, pigs, etc. In some cases, the subject is a human subject.

In some embodiments, the subject may be experiencing a skin condition or have symptoms of a skin condition. Examples of skin conditions that may be detected and/or treated by the methods and devices provided herein include: psoriasis, acne, atopic dermatitis (i.e., eczema), Raynaud's phenomenon, rosacea, skin cancer (e.g., basal cell carcinoma, squamous cell carcinoma and melanoma), and vitiligo. In some cases, the subject has, or has symptoms of, one or more skin conditions, for example, psoriasis and atopic dermatitis. In some cases, the subject may be experiencing different degrees of skin conditions, for example, mild, moderate, severe, and very severe. Examples of symptoms of psoriasis include red patches of skin covered with thick, silvery scales; small scaling spots; dry, cracked skin that may bleed or itch; itching, burning or soreness;

thickened, pitted or ridged nails; swollen and stiff joints.

Psoriasis Area and Severity Index (PASI) Score

The Psoriasis Area and Severity Index (PASI) score is commonly used to measure discoloration, thickness, scaling, and coverage of these plaques. A caregiver (e.g., a medical doctor, nurse, nurse practitioner, physician's assistant, etc.) can use PASI score to measure the severity and extent of psoriasis and observe the effectiveness of psoriasis treatments. Using the tool also allows a caregiver to monitor the progression of the condition and evaluate the effectiveness of treatment.

The scoring involves rating the symptoms of psoriasis from none to very severe and estimating the percentage of the body that they affect. Researchers also use PASI scores to determine the effectiveness of psoriasis medications in clinical trials.

The range of absolute PASI scores is 0-72, with higher scores indicating a greater severity of psoriasis. A score of 0 indicates no psoriasis, while a score higher than 10 suggests severe psoriasis. The scoring system includes a section for intensity and another for body coverage. The intensity section of the score measures 1) discoloration (i.e., redness), 2) thickness, and 3) scaling. The area section shows the extent to which psoriasis affects the following: 1) head and neck, 2) upper limbs, 3) trunk, and 4) lower limbs.

PASI scores can calculate PASI scores as follows:

| | |
|---|---|
| A scores | Add together the three intensity scores (discoloration, thickness, and scaling) for each of the four body regions to get four A scores. Each intensity score can be given based on the severity of the symptoms: 0: absent symptoms; 1: mild symptoms; 2: moderate symptoms; 3: severe symptoms; 4: very severe symptoms. |
| B scores | A B score is assigned for each of the four body regions: 0: absence of symptoms, 1: 1-9% coverage, 2: 10-29% coverage, 3: 30-49% coverage, 4: 50-69% coverage, 5: 70-89% coverage, and 6: 90-100% coverage. |
| C scores | Multiply the A score by the B score for each body region to get four C scores |
| D scores | Multiply each C score by the amount of body surface area that the region represents. This amount is 0.1 for the head and neck, 0.2 for the arms, 0.3 for the trunk, and 0.4 for the legs. This gives four D scores. |
| PASI score | Add together the four D scores. |

Clinical researchers often use PASI percentage response rates to indicate treatment outcomes. For example, PASI 75 means that a person's PASI score has decreased 75% from baseline, which indicates a significant improvement in the condition. Conventional goal of treatment has been to achieve PASI 75. However, a PASI 90 or PASI 100 (i.e., a 90% or 100% reduction in PASI scores, respectively) is more desirable.

In some cases, a subject provided herein has a PASI of at least 5, at least 6, at least 7, at least 8, at least 9, at least 10, or at least 15. In some cases, a subject has moderate-to-severe psoriasis and a baseline PASI of greater than or equal to 10. In some cases, the methods provided herein provide a prediction for whether a subject will respond to a particular treatment. In some cases, following being treated by the recommended treatment, the subject responds to the treatment and has as a decrease in PASI score. In some cases, the subject's response to treatment may be a particular response at week 16 following treatment, such as week 16 PASI60; week 16 PASI75, week 16 PASI80, week 16 PASI80, week 16 PASI90, week 16 PASI95, week 16 PASI 99, or week 16 PASI 100. In some cases, the subject's response to treatment may be a particular response at week 12 following treatment, such as week 12 PASI60; week 12 PASI75, week 12 PASI80, week 12 PASI80, week 12 PASI90, week 12 PASI95, week 12 PASI 99, or week 12 PASI 100. In some cases, the subject's response to a treatment is a response at week 8 following treatment, such as week 8 PASI60; week 8 PASI75, week 8 PASI80, week 8 PASI80, week 8 PASI90, week 8 PASI95, week 8 PASI 99, or week 8 PASI 100. In some cases, the subject's response to a treatment is a response at week 4 following treatment, such as week 4 PASI60; week 4 PASI75, week 4 PASI80, week 4 PASI80, week 4 PASI90, week 4 PASI95, week 4 PASI 99, or week 4 PASI 100. In some embodiments, the subject's response to treatment is evaluated at least 2 weeks, at least 3 weeks, at least 4 weeks, at least 8 weeks, at least 12 weeks, at least 16 weeks, at least 20 weeks, or at least 24 weeks following treatment. In some embodiments, the subject's response to treatment is evaluated at most 2 weeks, at most 3 weeks, at most 4 weeks, at most 8 weeks, at most 12 weeks, at most 16 weeks, at most 20 weeks, at most 24 weeks following treatment, or at most 50 weeks following treatment. For example, the subject's response to treatment may, in some embodiments, be evaluated between 8 and 12 weeks following treatment, between 4 and 12 weeks following treatment, and/or between 8 and 16 weeks following treatment. In some embodiments, the patient's PASI response may be at least PASI60, at least PASI70, at least PASI80, at least PASI90, at least PASI95, at least PASI99, or PASI100 for any of the periods following treatment.

Sample Preparation

Nucleic acids can be extracted from a sample using the microneedle devices described herein, or extracted directly from a sample (e.g., biopsy sample) using an extraction method other than one that involves use of a microneedle device. The types of nucleic acids that can be extracted include any nucleic acid molecules that encode genetic information, including for example, messenger RNA (mRNA), microRNA, DNA (e.g., nuclear DNA or mitochondrial DNA), a mixture of mRNA and DNA, short RNA, isolated RNA, and isolated DNA. The biopsy samples that can be used for nucleic acids extraction can include any tissue removed from any part of the body, for example, from the surface of the body (e.g., skin, hair, scalp, surface skin, nails, skin debris, hair follicles); from inside the body (e.g., brain, heart, lungs, pancreas. kidney, liver, intestine, muscles, connective tissue, bone, cartilage, or blood). The biopsy sample can be obtained invasively, non-invasively, or minimally invasively. In some cases, the biopsy sample is obtained from one or more active lesions, dormant lesions, or normal tissues.

In some cases, once removed from skin, the device and extracted RNA biomarkers may be placed into a storage buffer, a transport buffer, or an analysis buffer. The device and extracted RNA biomarkers may be stored at −80° C., −20° C., −4° C., 4° C. or room temperature. Alternatively, the device may be placed into a buffer to dissociate the extracted RNA biomarkers from the device, and the extracted RNA biomarkers may be stored at −80° C., −20° C., −4° C., 4° C. or room temperature. The extracted RNA biomarkers (with or without the device) may be sent to a laboratory for further analysis.

In some cases, DNA is sequenced using nanopore sequencing, in which a single molecule of DNA or RNA can be sequenced without the need for PCR amplification or chemical labeling of the sample. In some cases, the extracted nucleic acids of the sample s may be amplified and analyzed by next generation sequencing (NGS), high-throughput sequencing, massively parallel sequencing, or sequencing-by-synthesis. Different sequencing approaches can include, for example, pyrosequencing, sequencing by reversible terminator chemistry, sequencing-by-ligation mediated by ligase enzymes, or phosphor-linked fluorescent nucleotides or real-time sequencing. Methods for performing genomic analyses may also include microarray methods. In some cases, genomic analysis may be performed in combination with any of the other methods herein. For example, a sample may be obtained, tested for adequacy, and divided into aliquots. One or more aliquots may then be used for cytological analysis of the present invention, one or more may be used for gene expression profiling methods of the present invention, and one or more may be used for genomic analysis. It is further understood the present invention anticipates that one skilled in the art may wish to perform other analyses on the biological sample that are not explicitly provided herein.

In some embodiments, wherein the nucleic acid molecule is RNA, the method further comprises converting the captured RNA to DNA (e.g., cDNA) that is readily available for sequencing (e.g. sequencing by synthesis, or nanopore sequencing). In some cases, RNeasy Mini kits (Qiagen, Valencia, CA) are used for RNA extraction. RNAase-Free DNase digestion (Qiagen, Valencia, CA) can be used to remove genomic DNA from the RNA preparations. Taqman kits (Applied Biosystems, Foster City, CA) can be used for reverse transcription. For example, 200 ng total mRNA was added in 20 μl reverse-transcription reaction and the mixture was incubated 5 minutes at 25° C., 30 minutes at 48° C., then 5 minutes at 95° C. cDNAs were stored at −20° C. for further use.

In some case, cDNA can be amplified and then sequenced by a commercial vendor (Psomagen, Inc., Rockville, MD) according to standard procedures. Library preparation can be accomplished using Illumina Nextera DNA Flex kits according to the manufacturer's instructions. Prepared indexed libraries can be loaded onto a NovaSeq6000 S4 with read length of 150PE for sequencing of 40 M reads per sample. During sequencing, the quality score (Q30) may be maintained at a certain level, e.g., over 75%. Upon completion of runs, FASTQ file quality may be checked with FASTQC and trimmed with the Trim_galore program. The trimmed FASTQ can be aligned and mapped to human reference genome (e.g., GRCh38) using hisat2 program. In some embodiments, the number of reads is counted for each Ensemble gene ID using FeatureCounts program and *Homo sapiens* GRCH38.84.gtf. In some cases, RNA expression analysis is further processed using Bioconductor package edgeR. Genes may be filtered using filterByExpr before logCPM (counts per million reads) were calculated. Plots may be made with ggplot2 and heatmap.2 functions in R. Percent of genes detected may be determined using the ratio of genes detected (with >0 count) over the total number of Ensemble genes.

The general methods for determining gene expression product levels may include but are not limited to one or more of the following: additional cytological assays, assays for specific proteins or enzyme activities, assays for specific expression products including protein or RNA or specific RNA splice variants, in situ hybridization, whole or partial genome expression analysis, microarray hybridization assays, SAGE, enzyme linked immuno-absorbance assays, mass-spectrometry, immuno-histochemistry, or blotting. Gene expression product levels may be normalized to an internal standard such as total mRNA or the expression level of a particular gene including but not limited to glyceralde-hyde 3 phosphate dehydrogenase, or tublin.

In some embodiments, microarray analysis begins with extracting and purifying nucleic acid from a biological sample, (e.g. a biopsy or fine needle aspirate) using methods known to the art. For expression analysis, it can be advantageous to extract and/or purify RNA from DNA. It can further be advantageous to extract and/or purify mRNA from other forms of RNA such as tRNA and rRNA.

In some embodiments, purified nucleic acid may further be labeled with a fluorescent, radionuclide, or chemical label such as biotin or digoxin for example by reverse transcription, PCR, ligation, chemical reaction or other techniques. The labeling can be direct or indirect which may further require a coupling stage. The coupling stage can occur before hybridization, for example, using aminoallyl-UTP and NHS amino-reactive dyes (like cyanine dyes) or after, for example, using biotin and labeled streptavidin. The modified nucleotides (e.g. at a 1 aaUTP:4 TTP ratio) are added enzymatically at a lower rate compared to normal nucleotides, typically resulting in 1 every 60 bases (measured with a spectrophotometer). The aaDNA may then be purified with, for example, a column or a diafiltration device. The aminoallyl group is an amine group on a long linker attached to the nucleobase, which reacts with a reactive label (e.g. a fluorescent dye).

In some embodiments, the labeled samples may then be mixed with a hybridization solution which may contain SDS, SSC, dextran sulfate, a blocking agent (such as COT1 DNA, salmon sperm DNA, calf thymum DNA, PolyA or PolyT), Denhardt's solution, formamine, or a combination thereof. A hybridization probe is a fragment of DNA or RNA of variable length, which is used to detect in DNA or RNA samples the presence of nucleotide sequences (the DNA target) that are complementary to the sequence in the probe. The probe thereby hybridizes to single-stranded nucleic acid (DNA or RNA) whose base sequence allows probe-target base pairing due to complementarity between the probe and target. The labeled probe is first denatured (by heating or under alkaline conditions) into single DNA strands and then hybridized to the target DNA.

In some embodiments, to detect hybridization of the probe to its target sequence, the probe is tagged (or labeled) with a molecular marker; commonly used markers are 32P or Digoxigenin, which is non-radioactive antibody-based marker. DNA sequences or RNA transcripts that have moderate to high sequence similarity to the probe are then detected by visualizing the hybridized probe via autoradiography or other imaging techniques. Detection of sequences with moderate or high similarity depends on how stringent the hybridization conditions were applied-high stringency, such as high hybridization temperature and low salt in hybridization buffers, permits only hybridization between nucleic acid sequences that are highly similar, whereas low stringency, such as lower temperature and high salt, allows hybridization when the sequences are less similar. Hybridization probes used in DNA microarrays refer to DNA covalently attached to an inert surface, such as coated glass slides or gene chips, and to which a mobile cDNA target is hybridized.

In some embodiments, the mix may then be denatured by heat or chemical means and added to a port in a microarray. The holes may then be sealed, and the microarray hybridized, for example, in a hybridization oven, where the microarray is mixed by rotation, or in a mixer. After an overnight hybridization, non-specific binding may be washed off (e.g. with SDS and SSC). The microarray may then be dried and scanned in a special machine where a laser excites the dye and a detector measures its emission. The image may be overlaid with a template grid and the intensities of the features (several pixels make a feature) may be quantified.

Various kits can be used for the amplification of nucleic acid and probe generation of the subject methods. Examples of kit that can be used in the present invention include but are not limited to Nugen WT-Ovation FFPE kit, cDNA amplification kit with Nugen Exon Module and Frag/Label module. The NuGEN WT-Ovation™ FFPE System V2 is a whole transcriptome amplification system that enables conducting global gene expression analysis on the vast archives of small and degraded RNA derived from FFPE samples. The system is comprised of reagents and a protocol required for amplification of as little as 50 ng of total FFPE RNA. The protocol can be used for qPCR, sample archiving, fragmentation, and labeling. The amplified cDNA can be fragmented and labeled in less than two hours for GeneChip® 3' expression array analysis using NuGEN's FL-Ovation™ cDNA Biotin Module V2. For analysis using Affymetrix GeneChip® Exon and Gene ST arrays, the amplified cDNA can be used with the WT-Ovation Exon Module, then fragmented and labeled using the FL-Ovation™ cDNA Biotin Module V2. For analysis on Agilent arrays, the amplified cDNA can be fragmented and labeled using NuGEN's FL-Ovation™ cDNA Fluorescent Module.

In some embodiments, Ambion WT-expression kit can be used. Ambion WT-expression kit allows amplification of total RNA directly without a separate ribosomal RNA (rRNA) depletion step. With the Ambion® WT Expression Kit, samples as small as 50 ng of total RNA can be analyzed on Affymetrix® GeneChip® Human, Mouse, and Rat Exon and Gene 1.0 ST Arrays. In addition to the lower input RNA requirement and high concordance between the Affymetrix® method and TaqMan® real-time PCR data, the Ambion® WT Expression Kit provides a significant increase in sensitivity. For example, a greater number of probe sets detected above background can be obtained at the exon level with the Ambion® WT Expression Kit as a result of an increased signal-to-noise ratio. Ambion WT-expression kit may be used in combination with additional Affymetrix labeling kit.

In some embodiments, AmpTec Trinucleotide Nano mRNA Amplification kit (6299-A15) can be used in the subject methods. The ExpressArt® TRinucleotide mRNA amplification Nano kit is suitable for a wide range, from 1 ng to 700 ng of input total RNA. According to the amount of input total RNA and the required yields of aRNA, it can be used for 1-round (input >300 ng total RNA) or 2-rounds (minimal input amount 1 ng total RNA), with aRNA yields in the range of >10 µg. AmpTec's proprietary TRinucleotide priming technology results in preferential amplification of mRNAs (independent of the universal eukaryotic 3'-poly (A)-sequence), combined with selection against rRNAs. This kit can be used in combination with cDNA conversion kit and Affymetrix labeling kit.

In some embodiments, the raw data may then be normalized, for example, by subtracting the background intensity and then dividing the intensities making either the total intensity of the features on each channel equal or the intensities of a reference gene and then the t-value for all the intensities may be calculated. More sophisticated methods include z-ratio, loess and lowess regression and RMA (robust multichip analysis) for Affymetrix chips.

In some cases, PolyA tailed mRNA is captured on a support via hybridization to a polyT DNA capture probe or primer coupled to the surface of a support. The polyT strand is next extended with a reverse transcriptase polymerase to make a double stranded molecule comprising a DNA:RNA duplex. Next, a transposome complex (e.g., Tn5 transposase bound with an adaptor sequence and sequences complementary to surface amplification primers) is added to the support, which undergoes a transposition reaction with and tagments the duplex, ligating a DNA adaptor oligo to the 5' end of the RNA strand. A strand displacing polymerase (e.g., Bst polymerase) can then be used to extend the 3' end of the DNA strand, displacing the non-transferred strand of the transposome complex and copying the RNA strand to its 5' DNA chimeric end. In some embodiments, the DNA adaptor oligo comprises a sequence complementary to an anchor primer on a substrate configured for sequencing. In some embodiments, the DNA adaptor oligo comprises a sequence that is complementary to sequencing primer for sequencing. The double-stranded molecule can then be amplified (e.g., cluster amplification) and sequenced with a sequencing primer. The primer partially comprises the adaptor sequence and the upstream adaptor sequence. Alternatively, the other end of the molecule (the polyT end) can be sequenced with a primer that anneals upstream of the polyT sequence and is extended with natural dATP nucleotides before commencing cycles of sequence by synthesis (SBS) chemistry.

In some cases, RNA is fragmented and treated with a phosphatase. A single stranded adaptor molecule is ligated to the 3'end of each RNA fragment comprising the complement of a surface bound primer. The fragments are then added to a support and captured via hybridization. The hybridized RNA molecules are converted to a DNA:RNA duplex with a reverse transcriptase polymerase. A transposome complex or composition comprising a transposase and an adaptor duplex (i.e., transposon) of an ME with P5 is used to tagment the duplex. Following extension of the DNA strand to the end with a strand displacing polymerase, the molecules can be amplified (e.g., cluster amplification) and sequenced.

Bioinformatic Analysis of Sequence Reads

As used herein, positive predictive value (PPV) is the percentage of true positives among all subjects who test positive. It can be computed as follow: PPV=TP/(TP+FP) where TP and FP are the number of true positive and false positive results, respectively.

As used herein, negative predictive value (NPV) is the percentage of true negative among all subjects who test negative. It can be computed as follow: PPV=TN/(TN+FN)

where TN and FN are the number of true negatives and false negatives results, respectively.

An algorithm (Mind.Px) is developed herein for the prediction of response to biologics (anti-IL-17, anti-IL-23) used for the treatment of patients with psoriasis, by comparing baseline transcriptomes with clinical response to biologic drugs at 12 weeks after initial treatment. The 62 patients (out of 75) who responded had Psoriasis Area and Severity Index changes of 0.75 or greater, whereas the non-responders had Psoriasis Area and Severity Index (PASI) changes of −0.2 to 0.75. Cross-validation using linear regression modeling showed a balanced prediction accuracy of 0.71 using PASI75 as the cutoff for evaluating the classifier performance. A positive prediction value of 0.95 was achieved.

In some cases, a sequence read from a subject is compared with a sequence read from a positive or negative control. A positive control is a subject diagnosed with the disease or condition. A negative control is a healthy person who does not have any symptoms or history of symptoms of the disease or condition. Alternatively, a negative control can be the baseline for a subject prior to treatment.

Biologics

As used herein, the term "biologics" means medicinal products obtained from living organisms (e.g., humans, animals, or microorganisms), including recombinant biologics, which are produced by genetic engineering technique. For example, a biologic may contain proteins that control the action of other proteins and cellular processes, genes that control production of vital proteins, modified human hormones, or cells that produce substances that suppress or activate components of the immune system. In some cases, a biologic is an antibody (e.g., a monoclonal antibody). In some cases, the subject is treated with one or more of the following biologics: tumor necrosis factor inhibitors (e.g., adalimumab, etanercept, infliximab, golimumab and certolizumab pegol); IL-17 inhibitors (e.g., secukinumab, ixekizumab, and brodalumab); and the IL-23 inhibitors (e.g., tildrakizumab, guselkumab, ustekinumab, and risankizumab).

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "bases," as used herein refers to nucleotides. In some cases, "bases" can refer to base pairs ("bp"), e.g. 1 base equals 1 base pair. As used herein, the terms, "bases," and "base pairs," are used interchangeably.

As used herein, the term "about" means within 10% above or below a given value. For example, "about 10", would include values from 9 to 11, unless otherwise indicated by the context in which the term is used.

The following examples are provided to further illustrate the advantages and features of the present invention, but are not intended to limit the scope of the invention. While they are typical of those that might be used, other procedures, methodologies, or techniques known to those skilled in the art may alternatively be used.

EXAMPLES

Example 1: Manufacturing the Device

A device of the present disclosure is manufactured using injection molding. The device is manufactured by injecting heated (e.g. molten) material, e.g. a polyolefin resin disclosed herein, into a mold of the device, according to the features disclosed herein. The mold comprises a plurality of cavities for forming a plurality of microneedles, cavity for forming an interior section comprising the plurality of microneedles, and one or more cavities for forming one or more peripheral sections adjacent to the interior section. For this device, the width of the interior section is less than the width of the peripheral section(s). The width of the inter-section is about a 1:5 ratio in size as compared to the width of the peripheral section(s).

As the heat material is injected through the mold, the smaller width of the interior section (as compared to the peripheral section(s)) facilitates the heated materials movement to the one or more cavities to generate the plurality of microneedles prior to generating the interior section and the peripheral section(s).

The result is a device as described herein comprising uniform, sharp microneedles. No more than 3% of the microneedles in the plurality of microneedles deviate (+/−). by more than about 50 μm from an average length of the microneedles of the plurality of microneedles.

Example 2: Bonding Probes to the Device of Example 1

The microneedles of the device of Example 1 are plasma treated as described herein. The device or a portion thereof is placed into a plasma vacuum chamber, the plasma vacuum chamber is closed, creating a sufficient vacuum seal, all of the pre-existing gas present in the chamber is evacuated and a plasma treatment gas is pumped into the plasma vacuum chamber to a defined pressure, enabling the generation of gas plasma.

The gas plasma reacts with the heated material of the device (e.g. a polyolefin resin described herein) and renders the material more readily reactive to form covalent bonds with the probes described herein.

Example 3: Kinetics of mRNA Extraction

The optimal time for mRNA extraction was determined by placing a microneedle device described herein on the skin of healthy subjects for varying periods of time, followed by removal of the patch from the skin and subsequent amplification, cDNA synthesis, and qPCR analysis. The devices were placed on subjects for 20 seconds, 1 minute, 5 minutes, and 10 minutes, and the cycle threshold (Ct) was measured for two biomarkers, GAPDH and KRT10, generated from the mRNA sample collected from the device at each residence time. All measurements were made in triplicate.

As can be seen in Table 1, optimal extraction occurs 5 minutes of residence time in the skin, with degradation starting to dominate by 10 minutes of skin insertion.

TABLE 1

| Time course of mRNA stability (values in cycle threshold (Ct)) | | | | |
|---|---|---|---|---|
| Gene | 20 s insertion | 1 m insertion | 5 m insertion | 10 m insertion |
| GAPDH | 31.69 | 30.56 | 30.04 | 30.82 |
| KRT10 | 28.49 | 27.45 | 25.98 | 27.07 |

Example 4: Qualification of Extracted mRNA

To demonstrate the quality of intact mRNA, bioanalyzer QC and qPCR analysis were performed with the mRNA extracted from a microneedle device described herein.

For intact/high quality mRNA, successful cDNA synthesis and amplification showed a distinct amplification peak spanning from about 300 to about 10,000 bp, with a peak at about 1,500 bp (FIG. 5A). Quantification of the area under these curves returned a corrected area QC ratio (corrected area for large mRNA fragments (700-20,000 bp)/corrected area for small mRNA fragments (150-200 bp)) of greater than 1. In contrast, the amplification peak shift with degraded mRNA to smaller fragments of 100-1,000 in partially degraded samples (FIG. 5B). Further, in fully degraded samples, the peak around 1,500 bp was no longer visible (FIG. 5C). Importantly, in these partially and fully degraded samples, the corrected area QC ratio was less than 1. Additionally, qPCR analysis was performed on these samples. Using a typical gene (B2M), the Ct value from degraded RNA sample increased to 22.70 from a Ct of 19.25 for the control sample (intact RNA); this increase of 3.45 Ct indicated approximately 11-fold decrease in the quantity of mRNA in the degraded sample.

Example 5: Prospective Prediction of Individual Patients Response to TNFα, IL-17 and IL-23 Inhibitors Response for patients with a psoriasis skin disease to particular drug classes (e.g., TNFα, IL-17i and IL-23i inhibitors) was determine prospectively prior to administering said drug classes via a predictive linear classifier modeling approach. To determine patient response a painless FDA-registered class I Dermal Biomarker Patch was used to pull an individual patient's entire RNA transcriptome through exposure of the Dermal Biomarker Patch and the patient's skin for 5 minutes. The Dermal Biomarker Patch was then processed, and the RNA adhered on the Dermal Biomarker Patch was extracted and sequenced using next-generation sequencing. The RNA sequencing readout was then aligned and compared with a database of patients with a similar disease condition RNA gene profiles and their respective responsive or non-responsiveness to a particular drug class. The comparison between RNA sequencing readout and the database with a predictive linear classifier provided a score of the probability that a particular drug or drug class will provide an efficacious response to treating a disease condition.

Using the aforementioned methods, the predictive linear classifier's positive predictor value (PPV), sensitive, and balanced accuracy was assessed for TNFαi, (PASI75 @W12), IL-17i (PASI75 @W 12) and IL-23i (PASI150 @W12) drug classes. The TNFαi inhibitor drug class was evaluated over a training set of 34 patients and a test set of 15. The resulting PPV, sensitivity and balanced accuracy for the linear classifier was 89%, 80%, and 80%, respectively.

The IL-17i inhibitor drug class was evaluated over a training set of 75 patients and a test set of 6. The resulting PPV, sensitivity and balanced accuracy for the linear classifier was 100%, 100%, and 100%, respectively. The IL-23i inhibitor drug class was evaluated over a training set of 17 patients and a test set of 17. The resulting PPV, sensitivity and balanced accuracy for the linear classifier was 90%, 82%, and 83%, respectively. The average of the three inhibitor drug classes PPV, sensitivity, and was calculated to be 95% PPV, 87% sensitivity, and 88% specificity.

Example 6. A Machine Learning-Based Test for Predicting Response to Psoriasis Biologies This study was designed to develop and prospectively validate a machine learning based algorithm that could predict patient response to the most common biologic drug classes used in the management of psoriasis patients. This type of tool would allow clinicians to have greater confidence that a given patient will respond to a specific drug class, which could lead to improved health outcomes and reduced wasted healthcare spend.

Patients were enrolled into one of two observational studies (STAMP studies) where dermal biomarker patches (DBPs) were applied at baseline prior to drug exposure, followed by clinical evaluations at 12 weeks after exposure. PASI measurements were made at baseline and 12 weeks to evaluate clinical response to a clinical phenotype. Responders were defined as those who reached PASI75 at 12 weeks. The transcriptomes obtained from the DBPs were sequenced and analyzed to derive and/or validate classifiers for each biologic class, which were then combined to yield predictive responses for all three biologic drug classes (IL-23i, IL-17i, and TNFαi).

A total of 242 psoriasis patients were enrolled in these studies, including 118 patients (49.6%) treated with IL-23i, 79 patients (33.2%) treated with IL-17i, 35 patients (14.7%) treated with TNFαi, and 6 patients (2.5%) treated with IL-12/23i. The IL-23i predictive classifier was developed from the earlier enrolled patients and independently validated with the latter enrolled patients. IL-17i and TNFαi predictive classifiers were developed using publicly available datasets and independently validated with patients from the STAMP studies. In the independent validation, positive predictive values for three classifiers (IL-23i, IL-17i, and TNFαi) were 93.1%, 92.3% and 85.7% respectively. Over the entire cohort, 99.5% of patients were predicted to respond to at least one drug class.

This study demonstrates the power of using baseline dermal biomarkers and machine learning methods as applied to the prediction of psoriasis biologic prior to drug exposure. Using this test, patients, physicians, and the health care system all can benefit in distinct ways. Precision medicine can be realized for individual patients as most will likely respond to their prescribed biologic the first time. Physicians can prescribe these drugs with increased confidence, and the healthcare system will realize lower net costs as well as greatly reduced wasted spend by significantly improving initial response rates to expensive biologic therapeutics.

Psoriasis is a T-cell mediated inflammatory skin disease characterized by discrete erythematous plaques and papules with micaceous scale. Worldwide, this is a common disease, with approximately 2.8% of the United States population, or 7.5 million people, diagnosed with psoriasis. Current treatment paradigms for psoriasis are distinguished by topical medications and/or phototherapy for mild to moderate patients, and systemic medications for patients who are classified as moderate to severe disease. The advent of biologic therapy as one of these systemic agents has revolutionized the management and treatment of psoriasis patients and is a direct result of the increased molecular understanding of the disease. Presently, there are eleven approved biologic agents approved for use in the United States for the treatment of psoriasis, with more under development. However, it is not clear which biologic would be effective for a given patient.

Disclosed herein is a novel biomarker capture platform that utilizes a dermal biomarker patch to capture the whole transcriptome including mRNA biomarkers from the epidermis and upper dermis. This platform showed excellent concordance with biopsy and provides a scalable method to access skin biomarkers in a minimally invasive manner. It is contemplated that the use of this platform in preliminary machine learning classifier builds for the prediction of response and non-response to IL-17 and IL-23 inhibitors. Also disclosed herein, is an extension of this preliminary study to the development and prospective validation of an actionable clinical test for predicting patient response to psoriasis biologics for all three drug classes.

Methods

Dermal Biomarker Patch Platform

Dermal biomarker patches (DBPs) used in this study were fabricated and modified as previously described and used according to the manufacturer's specifications.

Human Subject Recruitment and Enrollment

Data was analyzed from past and ongoing observational, multicenter (20 centers), single-arm, open-label, 12-week studies, referred as STAMP studies. The protocols for these studies were approved by local institution ethics committees and conforms to the provisions of the Declaration of Helsinki and the International Council for Harmonisation (ICH) Guidelines on Good Clinical Practice (GCP). All patients who received treatment provided written informed consent. The primary objective of the study protocols was to examine if baseline or on-therapy transcriptomics can be used to help predict selection of medications and provide new therapeutic targets for drug development (Table 2). Visits included screening, baseline, week 1, week 4, week 8, and week 12. PASI, PGA, and BSA scoring was performed at every visit excluding the screening visit. Subjects were administered the Dermal Biomarker Patch at every visit excluding the screening visit. Subject medical history, physical exam, and demographics were collected at screening.

TABLE 2

Schedule of activities for STAMP studies.

| | Visit Number | | | | | |
| --- | --- | --- | --- | --- | --- | --- |
| | | | Visit 3 | Visit 4 | Visit 5 | Visit 6 |
| | Visit 1 | Visit 2 | | | | |
| | | | Study Week | | | |
| | | | Week 1 | Week 4 | Week 8 | Week 12 |
| | Screening[3] | Baseline[3] | | | | |
| Informed Consent | X | | | | | |
| Inclusion/Exclusion Criteria | X | | | | | |
| Demographics | X | | | | | |
| Medical History [1] | X | | | | | |
| Physical Exam[2, 4] | X | | | | | |
| PASI[4] | X | X | | X | | X |
| PGA[4] | X | X | | X | | X |

TABLE 2-continued

Schedule of activities for STAMP studies.

| | | | Visit Number | | | |
|---|---|---|---|---|---|---|
| | Visit 1 | Visit 2 | Visit 3 | Visit 4 | Visit 5 | Visit 6 |
| | | | Study Week | | | |
| | Screening[3] | Baseline[3] | Week 1 | Week 4 | Week 8 | Week 12 |
| BSA[4] | X | X | | X | | X |
| Mindera Dermal Biomarker Patch Application[4] | X | X | X | X | X | X |
| Adverse Events | X | X | X | X | X | X |
| IP accountability | | X | X | X | X | X |

Abbreviations:
BMI = Body Mass Index;
IP = Investigational Product;
PASI = Psoriasis Area and Severity Index;
PGA = Physician Global Assessment;
BSA = Body Surface Area.
[1] Medical history includes prescription and over-the-counter medication history.
[2] Only applicable to subjects who have not been examined by a rheumatologist or dermatologist within 30 days prior to screening. Height, weight, and BMI are included.
[3] If screening and baseline occur on the same day, clinician must ensure subject has refrained from any topical steroid use 2 weeks prior to the application of the Mindera Dermal Biomarker Patch.
[4] For screening/baseline assessments, the physical exam, PASI, PGA, BSA, and/or Mindera Dermal Biomarker Patch application can be completed at either the screening visit or the baseline visit (PASI, PGA, and BSA should be completed at the same visit and before Mindera Dermal Biomarker Patch application).

Study Population

These studies enrolled both male and female patients who were aged 18 years or older, diagnosed with psoriasis by either a rheumatologist or a dermatologist with at least one identifiable study lesion of 2 cm in diameter or greater, and were planned for treatment with IL-23 inhibitor (IL-23i), IL-17 inhibitor (IL-17i), or TNFα inhibitor (TNFαi) therapy once enrolled in the study. The exclusion criteria included use of topical steroids on the study lesion within 2 weeks prior to the baseline visit and concurrent use of Plaquenil. All study participants were also instructed to refrain from the use of all topical steroids throughout the study until the end of study treatment.

Dermal Biomarker Patch Application

To apply DBPs to the skin, a customized spring-loaded applicator was used. This applicator served to standardize the application pressure across subjects and users. The loaded applicator was placed against the skin and the trigger pressed, applying the patch to the skin. The patch was then held in place against the skin for 5 minutes by a ring of medical tape. After this time, the patch was removed from the subject, immediately placed into storage buffer (LiCl, Triton X-100, Tris-EDTA), and stored at 4° C. until processing.

Dermal Biomarker Patch Processing

Dermal transcriptomes were processed within 96 hours of collection from subjects. The applied DBPs were washed with chilled 1×PBS and then dried under a stream of nitrogen. mRNA extraction from the patch was performed by applying PCR grade water (50 μL, 95° C.) to the DBP. The patch was then heated 1 minute at 95° C. to elute the bound mRNA from the DBP. This eluted mRNA was then converted to cDNA using the Takara SMART-Seq® Single Cell kit according to the manufacturer's instructions. Amplified cDNA samples were then stored at 4° C. until analysis.

Next-Generation Sequencing Procedures

Amplified cDNA was sequenced by a commercial vendor (Psomagen, Inc., Rockville, MD) according to standard procedures. Library preparation was accomplished using Illumina Nextera DNA Flex kits according to the manufacturer's instructions. Prepared indexed libraries were then loaded onto a NovaSeq6000 S4 with read length of 150PE for sequencing of 40 M reads per sample. During sequencing, the quality score (Q30) was maintained over 75%. Upon completion of sequencing runs, FASTQ file quality was checked with FASTQC and trimmed with the Trim_galore program. The trimmed FASTQ files were aligned and mapped to human reference genome GRCh38 using the hisat2 program. The number of reads was counted for each Ensemble gene ID using the FeatureCounts program and Homo sapiens GRCH38.84.gtf. RNA expression analysis was further processed using the Bioconductor package edgeR. Genes were filtered using filterByExpr before logCPM (log counts per million reads) were calculated as a measure of gene expression level. For downstream classifier builds, logCPM values were used.

IL-23 Classifier Development

Five common classifiers were selected and applied for predicting responders under IL-23i treatment using the R package caret. The selected classifiers have been frequently used in the medical field for exploring predictive or prognostic biomarkers and included glmnet (Lasso and Elastic-Net Regularized Generalized Linear Model), PAM (Nearest Shrunken Centroids), LM (Linear Regression Model), SVM (Support Vector Machine), and RF (Random Forest).

The five classifiers were compared for their predictive performance using the following experimental design: 1) the data set was split into ten stratified outer folds; 2) for each of the folds, the data were preprocessed for feature selection. The top 20, 50, or 200 differentially expressed genes (features) were selected using linear regression model; 3) The hyperparameters were tuned in the training set via a ten-fold cross-validation, and the process subsequently repeated five times; 4) Based on the selected hyperparameters, a model was derived from the training set and applied to the test set. Performance metrics on the test set were then calculated. This process was repeated five times for each classifier.

The earliest enrolled IL-23i treated patients in STAMP studies were used for IL-23i classifier training. Baseline PASI filter (none, 6+, 8+, and 10+) were applied to explore the impact of disease severity on classifier performance. Classifier training were performed using the machine learning approaches stated above and test performance was assessed using 10-fold cross validation. IL-23i classifier were locked once a desired performance (>85% PPV and >85% sensitivity) were achieved. The IL-23i treatment patients enrolled after the classifier lock were used as the independent validation set.

IL-17 Classifier Development

Disclosed herein is a list of 17 genes which were predictive of psoriasis patients' response to IL-17i by analyzing a publicly available data set. In brief, moderate to severe psoriasis patients (baseline PASI ≥10) were treated with brodalumab and the patients were followed up for 12 weeks. PASI measurement were performed at baseline and week 12, and patients' treatment response was assessed using week 12 PASI75. Lesional and non-lesional skin biopsy samples were collected at baseline and week 12. RNA profiling was performed using an Affymetrix microarray platform. The lesional samples collected at baseline were used in the predictive biomarker analysis.

The 17 predictive genes were negatively correlating with patients' response to brodalumab. The 17 genes were mapped to 14 Ensemble gene IDs reported in RNASeq data from STAMP studies. The 14-gene classifier was validated in STAMP studies.

TNFai Classifier Development

Publicly available data sets in the NCBI Gene Expression Omnibus (GEO) database and European Bioinformatics Institute (EMBL-EBI) big data database were used as a classifier training data sets. For initial data selection, search terms of psoriasis patients with biologics treatment and transcriptome profiles were used to identify either array or sequencing data.

Supervised predictive biomarker selection was applied to individual training data to filter genes based on the following assessment: 1) correlation between gene expression and patient response; 2) median gene expression level; 3) gene expression dynamic range; 4) difference between average gene expression of responder and non-responders. Ratios of genes down-regulated and gene up-regulated in TNFαi responders were used to develop a prediction of TNFαi treatment responses.

Prospective Classifier Validation

IL-23i, IL-17i and TNFαi classifiers were independently validated using the patients enrolled in STAMP studies. Each classifier discretely predicted a patient as either a responder or non-responder for biologic class. Response was defined as achieving PASI75 at week 12. The cross-tabulation of observed and predicted classes with associated statistics was calculated with the confusionMatrix function of the R caret package.

(a) Characteristics of Study Subjects

Figure 7:
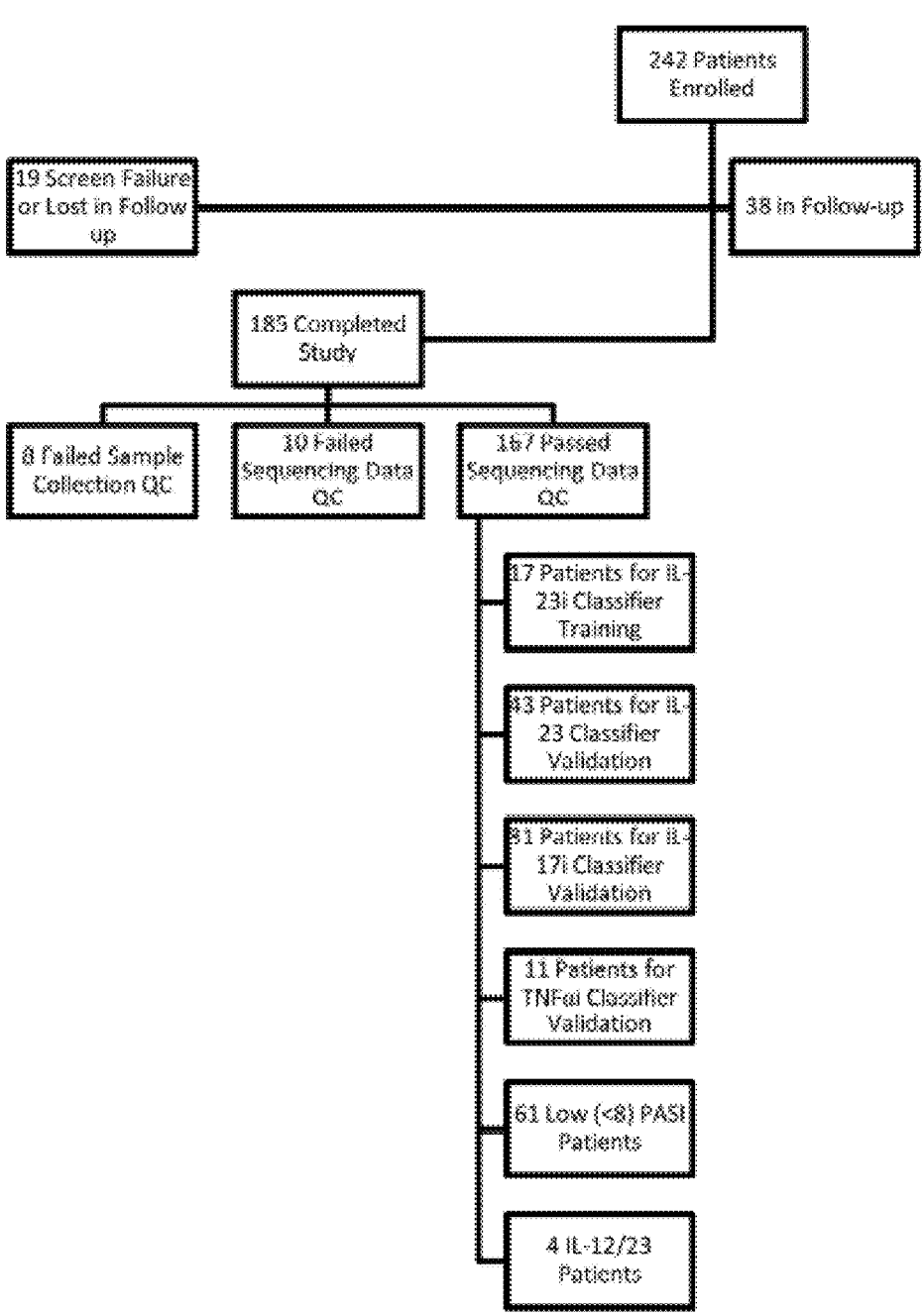
FIG. 7 shows study patient sample enrollment and analysis flow chart.

A total of 242 psoriasis patients were enrolled in the STAMP studies (FIG. 7) at time of data lock, including 38 patients who were still in follow up. STAMP is an actively recruiting study designed to continue enrolling new patients to support psoriasis biomarker research. Varied demographics and clinical features of the study subjects were observed (Table 3). With regard to drug class, 49.6% patients were treated with IL-23i, 33.2% were treated with IL-17i, 14.7% were treated with TNFαi, and 2.5% were treated with IL-12/23i.

TABLE 3

STAMP study patient demographics and disease characteristics.

| | Patient Population (N = 242) |
|---|---|
| Sex | 242 |
| Male | 112 (46.3%) |
| Female | 130 (53.7%) |
| Race | 241 |
| White | 193 (80.1%) |
| Asian | 19 (7.9%) |
| Black or African American | 16 (6.6%) |
| Others | 13 (5.4%) |
| Age | 241 |
| | 48.5 ± 13.7 |
| Body Mass Index | 238 |
| | 31.9 ± 7.0 |
| PASI | 238 |
| | 11.1 ± 9.1 |
| Biologics Class | 238 |
| IL-17 Inhibitor | 79 (33.2%) |
| IL-23 Inhibitor | 118 (49.6%) |
| IL-12/23 Inhibitor | 6 (2.5%) |
| TNFα Inhibitor | 35 (14.7%) |
| Psoriasis Subtypes | 239 |
| Plaque Psoriasis | 226 (94.6%) |
| Psoriatic Arthritis | 9 (3.8%) |
| Others | 4 (1.6%) |
| Prior Biologics History | 214 |

TABLE 3-continued

STAMP study patient demographics and disease characteristics.

| | Patient Population (N = 242) |
|---|---|
| Biologics Naive | 134 (62.6%) |
| Treated with Biologics Within Past 12 Weeks | 50 (23.4%) |
| Treated with Biologics Over 12 Weeks Ago | 30 (14.0%) |

Values are n (%) of patients or mean ± standard deviation

Of the 242 patients initially identified for this study, 185 patients completed the study, meaning that both baseline and week 12 PASI scores were collected, and 57 patients were either screen failures, lost to follow up, or still in follow up. Out of the 185 patients, 177 had baseline DBP samples collected, while 8 patients failed DBP sample collection. Of this subset, 167 samples passed sequencing data QC metrics and were included in the biomarker analysis, with 10 (5.4%, 10/177) samples failing either sample processing or sequencing data QC.

The patient response rate was 64.1% for the whole cohort, and ranged from 47.6% to 72.5% for different biologics (Table 4). High (baseline PASI ≥8) PASI patients had 26.4% higher response rate than low PASI patients across all drug classes.

TABLE 4

Psoriasis Patient Response Rates.

| Biologics | No PASI Filter | PASI ≥ 8 | PASI < 8 |
|---|---|---|---|
| All Biologics | 64.1% (118/184) | 74.3% (84/113) | 47.9% (34/71) |
| IL-23i | 64.1% (68/106) | 70.8% (46/65) | 53.7% (22/41) |
| IL-17i | 72.5% (37/51) | 84.8% (28/33) | 50.0% (9/18) |
| TNFαi | 47.6% (10/21) | 63.6% (7/11) | 30.0% (3/10) |

High (baseline PASI ≥8) PASI patients were used for predictive classifier development and validation. The IL-23i treated patient population was divided into two subsets, 17 IL-23i treated patients were used for training an IL-23i predictive classifier, and the remaining 43 patients were used for prospective validation. All high PASI IL-17i and TNFαi patients were used for the classifier validation.

(b) IL-23i Classifier Development and Performance in Training Set

A subset of 17 IL-23i treated high PASI (>8) patients were used for IL-23i predictive classifier training, including 9 responders and 8 non-responders. The best performing model was built on glmnet using the top 50 features selected with linear regression model. Test performance was assessed with ten-fold cross validation and the positive predictive value (PPV), sensitivity and balanced accuracy were 89.7%, 96.3%, and 91.9%, respectively.

TNFai Data Source and Predictive Biomarker Discovery

Four publicly available datasets (Table 5) were identified and used for the TNFαi response classifier development. A total of 73 patients were included in these datasets, out of which 58 patients had both transcriptome data and outcome assessment data for predictive biomarker discovery. Patient outcome was assessed with PASI75 at week 12 or 16, or histological response.

TABLE 5

Publicly available datasets for TNFαi classifier training.

| ID | Dataset Accession # | Year Published | Treatment | Pt Response Criteria | Sample Size | Transcriptome Profiling Platform |
|---|---|---|---|---|---|---|
| #1 | GSE85034 | 2017 | Adalimumab | PASI75 at WK 16 | 14 | Illumina HumanHT-12 V4.0 expression beadchip |
| #2 | GSE11903 | 2009 | Etanercept | Histological response (epidermal thickness) at WK 12 | 15 | Affymetrix HG-U133A_2 |
| #3 | GSE117239 | 2019 | Etanercept | PASI75 at WK 12 | 34 | Affymetrix HG-U133_Plus_2 |
| #4 | E-MTAB-6556 | 2019 | Etanercept | PASI75 at WK 12 | 10 | RNASeq |

Supervised predictive biomarkers selection was applied to the four training data sets. Nine genes were determined as predictive of TNFαi response in at least two datasets (Table 6). The output of the classifier was a TNFαi response prediction score; in this scoring system, the lower the prediction score, the higher chance the patient will respond to TNFαi treatment. The classifier performance showed PPV, sensitivity and balanced accuracy of 78.9%, 43.1%, and 63.7%, respectively with this training set (Table 7).

TABLE 6

List of the 9 genes identified as correlating to response to anti-α biologics

| Gene Title | Gene Symbol |
|---|---|
| Cornefied Envelope Protein Cornefilin | CNFN |
| Cathepsin C | CTSC |
| Glucosylceramidase Beta Pseudogene 1 | GBAP1 |
| Cellular Retinoic Acid Binding Protein 2 | CRABP2 |
| Protocadherin 7 | PCDH7 |
| Peptidylprolyl Isomerase G | PPIG |
| Ras-related protein Rab-31 | RAB31 |
| Complement component 3 | C3 |
| Early growth response 1 | EGR1 |

TABLE 7

Test performance of TNFαi classifier on the training set.

| | |
|---|---|
| Sample Size | 58 |
| Number of Responder | 34 |
| Number of Non-Responder | 24 |
| PPV | 78.9% |
| NPV | 51.3% |
| Sensitivity | 44.1% |
| Specificity | 83.3% |
| Balanced Accuracy | 63.7% |

Mind.Px Classifier Validation

Figure 8A:
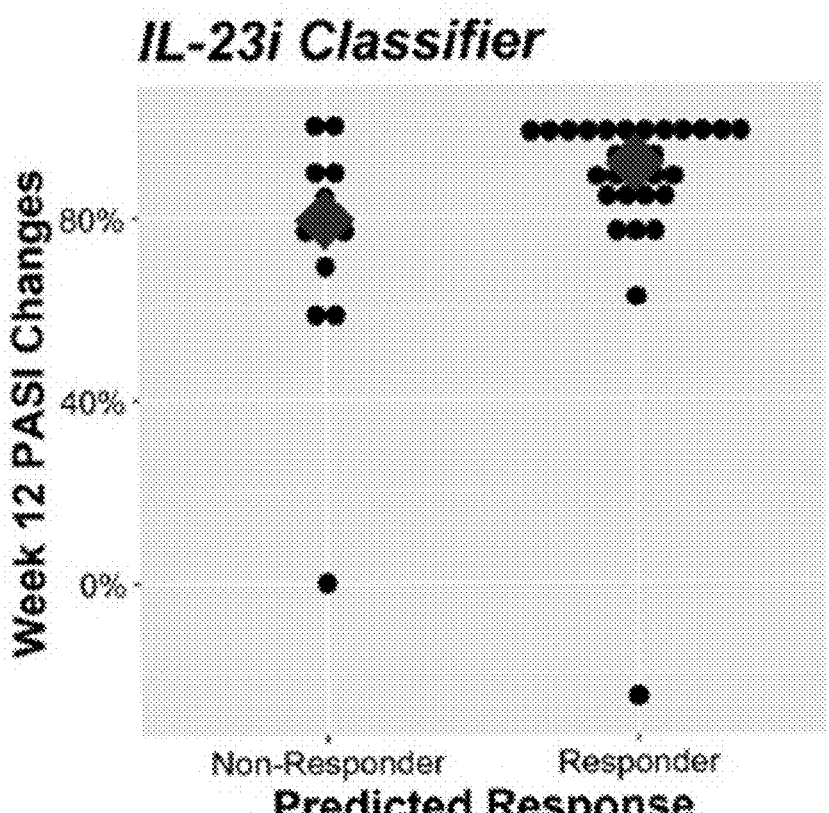
FIGS. 8A-C show correlation between predicted response and patient week 12 PASI changes in psoriasis patients from independent validation data set.
Figure 8B:
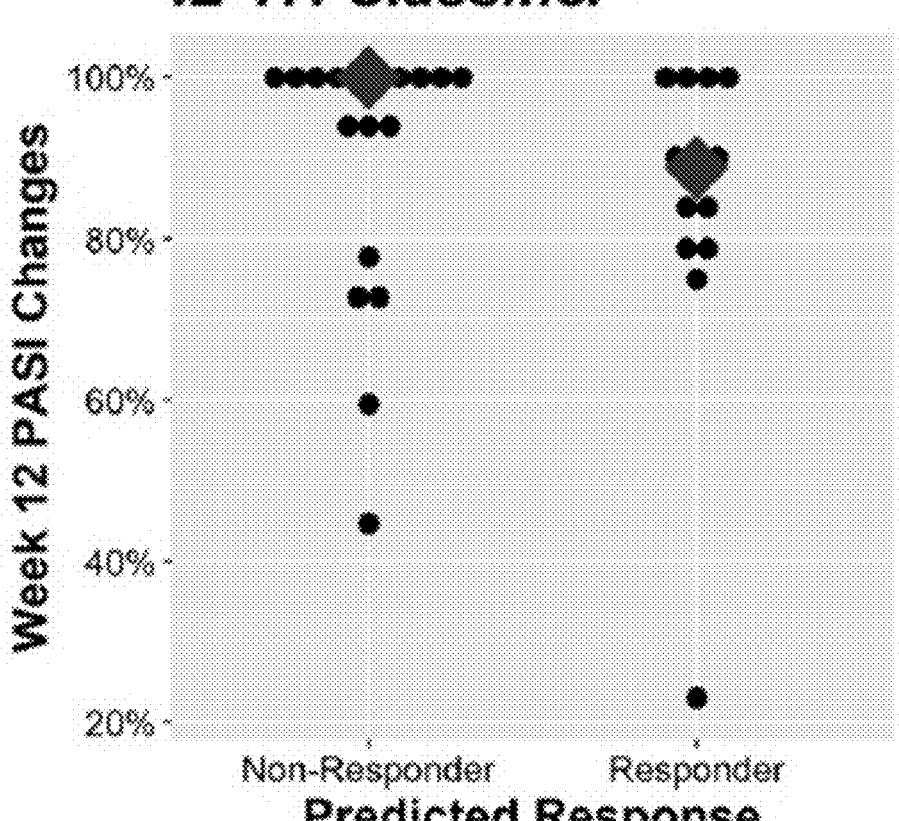
Figure 8C:
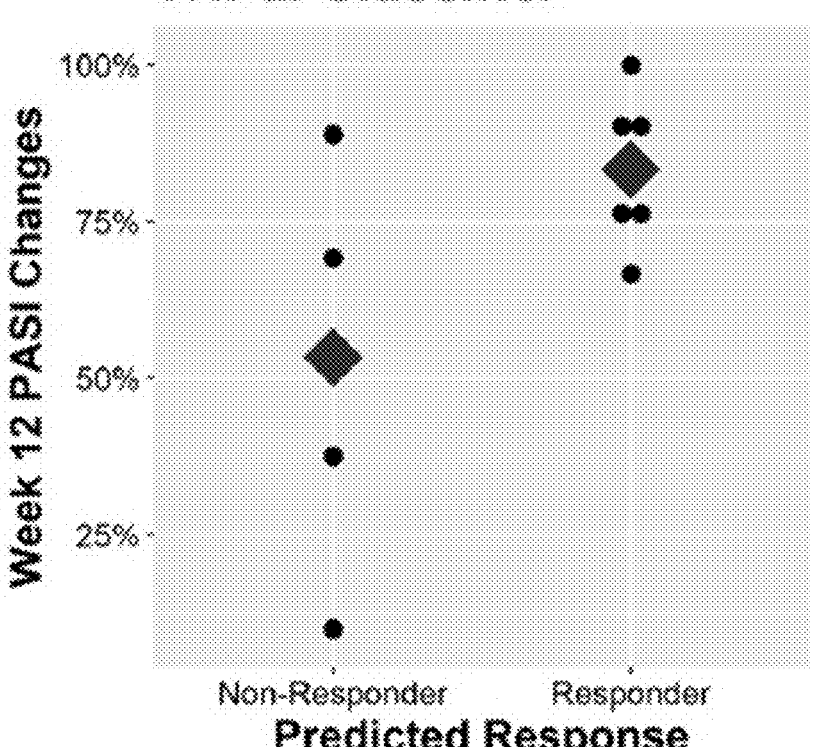

Patient demographics and disease characteristics for the 95 patients included in the prospective validation can be found in Table 8. Only patients with baseline PASI≥8 were included in the validation. For the three classifiers, positive predictive value ranged from 85.7% to 93.1% (Table 9). Correlation between observed W12 PASI changes and predicted drug response were assessed (FIG. 8A-C).

TABLE 8

Classifier Validation Set Patient Demographics and Disease Characteristics

| | IL-23i Classifier (N = 43) | IL-17i Classifier (N = 31) | TNFαi Classifier (N = 11) |
|---|---|---|---|
| Sex | | | |
| Male | 23 (53.5%) | 21 (32.3%) | 4 (36.4%) |
| Female | 20 (46.5%) | 10 (67.7%) | 7 (63.6%) |
| Race | | | |
| White | 35 (81.4%) | 23 (74.2%) | 9 (81.8%) |
| Others | 8 (18.6%) | 8 (25.8%) | 2 (18.2%) |
| Age | | | |
| | 48.3 ± 16.9 | 48.9 ± 12.9 | 47.8 ± 13.4 |
| Body Mass Index | | | |
| | 31.1 ± 7.5 | 32.1 ± 6.3 | 32.6 ± 5.2 |
| PASI | | | |
| | 15.9 ± 8.5 | 17.5 ± 12.6 | 14.8 ± 5.4 |
| Psoriasis Subtypes | | | |
| Plaque Psoriasis | 41 (97.6%) | 31 (96.8%) | 11 (100%) |
| Others | 1 (2.4%) | 1 (3.2%) | 0 (0%) |

TABLE 9

Classifier validation test performance of three classifiers
on patients with baseline PASI ≥ 8.

| Classifier | Sample Size | Number of Responder | Number of Non-Responder | PPV | NPV | Sensitivity | Specificity | Balanced Accuracy |
|---|---|---|---|---|---|---|---|---|
| IL-23i Classifier | 43 | 37 | 6 | 93.1% | 28.6% | 73.0% | 66.7% | 69.8% |
| IL-17i Classifier | 31 | 26 | 5 | 92.3% | 22.2% | 46.2% | 80.0% | 63.1% |
| TNFαi Classifier | 11 | 7 | 4 | 85.7% | 75.0% | 85.7% | 75.0% | 80.4% |

The same analysis was repeated for 66 moderate to severe disease patients (i.e., PASI≥10), and similar overall test performance was observed with PPV ranging from 90% to 100% in this smaller cohort (Table 10).

TABLE 10

Classifier validation test performance of three classifiers on patients with baseline
PASI ≥ 10.

| Classifier | Sample Size | Number of Responder | Number of Non-Responder | PPV | NPV | Sensitivity | Specificity | Balanced Accuracy |
|---|---|---|---|---|---|---|---|---|
| IL-23i Classifier | 35 | 30 | 5 | 95.7% | 33.3% | 73.3% | 80.0% | 76.7% |
| IL-17i Classifier | 22 | 17 | 5 | 90.0% | 33.3% | 52.9% | 80.0% | 66.5% |
| TNFαi Classifier | 9 | 7 | 2 | 100.0% | 66.7% | 85.7% | 100.0% | 92.9% |

Patients with baseline PASI<8 were also analyzed to determine the classifier performance in milder patients. In this case, the balanced accuracy ranged from 44.4% to 52.8% for three classifiers, suggesting that the developed classifier was optimized for moderate to severe psoriasis patients.

Mind.Px Predicted Response Prevalence

Figure 9:
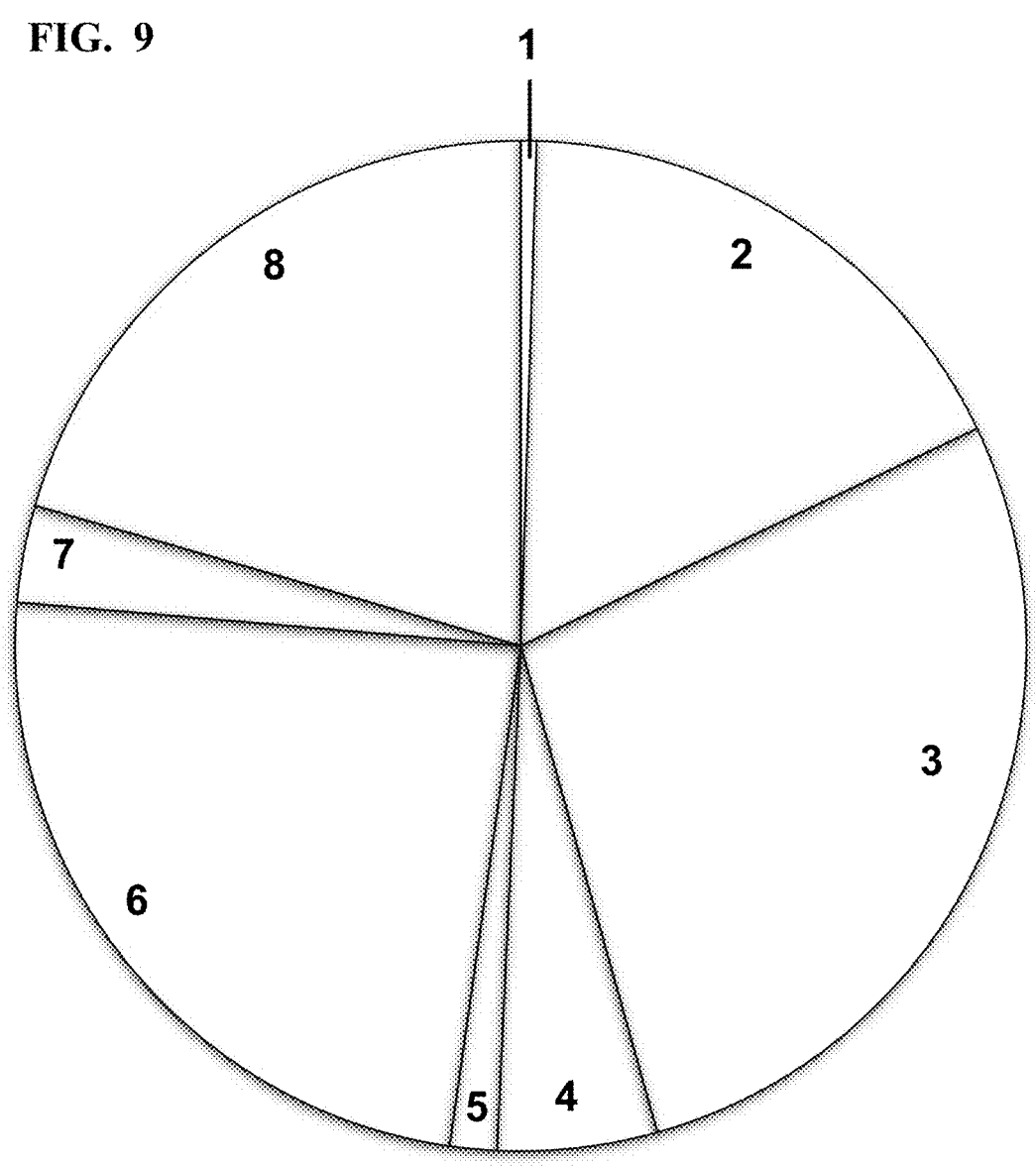
FIG. 9 shows predicted response prevalence in patients enrolled in the study.

The predicted response prevalence of patients by all three classifiers (IL-23i, IL-17i and TNFαi) was assessed using 195 patients who had baseline DBP samples and completed RNASeq sequencing data (FIG. 9 and Table 11). Individually, the predicted response prevalence was 72.3%, 51.7% and 67.1% for IL-23i, IL-17i and TNFαi classifiers, respectively. Critically, 99.5% (194/195) patients were predicted as to responder to at least one of the three drug classes. All possible combinations of the three drug classes were represented with 17.4% (34/195) of patients predicted as a responder to all three drug classes, 56.9% (111/195) of patients predicted as a responder to two of the three drug classes, and 25.1% (49/195) of patients predicted as a responder to one of the three drug classes.

TABLE 11

Mind.Px predicted response prevalence in
patients enrolled in the STAMP studies.

| Class | Number of Patients | Patient Percentage |
|---|---|---|
| Non-Respond to All | 1 | 0.5% |
| Respond to All | 34 | 17.4% |
| Respond to IL17 & IL23 | 54 | 27.7% |

TABLE 11-continued

Mind.Px predicted response prevalence in
patients enrolled in the STAMP studies.

| Class | Number of Patients | Patient Percentage |
|---|---|---|
| Respond to IL17i & TNFαi | 10 | 5.1% |
| Respond to IL23i & TNFαi | 47 | 24.1% |
| Respond to IL23i Only | 6 | 3.1% |
| Respond to IL17i Only | 3 | 1.5% |
| Respond to TNFαi Only | 40 | 20.5% |

STAMP Study Demographics

There were 242 patients included in this analysis, with demographics that largely were consistent with previous studies with respect to gender, race, and age (Table 3). Similarly, the average patient in these studies was obese (BMI>30), with a mean age of 48.5 years. Most interestingly, in this study, the vast majority of patients (86%) were biologic naïve or had not been administered a biologic within the past 12 weeks. Given that many moderate to severe psoriasis patients have been exposed to biologics, this finding was particularly surprising, but analysis of the classifier response of biologic naïve versus biologic exposed patients showed no difference between the predictive value of the algorithms in either of these patient groups.

Classifier Development and Validation

The final IL-23i classifier was developed and validated using patients enrolled in the STAMP studies. A subset of the total IL-23i enrolled patients were used as the training set and the remaining patients in the cohort were used for classifier validation. Since the training and test set were from the same study with the sample and data processed in the same manner, the classifier developed with the training set can be applied to the test set without the need for additional normalization.

The strategy for the development of the IL-17i and TNFαi classifiers was different from the IL-23i classifier. The IL-17i and TNFαi patient sample sizes in STAMP studies were smaller than IL-23i patients and were not sufficient to divide into separate training and test sets, so publicly available datasets were used for the training of these two classifiers. It was noted that the training sets from the public data differed significantly than the test sets in some aspects, including sample collection method (punch biopsy vs. dermal patch), RNA preparation protocol, transcriptome profiling method (array vs. sequencing based). Due to these different natures of the training sets, the training sets primarily were used only for feature selection. Once the predictive genes were identified, a simplified algorithm that utilized gene expression values or the ratio of gene expression values, was applied as the predictive classifier. The cutoffs were preset prior to the validation using percentile data values calculated from the prediction scores of STAMP patients and this allowed for an assessment of classifier performance while minimizing the risk of overfitting.

Here, week 12 PASI75 was used as the patient outcome determination. In a clinical setting where a better response (e.g., PASI 90 or PASI 100) is desired, the classifier can potentially be used for the identification of this group of patients with certain clinical cutoff adjustment. Further classifier development to conclusively identify "super-responders" or "super-non-responders" is ongoing and will be reported in due course.

All three classifiers were validated for baseline PASI ≥8 patients. However, the predictive value of these classifiers in patients with lower starting PASI scores was limited. This could be because the three classifiers were developed with high (≥10) PASI patients as the training set in order to match the types of patients that were enrolled in the pivotal clinical studies for each biologic. It is possible that a mild patient might biologically have different transcriptomic biomarkers. Alternatively, in patients with low starting PASI scores, the reliability of the response determination measure (PASI 75) is low given the reduced dynamic range of the measurement.

Other clinical variables have been previously used to stratify psoriasis patients or have been correlated with poorer outcomes. In particular, BMI and age have been reported as having clinical prognostic value in assessing biologic treatment response. The predictive significance of BMI and age as a possible orthogonal input variable in the classifier is tested. However, adding either variable as a covariate when exploring the predictive models, no improvement was observed in the predictive accuracy or positive predictive value.

The prevalence of the biomarker predicted response revealed key features of this test. Of those tested, only a single patient out of the 195 patients tested was predicted to not respond to any of the three biologic drug classes. These data concur with a widely accepted clinical fact that the treatment and management of psoriasis has dramatically changed since the introduction of biologics; almost all patients will respond to one of the three classes of biologics. However, a disconnect was observed between biologic prescribing behavior and the predicted biologic class from the test. While only 14.7% of the enrollees in the observational STAMP study were prescribed TNFαi biologics (49.6% of the patient cohort), 67% of the patient population was predicted to respond to this class.

Disclosed herein is an actionable machine learning-based precision medicine test that can predict psoriasis patient response to biologics (TNFαi, IL17i, or IL23i) with high positive predictive value, by combining dermal biomarker patch platform with machine learning methods. Interestingly, when the entire patient cohort was examined, almost all patients were predicted to respond to at least one biologic class, highlighting the tremendous efficacy of biologic drugs in treating psoriasis. Using baseline biomarkers combined with machine learning algorithm development, the proper biologic for a given patient can be prescribed the first time. This test could lead to improved patient outcomes while also translating into tremendous cost savings for healthcare systems. It is contemplated that this test can effectively minimize the trial-and-error approach to the biologic treatment of psoriasis, and provide physicians, patients, and payers with a powerful tool to bring personalized medicine to the management of psoriasis patients.

Example 7. Efficient Prediction of Response to Psoriasis Biologics Using a Machine Learning Classifier In the United States, psoriasis affects upward of 3% of the population and treatment can cost from $87,585 to $366,645 annually with the most frequently used drugs. It generally takes 12 to 16 weeks for clinical response to treatment to be meaningful, and efficacy of presently available therapies ranges from 30% to 80%, due at least in part to the inability to predict response to a specific treatment regimen.

An algorithm (Mind.Px) is developed herein for the prediction of response to biologics (anti-IL-17, anti-IL-23) used for the treatment of patients with psoriasis, by comparing baseline transcriptomes with clinical response to biologic drugs at 12 weeks after initial treatment. The 62 patients (out of 75) who responded had Psoriasis Area and Severity Index changes of 0.75 or greater, whereas the non-responders had Psoriasis Area and Severity Index (PASI) changes of −0.2 to 0.75. Cross-validation using linear regression modeling showed a balanced prediction accuracy of 0.71 using PASI75 as the cutoff for evaluating the classifier performance. A positive prediction value of 0.95 was achieved. A total of 17 genes were finalized as correlating with patient response to anti-IL-17 biologics. Alternatively, a prospective classifier was built using patients receiving anti-IL-23 biologics using the same criteria for response (N=17). A total of 27 genes were finalized for use in this classifier and the positive predictive value (PPV) across both classifiers was 100%.

Classifiers for biologic prediction largely utilized orthogonal biomarkers and achieved high PPV. The use of Mind.Px results in better outcomes in patients with psoriasis and significantly reduced costs to the healthcare system.
Human Subject Recruitment and Enrollment Subjects with active psoriasis and lesions >2 cm in diameter were enrolled. All procedures were approved by an independent Institutional Review Board (Integreview, Austin TX) and written consent was obtained from all subjects prior to the study. The study was not powered for statistical significance. For each subject, one Mindera dermal biomarker patch (DBP) was applied to the lesional skin. Samples were immediately placed into vials with storage buffer as per the manufacturer's instructions and placed at 4° C. until processing. Processing occurred as per the Mind.Px kit instructions.

Dermal Biomarker Patch Application

To apply patches to the skin, a customized spring-loaded applicator was used. This applicator served to standardize the application pressure across subjects and across users. The loaded applicator was placed against the skin and the trigger pressed, applying the patch to the skin. The patch was then held in place against the skin for 5 minutes by a ring of medical tape. After this time, the patch was removed from the subject, immediately placed into storage buffer (LiCl, Triton X-100, Tris-EDTA), and stored at 4° C. until processing.

Dermal Biomarker Patch Processing

Dermal transcriptomes were processed within 72 hours of collection from subjects. Samples were prepared by washing the applied DBP with chilled 1×PBS and then drying the patch under a stream of nitrogen. The dried DBP was then place on a heat block preset to 95° C. for 1 minute, at which time, 50 μL of PCR grade water previously heated to 95° C. was then applied to the microneedle array for 1 minute to elute the bound mRNA from the DBP. This eluted mRNA was then converted to cDNA using Takara SMART-Seq® Single Cell kit according to the manufacturer's instructions. Amplified cDNA samples were then stored at 4° C. until qPCR or NGS analysis.

Sequencing Procedures

Amplified cDNA was sequenced by a commercial vendor (Psomagen, Inc., Rockville, MD) according to standard procedures. Library preparation was accomplished using Illumina Nextera DNA Flex kits according to the manufacturer's instructions. Prepared indexed libraries were then loaded onto a NovaSeq6000 S4 with read length of 150PE for sequencing of 40 M reads per sample. During sequencing, the quality score (Q30) was maintained over 75%. Upon completion of runs, FASTQ file quality was checked with FASTQC and trimmed with the Trim_galore program. The trimmed FASTQ were aligned and mapped to human reference genome GRCh38 using hisat2 program. The number of reads was counted for each Ensemble gene ID using FeatureCounts program and *Homo sapiens* GRCH38.84.gtf RNA expression analysis was further processed using Bioconductor package edgeR. Genes were filtered using filterByExpr before logCPM (counts per million reads) were calculated. Plots were made with ggplot2 and heatmap.2 functions in R. Percent of genes detected was determined using the ratio of genes detected (with ≥0 count) over the total number of Ensemble genes.

Bioinformatic Procedures

The Mind.Px algorithm has been implemented as an R-script on the DNAnexus® system (Mountain View, CA), a cloud-based data analysis and management platform for DNA sequencing data. Cutoff points for anti-IL-17 and anti-IL-23 response prediction have been defined and implemented in the R-script.

Data were collected from three phase 3 randomized clinical trials: AMAGINE-1, AMAGINE-2, and AMAGINE-3. The endpoint was PASI 75 at week 12. Biopsy samples were collected from lesional areas. Transcriptome analyses were conducted for biopsy samples using the Affymetrix platform. A total of 75 patients were treated with brodalumab, including 62 responders (83%); and 12 non-responders (16%). A total of 17 patients enrolled in the Mindera-sponsored STAMP (Study Through the Application of the Mindera Patch) trial were also included in the analysis (STAMP is an ongoing clinical trial sponsored by Mindera Corp.) The enrollment included patients with psoriasis who were to be treated with either anti-IL-17 or anti-IL-23 biologics. RNA samples were collected from patients' skin prior to therapy and multiple times post-therapy for the identification of molecular biomarkers that could predict patient response to the therapy. Baseline samples were collected from all patients.

Figure 10:
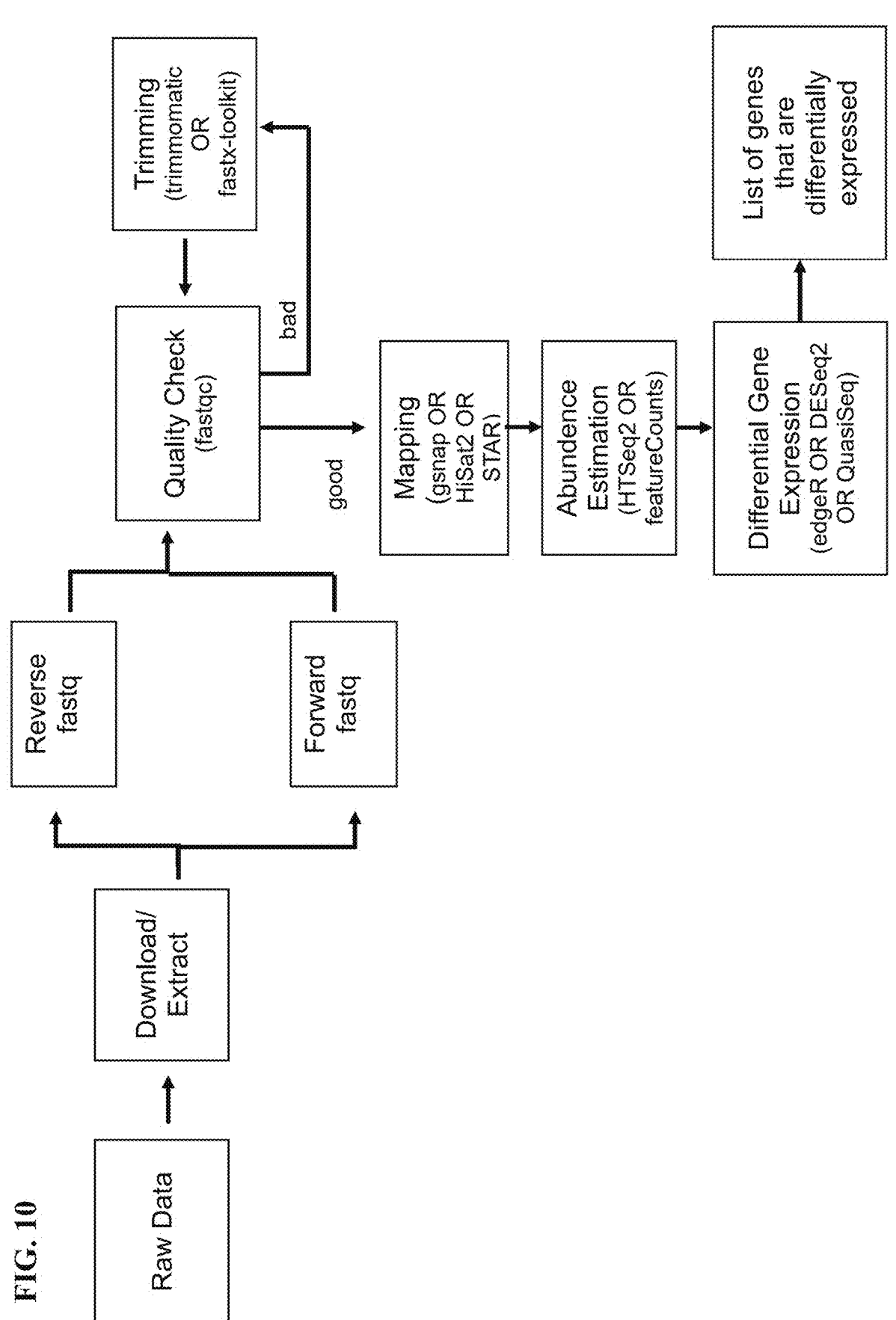
FIG. 10 shows overview of RNA-Seq Analysis.

Post-sequencing, RNA-Seq FASTQ files were trimmed with the Trim_galore Program, which was followed by mapping to human reference genome GRCh38 using the HISAT2 Program. The number of reads was counted for each Ensemble gene ID using the FeatureCounts Program, and human GRCh38.84.gtf RNA expression analysis was further processed using bioconductor package edgeR. Genes were filtered using filterByExpr before logCPM (counts per million reads) was calculated. Plots were made with ggplot2 and heatmap.2 functions compared with the standard R function. The percent of genes detected was determined using the ratio of genes detected (with ≥0 count) divided by the total number of Ensemble genes. The overview of RNA-Seq analysis is summarized in FIG. 10.

Dermal Biomarker Patch Platform Data

Disclosed herein is platform that allows for simple, rapid, and painless extraction of RNA from the skin using a dermal biomarker patch. Subsequent next-generation sequencing of the extracted RNA has allowed us to take a genetic and transcriptomic snapshot of the skin at the exact moment of the test. This rich patient-specific data set can then be analyzed by machine-learning algorithms to ask sophisticated questions of the data (e.g., predicting the appropriate biologic drug for a patient prior to therapeutic selection and treatment).

Figure 11:
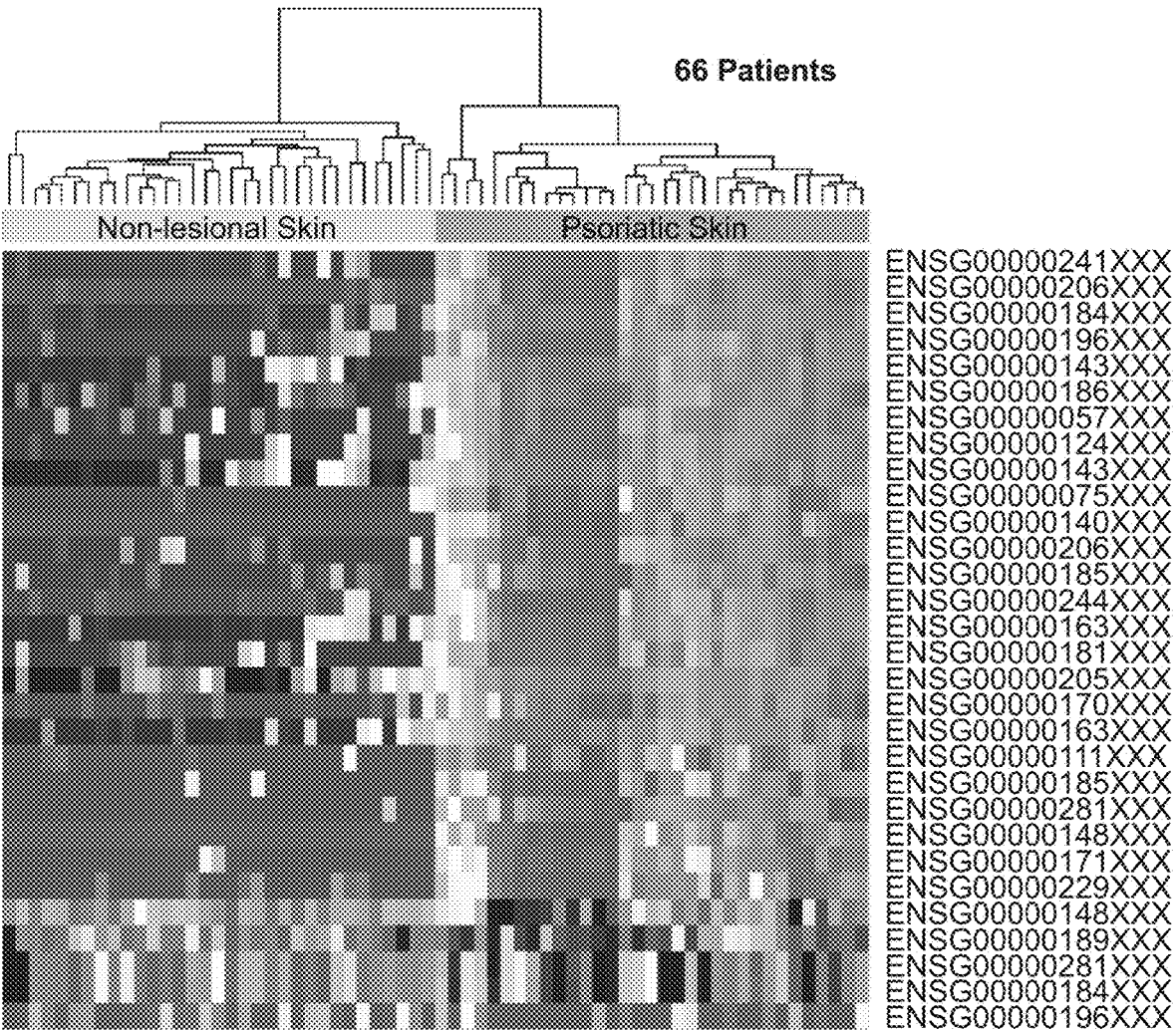
FIG. 11 Lesional versus non-lesional samples compared using Mindera patches versus punch biopsies from 66 patients in the Mindera database.

Lesional vs non-lesional samples were compared using Mindera patches versus punch biopsies from 66 patients in the Mindera database (FIG. 11). The entire transcriptome was analyzed by performing a paired t-test between lesional and non-lesional skin, and then plotting the heatmap for data that have the highest variance (e.g., best P value between the groups). Importantly, the biomarker data were equivalent between the Mindera patch samples and the punch biopsy samples. The 30 highest variance genes were selected, and unsupervised clustering was performed for visualization, showing excellent discrimination between lesional and non-lesional skin in the same patient.

Also disclosed herein is an algorithm for the prediction of response to biologics (anti-IL-17, anti-IL-23) treatment in patients with psoriasis. The data set from Tomalin et al (2020) was used for the identification of genes whose RNA expression levels correlate with the responses to treatment with anti-IL-17 biologics in patients with psoriasis.

In this cohort, 62 patients (out of 75) who responded had PASI changes of ≥0.75, whereas the non-responders had PASI changes of −0.2 to 0.75. The data set was pre-filtered using the differentially expressed genes for psoriasis (lesional vs non-lesional) to minimize the chances of overfitting. Cross-validation using linear regression modeling showed a balanced prediction accuracy of 0.71 using PASI 75 as the cutoff for evaluating the classifier performance. Importantly, a positive prediction value of 0.95 was achieved. A total of 17 genes were finalized as correlating with patient response to brodalumab treatment using StepAIC (Akaike Information Criteria) linear regression modeling (Table 12). The Akaike information criterion is an estimator of out-of-sample prediction error and thereby relative quality of statistical models for a given set of data. Akaike information criterion estimates the relative amount of information lost by a given model: the less information a model loses, the higher the quality of that model.

TABLE 12

List of the 17 genes identified as correlating to response to anti-IL17 biologics

| Affy ID | Gene Title | Gene Symbol |
|---------|------------|-------------|
| 210413_x_at | serpin peptidase inhibitor, clade B (ovalbumin), member 3///serpin peptidase inhibitor, clade B (ovalbumin), member 4 | SERPINB3/// SERPINB4 |
| 232170 at | S100 calcium binding protein A7A | S100A7A |
| 209719_x_at | serpin peptidase inhibitor, clade B (ovalbumin), member 3 | SERPINB3 |
| 203691_at | peptidase inhibitor 3, skin-derived | PI3 |
| 209125_at | keratin 6A | KRT6A |
| 212531_at | lipocalin 2 | LCN2 |
| 207356_at | defensin, beta 4A///defensin, beta 4B | DEFB4A//DEFB4B |
| 214549_x_at | small proline-rich protein 1A | SPRR1A |
| 220322 at | interleukin 36, gamma | IL36G |
| 202086_at | myxovirus (influenza virus) resistance 1, interferon-inducible protein p78 (mouse) | MX1 |
| 202411_at | interferon, alpha-inducible protein 27 | IFI27 |
| 206488_s_at | CD36 molecule (thrombospondin receptor) | CD36 |
| 209555_s_at | CD36 molecule (thrombospondin receptor) | CD36 |
| 208650_s_at | CD24 molecule | CD24 |
| 208651_x_at | CD24 molecule | CD24 |
| 266_s_at | CD24 molecule | CD24 |
| 203233_at | interleukin 4 receptor | IL4R |

A heatmap was generated from expression data for these 17 genes (FIG. 12). Each column is a baseline sample collected from a patient. From left to right the patients were sorted by low to high PASI changes. The dark grey bar on the top shows the 12 non-responders (W12 PASI changes <0.75); the light grey bar shows the 62 responders (W12 PASI changes >0.75). As shown in the heatmap, a subset of responder patients (far right) had strong down-regulation (dark grey to black) of most of genes, suggesting the potential of using these 17 genes to predict patient response to anti-IL-17 treatment. The down-regulation of these 17 genes indicated the better responses to treatment, whereas the up-regulation indicated the worse responses.

An identical analysis was performed prospectively using patients receiving anti-IL-23 biologics. This cohort was derived from patients enrolling in the STAMP trial conducted by Mindera. In this cohort of 17 patients, 5 patients had achieved PASI-75 response by 12 weeks, while 12 patients did not achieve this level of response. Cross-validation using regression modeling showed a balanced prediction accuracy of 0.70 using PASI 75 as the cutoff for evaluating the classifier performance. Importantly, a positive prediction value of 1.00 was achieved. A total of 50 genes were finalized as correlating with patient response to anti-IL-23 biologic treatment (Table 13).

TABLE 13

List of the 50 genes identified as correlating to response to anti-IL23 biologics

| Ensembl Gene ID | Gene Symbol |
|-----------------|-------------|
| ENSG00000237973 | MTCO1P12 |
| ENSG00000248527 | MTATP6P1 |
| ENSG00000171603 | CLSTN1 |
| ENSG00000162493 | PDPN |
| ENSG00000187942 | LDLRAD2 |
| ENSG00000241720 | AL158847.1 |
| ENSG00000134202 | GSTM3 |
| ENSG00000169509 | CRCT1 |
| ENSG00000235942 | LCE6A |
| ENSG00000135916 | ITM2C |
| ENSG00000170275 | CRTAP |
| ENSG00000145040 | UCN2 |

TABLE 13-continued

List of the 50 genes identified as correlating to response to anti-IL23 biologics

| Ensembl Gene ID | Gene Symbol |
|-----------------|-------------|
| ENSG00000073282 | TP63 |
| ENSG00000124882 | EREG |
| ENSG00000173221 | GLRX |
| ENSG00000134986 | NREP |
| ENSG00000197948 | FCHSD1 |
| ENSG00000151914 | DST |
| ENSG00000078399 | HOXA9 |
| ENSG00000091136 | LAMB1 |
| ENSG00000101825 | MXRA5 |
| ENSG00000186918 | ZNF395 |
| ENSG00000019549 | SNAI2 |
| ENSG00000159899 | NPR2 |
| ENSG00000137098 | SPAG8 |
| ENSG00000160360 | GPSM1 |
| ENSG00000175274 | TP53I11 |
| ENSG00000165912 | PACSIN3 |
| ENSG00000077498 | TYR |
| ENSG00000036672 | USP2 |
| ENSG00000108179 | PPIF |
| ENSG00000271880 | AGAP11 |
| ENSG00000151303 | AL136982.1 |
| ENSG00000261011 | AL136982.4 |
| ENSG00000229969 | AL136982.2 |
| ENSG00000271573 | AL136982.5 |
| ENSG00000170430 | MGMT |
| ENSG00000197757 | HOXC6 |
| ENSG00000198056 | PRIM1 |
| ENSG00000139233 | LLPH |
| ENSG00000084110 | HAL |
| ENSG00000198431 | TXNRD1 |
| ENSG00000257732 | AC089983.1 |
| ENSG00000255150 | EID3 |
| ENSG00000165799 | RNASE7 |
| ENSG00000129562 | DAD1 |
| ENSG00000184916 | JAG2 |
| ENSG00000140859 | KIFC3 |
| ENSG00000103056 | SMPD3 |
| ENSG00000161714 | PLCD3 |

Disclosed herein is a platform that utilizes a simple, minimally invasive patch that takes a painless biomarker sample from a patient with psoriasis in a matter of minutes. The Mind.Px test has the ability to collect patient data at scale and, when combined with high-precision molecular testing, results in a powerful platform with excellent sensitivity and specificity. Use of this platform can potentially translate into huge cost savings for healthcare systems, particularly when applied to the prediction of response to expensive treatments-effectively eliminating the present trial-and-error approach to the treatment of psoriasis.

Biomarkers captured using Mind.Px include DNA, RNA, proteins, and small molecules. In particular, the role of RNA in chronic skin diseases, which is well characterized, has been exploited to provide the missing predictive link between a patient's genetic markers and responsiveness to different drug classes. By capturing RNA from a patient's psoriatic lesion, next-generation sequencing is used to evaluate more than 7000 biomarkers per test sample. The results of this biomarker analysis can be used by healthcare providers and payers to predict an individual patient's response to a class of biologic drugs, by the mechanism of action of that class of agent, to optimize treatment selection. The use of Mind.Px could result in better outcomes and significantly reduced costs to the healthcare system.

Analysis of the classifiers developed in this study demonstrated high positive predictive value in assessing if a patient will respond to biologic drug prior to initial exposure. Indeed, in both classifiers, >90% positive predictive value could be achieved, which could significantly impact medical practice and the treatment of psoriasis patients. Interestingly, comparison of the biomarker sets between algorithms showed some overlap (at least 2 genes overlap between the anti-IL-17 and anti-IL-23 classifier).

Table 14. List of the genes that can be used as classifies to determine the effectiveness of one or more biologics for treating psoriasis. In some embodiments, the methods disclosed herein directed to determining whether a subject suffering from psoriasis will positively respond to an IL-17, IL-23, or TNFα mediated treatment, further comprise determining the presence, absence, or expression level of at least 5 genes selected from Table 14. In some embodiments, the methods further comprise determining the presence, absence, or expression level of at least 6 genes selected from Table 14 to 17 genes selected from Table 14. In some embodiments, the methods further comprise determining the presence, absence, or expression level of at least 6 genes selected from Table 14 to 7 genes selected from Table 14, 6 genes selected from Table 14 to 8 genes selected from Table 14, 6 genes selected from Table 14 to 9 genes selected from Table 14, 6 genes selected from Table 14 to 10 genes selected from Table 14, 6 genes selected from Table 14 to 11 genes selected from Table 14, 6 genes selected from Table 14 to 12 genes selected from Table 14, 6 genes selected from Table 14 to 13 genes selected from Table 14, 6 genes selected from Table 14 to 14 genes selected from Table 14, 6 genes selected from Table 14 to 15 genes selected from Table 14, 6 genes selected from Table 14 to 16 genes selected from Table 14, 6 genes selected from Table 14 to 17 genes selected from Table 14, 7 genes selected from Table 14 to 8 genes selected from Table 14, 7 genes selected from Table 14 to 9 genes selected from Table 14, 7 genes selected from Table 14 to 10 genes selected from Table 14, 7 genes selected from Table 14 to 11 genes selected from Table 14, 7 genes selected from Table 14 to 12 genes selected from Table 14, 7 genes selected from Table 14 to 13 genes selected from Table 14, 7 genes selected from Table 14 to 14 genes selected from Table 14, 7 genes selected from Table 14 to 15 genes selected from Table 14, 7 genes selected from Table 14 to 16 genes selected from Table 14, 7 genes selected from Table 14 to 17 genes selected from Table 14, 8 genes selected from Table 14 to 9 genes selected from Table 14, 8 genes selected from Table 14 to 10 genes selected from Table 14, 8 genes selected from Table 14 to 11 genes selected from Table 14, 8 genes selected from Table 14 to 12 genes selected from Table 14, 8 genes selected from Table 14 to 13 genes selected from Table 14, 8 genes selected from Table 14 to 14 genes selected from Table 14, 8 genes selected from Table 14 to 15 genes selected from Table 14, 8 genes selected from Table 14 to 16 genes selected from Table 14, 8 genes selected from Table 14 to 17 genes selected from Table 14, 9 genes selected from Table 14 to 10 genes selected from Table 14, 9 genes selected from Table 14 to 11 genes selected from Table 14, 9 genes selected from Table 14 to 12 genes selected from Table 14, 9 genes selected from Table 14 to 13 genes selected from Table 14, 9 genes selected from Table 14 to 14 genes selected from Table 14, 9 genes selected from Table 14 to 15 genes selected from Table 14, 9 genes selected from Table 14 to 16 genes selected from Table 14, 9 genes selected from Table 14 to 17 genes selected from Table 14, 10 genes selected from Table 14 to 11 genes selected from Table 14, 10 genes selected from Table 14 to 12 genes selected from Table 14, 10 genes selected from Table 14 to 13 genes selected from Table 14, 10 genes selected from Table 14 to 14 genes selected from Table 14, 10 genes selected from Table 14 to 15 genes selected from Table 14, 10 genes selected from Table 14 to 16 genes selected from Table 14, 10 genes selected from Table 14 to 17 genes selected from Table 14, 11 genes selected from Table 14 to 12 genes selected from Table 14, 11 genes selected from Table 14 to 13 genes selected from Table 14, 11 genes selected from Table 14 to 14 genes selected from Table 14, 11 genes selected from Table 14 to 15 genes selected from Table 14, 11 genes selected from Table 14 to 16 genes selected from Table 14, 11 genes selected from Table 14 to 17 genes selected from Table 14, 12 genes selected from Table 14 to 13 genes selected from Table 14, 12 genes selected from Table 14 to 14 genes selected from Table 14, 12 genes selected from Table 14 to 15 genes selected from Table 14, 12 genes selected from Table 14 to 16 genes selected from Table 14, 12 genes selected from Table 14 to 17 genes selected from Table 14, 13 genes selected from Table 14 to 14 genes selected from Table 14, 13 genes selected from Table 14 to 15 genes selected from Table 14, 13 genes selected from Table 14 to 16 genes selected from Table 14, 13 genes selected from Table 14 to 17 genes selected from Table 14, 14 genes selected from Table 14 to 15 genes selected from Table 14, 14 genes selected from Table 14 to 16 genes selected from Table 14, 14 genes selected from Table 14 to 17 genes selected from Table 14, 15 genes selected from Table 14 to 16 genes selected from Table 14, 15 genes selected from Table 14 to 17 genes selected from Table 14, or 16 genes selected from Table 14 to 17 genes selected from Table 14. In some embodiments, the methods further comprise determining the presence, absence, or expression level of at least 6 genes selected from Table 14, 7 genes selected from Table 14, 8 genes selected from Table 14, 9 genes selected from Table 14, 10 genes selected from Table 14, 11 genes selected from Table 14, 12 genes selected from Table 14, 13 genes selected from Table 14, 14 genes selected from Table 14, 15 genes selected from Table 14, 16 genes selected from Table 14, or 17 genes selected from Table 14. In some embodiments, the methods further comprise determining the presence, absence, or expression level of at least at least 6 genes selected from Table 14, 7 genes selected from Table 14, 8 genes selected from Table 14, 9 genes selected from Table 14, 10 genes selected from Table 14, 11 genes selected from Table 14, 12 genes selected from Table 14, 13 genes selected from Table 14, 14 genes selected from Table 14, 15 genes selected from Table 14, or 16 genes selected from Table 14. In some embodiments, the methods further comprise determining the presence, absence, or expression level of at least at most 7 genes selected from Table 14, 8 genes selected from Table 14, 9 genes selected from Table 14, 10 genes selected from Table 14, 11 genes selected from Table 14, 12 genes selected from Table 14, 13 genes selected from Table 14, 14 genes selected from Table 14, 15 genes selected from Table 14, 16 genes selected from Table 14, or 17 genes selected from Table 14. In some embodiments, the methods further comprise determining the presence, absence, or expression level of at least 20 genes selected from Table 14 to 50 genes selected from Table 14. In some embodiments, the methods further comprise determining the presence, absence, or expression level of at least 20 genes selected from Table 14 to 25 genes selected from Table 14, 20 genes selected from Table 14 to 30 genes selected from Table 14, 20 genes selected from Table 14 to 35 genes selected from Table 14, 20 genes selected from Table 14 to 40 genes selected from Table 14, 20 genes selected from Table 14 to 45 genes selected from Table 14, 20 genes selected from Table 14 to 50 genes selected from Table 14, 25 genes selected from Table 14 to 30 genes selected from Table 14, 25 genes selected from Table 14 to 35 genes selected from Table 14, 25 genes selected from Table 14 to 40 genes selected from Table 14, 25 genes selected from Table 14 to 45 genes selected from Table 14, 25 genes selected from Table 14 to 50 genes selected from Table 14, 30 genes selected from Table 14 to 35 genes selected from Table 14, 30 genes selected from Table 14 to 40 genes selected from Table 14, 30 genes selected from Table 14 to 45 genes selected from Table 14, 30 genes selected from Table 14 to 50 genes selected from Table 14, 35 genes selected from Table 14 to 40 genes selected from Table 14, 35 genes selected from Table 14 to 45 genes selected from Table 14, 35 genes selected from Table 14 to 50 genes selected from Table 14, 40 genes selected from Table 14 to 45 genes selected from Table 14, 40 genes selected from Table 14 to 50 genes selected from Table 14, or 45 genes selected from Table 14 to 50 genes selected from Table 14. In some embodiments, the methods further comprise determining the presence, absence, or expression level of at least 20 genes selected from Table 14, 25 genes selected from Table 14, 30 genes selected from Table 14, 35 genes selected from Table 14, 40 genes selected from Table 14, 45 genes selected from Table 14, or 50 genes selected from Table 14. In some embodiments, the methods further comprise determining the presence, absence, or expression level of at least at least 20 genes selected from Table 14, 25 genes selected from Table 14, 30 genes selected from Table 14, 35 genes selected from Table 14, 40 genes selected from Table 14, or 45 genes selected from Table 14. In some embodiments, the methods further comprise determining the presence, absence, or expression level of at least at most 25 genes selected from Table 14, 30 genes selected from Table 14, 35 genes selected from Table 14, 40 genes selected from Table 14, 45 genes selected from Table 14, or 50 genes selected from Table 14.

TABLE 14

| AffyID | Gene Symbol | PublicID | EnsemblGeneID | Gene Regulation in Psoriasis |
|---|---|---|---|---|
| 1405_i_at | CCL5 | M21121 | ENSG00000271503 | Up-regulated in Psoriasis |
| 1552312_a_at | MFAP3 | NM_005927 | ENSG00000037749 | Up-regulated in Psoriasis |
| 1552378_s_at | RDH10 | NM_172037 | ENSG00000121039 | Up-regulated in Psoriasis |
| 1552480_s_at | PTPRC | NM_080923 | ENSG00000081237 | Up-regulated in Psoriasis |
| 1552497_a_at | SLAMF6 | NM_052931 | ENSG00000162739 | Up-regulated in Psoriasis |
| 1552536_at | VTI1A | NM_145206 | ENSG00000151532 | Up-regulated in Psoriasis |
| 1552639_at | KLHDC7B | NM_138433 | ENSG00000130487 | Up-regulated in Psoriasis |
| 1552671_a_at | SLC9A7 | NM_032591 | ENSG00000065923 | Up-regulated in Psoriasis |
| 1552980_at | HAS3 | NM_138612 | ENSG00000103044 | Up-regulated in Psoriasis |
| 1553055_a_at | SLFN5 | NM_144975 | ENSG00000166750 | Up-regulated in Psoriasis |
| 1553081_at | WFDC12 | NM_080869 | ENSG00000168703 | Up-regulated in Psoriasis |
| 1553102_a_at | CCDC69 | BC016647 | ENSG00000198624 | Up-regulated in Psoriasis |
| 1553423_a_at | SLFN13 | NM_144682 | ENSG00000154760 | Up-regulated in Psoriasis |
| 1553514_a_at | VNN3 | NM_078625 | ENSG00000093134 | Up-regulated in Psoriasis |
| 1553589_a_at | PDZK1IP1 | NM_005764 | ENSG00000162366 | Up-regulated in Psoriasis |
| 1553602_at | MUCL1 | NM_058173 | ENSG00000172551 | Up-regulated in Psoriasis |
| 1553695_a_at | NLRX1 | NM_170722 | ENSG00000160703 | Up-regulated in Psoriasis |
| 1553906_s_at | FGD2 | NM_173558 | ENSG00000146192 | Up-regulated in Psoriasis |
| 1554008_at | OSMR | BC010943 | ENSG00000145623 | Up-regulated in Psoriasis |
| 1554016_a_at | USB1 | BC006291 | ENSG00000103005 | Up-regulated in Psoriasis |
| 1554079_at | GALNT18 | BC037341 | ENSG00000110328 | Up-regulated in Psoriasis |
| 1554119_at | USB1 | BC010099 | ENSG00000103005 | Up-regulated in Psoriasis |
| 1554240_a_at | ITGAL | BC008777 | ENSG00000005844 | Up-regulated in Psoriasis |
| 1554406_a_at | CLEC7A | BC013385 | ENSG00000172243 | Up-regulated in Psoriasis |
| 1554440_at | KIAA0513 | BC030280 | ENSG00000135709 | Up-regulated in Psoriasis |
| 1554452_a_at | HILPDA | BC001863 | ENSG00000135245 | Up-regulated in Psoriasis |
| 1554462_a_at | DNAJB9 | AF115512 | ENSG00000128590 | Up-regulated in Psoriasis |
| 1554676_at | SRGN | BC022313 | ENSG00000122862 | Up-regulated in Psoriasis |
| 1554707_at | SPATA6L | BC034293 | ENSG00000106686 | Up-regulated in Psoriasis |
| 1554708_s_at | SPATA6L | BC034293 | ENSG00000106686 | Up-regulated in Psoriasis |
| 1554724_at | SLC6A11 | BC036083 | ENSG00000132164 | Up-regulated in Psoriasis |
| 1554795_a_at | FBLIM1 | BC019895 | ENSG00000162458 | Up-regulated in Psoriasis |
| 1554807_a_at | SPIRE1 | BC016825 | ENSG00000134278 | Up-regulated in Psoriasis |
| 1554822_at | PHTF2 | BC022419 | ENSG00000006576 | Up-regulated in Psoriasis |
| 1554899_s_at | FCER1G | BC020763 | ENSG00000158869 | Up-regulated in Psoriasis |
| 1554903_at | FRMD8 | BC033851 | ENSG00000126391 | Up-regulated in Psoriasis |
| 1554905_x_at | FRMD8 | BC033851 | ENSG00000126391 | Up-regulated in Psoriasis |
| 1554906_a_at | MPHOSPH6 | BC029395 | ENSG00000135698 | Up-regulated in Psoriasis |
| 1554914_at | PLA2G4D | BC034571 | ENSG00000159337 | Up-regulated in Psoriasis |
| 1554920_at | SCEL | BC020726 | ENSG00000136155 | Down-regulated in Psoriasis |

TABLE 14-continued

| AffyID | Gene Symbol | PublicID | EnsemblGeneID | Gene Regulation in Psoriasis |
|---|---|---|---|---|
| 1554921_a_at | SCEL | BC020726 | ENSG00000136155 | Down-regulated in Psoriasis |
| 1555019_at | CDHR1 | BC038799 | ENSG00000148600 | Down-regulated in Psoriasis |
| 1555120_at | CD96 | BC020749 | ENSG00000153283 | Up-regulated in Psoriasis |
| 1555167_s_at | NAMPT | BC020691 | ENSG00000105835 | Up-regulated in Psoriasis |
| 1555213_a_at | CLEC7A | AF400602 | ENSG00000172243 | Up-regulated in Psoriasis |
| 1555214_a_at | CLEC7A | AF400602 | ENSG00000172243 | Up-regulated in Psoriasis |
| 1555292_at | STRIP2 | BC019064 | ENSG00000128578 | Up-regulated in Psoriasis |
| 1555326_a_at | ADAM9 | AF495383 | ENSG00000168615 | Up-regulated in Psoriasis |
| 1555407_s_at | FGD3 | BC032232 | ENSG00000127084 | Up-regulated in Psoriasis |
| 1555416_a_at | ALOX15B | AF468053 | ENSG00000179593 | Up-regulated in Psoriasis |
| 1555464_at | IFIH1 | BC046208 | ENSG00000115267 | Up-regulated in Psoriasis |
| 1555480_a_at | FBLIM1 | AF459643 | ENSG00000162458 | Up-regulated in Psoriasis |
| 1555628_a_at | HAVCR2 | BC020843 | ENSG00000135077 | Up-regulated in Psoriasis |
| 1555638_a_at | SAMSN1 | AF519621 | ENSG00000155307 | Up-regulated in Psoriasis |
| 1555745_a_at | LYZ | U25677 | ENSG00000090382 | Up-regulated in Psoriasis |
| 1555756_a_at | CLEC7A | AF400600 | ENSG00000172243 | Up-regulated in Psoriasis |
| 1555759_a_at | CCL5 | AF043341 | ENSG00000271503 | Up-regulated in Psoriasis |
| 1555778_a_at | POSTN | AY140646 | ENSG00000133110 | Down-regulated in Psoriasis |
| 1556122_at | RAB11B-AS1 | CA431092 | ENSG00000269386 | Up-regulated in Psoriasis |
| 1556123_a_at | RAB11B-AS1 | CA431092 | ENSG00000269386 | Up-regulated in Psoriasis |
| 1556263_s_at | PWRN1 | AK058147 | ENSG00000259905 | Up-regulated in Psoriasis |
| 1556346_at | COTL1 | AJ227860 | ENSG00000103187 | Up-regulated in Psoriasis |
| 1556606_at | NAV2 | BU739339 | ENSG00000166833 | Up-regulated in Psoriasis |
| 1557049_at | BTBD19 | BQ183759 | ENSG00000222009 | Up-regulated in Psoriasis |
| 1557078_at | SLFN5 | AK054668 | ENSG00000166750 | Up-regulated in Psoriasis |
| 1557116_at | APOL6 | BM980001 | ENSG00000221963 | Up-regulated in Psoriasis |
| 1557236_at | APOL6 | BF512806 | ENSG00000221963 | Up-regulated in Psoriasis |
| 1557275_a_at | TLCD2 | BF726849 | ENSG00000185561 | Up-regulated in Psoriasis |
| 1557285_at | AREG | AI891075 | ENSG00000109321 | Up-regulated in Psoriasis |
| 1557309_at | DENND1B | BC016588 | ENSG00000213047 | Up-regulated in Psoriasis |
| 1557389_at | SH3PXD2A-AS1 | AK056784 | ENSG00000280693 | Up-regulated in Psoriasis |
| 1557458_s_at | SHB | BU685917 | ENSG00000107338 | Up-regulated in Psoriasis |
| 1557609_s_at | TBC1D12 | AW188458 | ENSG00000108239 | Up-regulated in Psoriasis |
| 1557636_a_at | C7orf57 | BC031107 | ENSG00000164746 | Up-regulated in Psoriasis |
| 1557890_at | STXBP5-AS1 | BC035182 | ENSG00000233452 | Up-regulated in Psoriasis |
| 1558105_a_at | SLC9A7 | AK096921 | ENSG00000065923 | Up-regulated in Psoriasis |
| 1558201_s_at | SLC4A1AP | AI889922 | ENSG00000163798 | Up-regulated in Psoriasis |
| 1558217_at | SLFN13 | AK074465 | ENSG00000154760 | Up-regulated in Psoriasis |
| 1558290_a_at | PVT1 | BG200951 | ENSG00000249859 | Up-regulated in Psoriasis |
| 1558393_at | KRT7 | BC042076 | ENSG00000135480 | Up-regulated in Psoriasis |
| 1558407_at | PLEKHG2 | AK095957 | ENSG00000090924 | Up-regulated in Psoriasis |
| 1558549_s_at | VNN1 | BG120535 | ENSG00000112299 | Up-regulated in Psoriasis |
| 1558561_at | HM13 | AK074686 | ENSG00000101294 | Up-regulated in Psoriasis |
| 1558678_s_at | MALAT1 | BE708432 | ENSG00000251562 | Up-regulated in Psoriasis |
| 1558846_at | PNLIPRP3 | AL833418 | ENSG00000203837 | Up-regulated in Psoriasis |
| 1559018_at | PTPRE | AL832042 | ENSG00000132334 | Up-regulated in Psoriasis |
| 1559263_s_at | ZC3H12D | BG397809 | ENSG00000178199 | Up-regulated in Psoriasis |
| 1559268_at | ADAM23 | AW022638 | ENSG00000114948 | Up-regulated in Psoriasis |
| 1559501_at | CBR3-AS1 | BC037580 | ENSG00000236830 | Up-regulated in Psoriasis |
| 1559585_at | DDX60L | AK096369 | ENSG00000181381 | Up-regulated in Psoriasis |
| 1559883_s_at | SAMHD1 | AF147427 | ENSG00000101347 | Up-regulated in Psoriasis |
| 1559917_a_at | CBR3-AS1 | AB004851 | ENSG00000236830 | Up-regulated in Psoriasis |
| 1561080_at | TXNRD1 | BC042974 | ENSG00000198431 | Up-regulated in Psoriasis |
| 1561336_at | DNASE1L3 | CA449306 | ENSG00000163687 | Up-regulated in Psoriasis |
| 1561948_at | COQ10B | AI793340 | ENSG00000115520 | Up-regulated in Psoriasis |
| 1562364_at | GVINP1 | AL833700 | ENSG00000254838 | Up-regulated in Psoriasis |
| 1562460_at | CNDP2 | BF512616 | ENSG00000133313 | Up-regulated in Psoriasis |
| 1564031_a_at | RELL2 | AK054889 | ENSG00000164620 | Up-regulated in Psoriasis |
| 1564573_at | IFITM10 | BC036199 | ENSG00000244242 | Up-regulated in Psoriasis |
| 1565657_at | CMTM6 | BC042995 | ENSG00000091317 | Up-regulated in Psoriasis |
| 1566901_at | TGIF1 | AL832409 | ENSG00000177426 | Up-regulated in Psoriasis |
| 1569003_at | VMP1 | AL541655 | ENSG00000062716 | Up-regulated in Psoriasis |
| 1569149_at | PDLIM7 | BC023629 | ENSG00000196923 | Up-regulated in Psoriasis |
| 1569150_x_at | PDLIM7 | BC023629 | ENSG00000196923 | Up-regulated in Psoriasis |
| 1569555_at | GDA | BC012859 | ENSG00000119125 | Up-regulated in Psoriasis |
| 1569617_at | OSBP2 | BC018025 | ENSG00000184792 | Up-regulated in Psoriasis |
| 200628_s_at | WARS | M61715 | ENSG00000140105 | Up-regulated in Psoriasis |
| 200629_at | WARS | NM_004184 | ENSG00000140105 | Up-regulated in Psoriasis |
| 200648_s_at | GLUL | NM_002065 | ENSG00000135821 | Up-regulated in Psoriasis |
| 200670_at | XBP1 | NM_005080 | ENSG00000100219 | Up-regulated in Psoriasis |
| 200708_at | GOT2 | NM_002080 | ENSG00000125166 | Up-regulated in Psoriasis |
| 200766_at | CTSD | NM_001909 | ENSG00000117984 | Up-regulated in Psoriasis |
| 200776_s_at | BZW1 | AL518328 | ENSG00000082153 | Up-regulated in Psoriasis |
| 200777_s_at | BZW1 | NM_014670 | ENSG00000082153 | Up-regulated in Psoriasis |
| 200790_at | ODC1 | NM_002539 | ENSG00000115758 | Up-regulated in Psoriasis |
| 200812_at | CCT7 | NM_006429 | ENSG00000135624 | Up-regulated in Psoriasis |
| 200831_s_at | SCD | AA678241 | ENSG00000099194 | Up-regulated in Psoriasis |
| 200832_s_at | SCD | AB032261 | ENSG00000099194 | Up-regulated in Psoriasis |

TABLE 14-continued

| AffyID | Gene Symbol | PublicID | EnsemblGeneID | Gene Regulation in Psoriasis |
|---|---|---|---|---|
| 200886_s_at | PGAM1 | NM_002629 | ENSG00000171314 | Up-regulated in Psoriasis |
| 200887_s_at | STAT1 | NM_007315 | ENSG00000115415 | Up-regulated in Psoriasis |
| 200900_s_at | M6PR | AI583537 | ENSG00000003056 | Up-regulated in Psoriasis |
| 200901_s_at | M6PR | NM_002355 | ENSG00000003056 | Up-regulated in Psoriasis |
| 200923_at | LGALS3BP | NM_005567 | ENSG00000108679 | Up-regulated in Psoriasis |
| 200935_at | CALR | NM_004343 | ENSG00000179218 | Up-regulated in Psoriasis |
| 200989_at | HIF1A | NM_001530 | ENSG00000100644 | Up-regulated in Psoriasis |
| 200998_s_at | CKAP4 | AW029619 | ENSG00000136026 | Up-regulated in Psoriasis |
| 200999_s_at | CKAP4 | NM_006825 | ENSG00000136026 | Up-regulated in Psoriasis |
| 201012_at | ANXA1 | NM_000700 | ENSG00000135046 | Up-regulated in Psoriasis |
| 201037_at | PFKP | NM_002627 | ENSG00000067057 | Up-regulated in Psoriasis |
| 201118_at | PGD | NM_002631 | ENSG00000142657 | Up-regulated in Psoriasis |
| 201195_s_at | SLC7A5 | AB018009 | ENSG00000103257 | Up-regulated in Psoriasis |
| 201242_s_at | ATP1B1 | BC000006 | ENSG00000143153 | Up-regulated in Psoriasis |
| 201243_s_at | ATP1B1 | NM_001677 | ENSG00000143153 | Up-regulated in Psoriasis |
| 201252_at | PSMC4 | NM_006503 | ENSG00000013275 | Up-regulated in Psoriasis |
| 201266_at | TXNRD1 | NM_003330 | ENSG00000198431 | Up-regulated in Psoriasis |
| 201348_at | GPX3 | NM_002084 | ENSG00000211445 | Up-regulated in Psoriasis |
| 201435_s_at | EIF4E | AW268640 | ENSG00000151247 | Up-regulated in Psoriasis |
| 201436_at | EIF4E | AI742789 | ENSG00000151247 | Up-regulated in Psoriasis |
| 201437_s_at | EIF4E | NM_001968 | ENSG00000151247 | Up-regulated in Psoriasis |
| 201469_s_at | SHC1 | AI809967 | ENSG00000160691 | Up-regulated in Psoriasis |
| 201482_at | QSOX1 | NM_002826 | ENSG00000116260 | Up-regulated in Psoriasis |
| 201483_s_at | SUPT4H1 | BC002802 | ENSG00000213246 | Up-regulated in Psoriasis |
| 201484_at | SUPT4H1 | NM_003168 | ENSG00000213246 | Up-regulated in Psoriasis |
| 201487_at | CTSC | NM_001814 | ENSG00000109861 | Up-regulated in Psoriasis |
| 201489_at | PPIF | BC005020 | ENSG00000108179 | Up-regulated in Psoriasis |
| 201490_s_at | PPIF | NM_005729 | ENSG00000108179 | Up-regulated in Psoriasis |
| 201510_at | ELF3 | AF017307 | ENSG00000163435 | Up-regulated in Psoriasis |
| 201531_at | ZFP36 | NM_003407 | ENSG00000128016 | Up-regulated in Psoriasis |
| 201564_s_at | FSCN1 | NM_003088 | ENSG00000075618 | Up-regulated in Psoriasis |
| 201594_s_at | PPP4R1 | NM_005134 | ENSG00000154845 | Up-regulated in Psoriasis |
| 201631_s_at | IER3 | NM_003897 | ENSG00000137331 | Up-regulated in Psoriasis |
| 201649_at | UBE2L6 | NM_004223 | ENSG00000156587 | Up-regulated in Psoriasis |
| 201695_s_at | PNP | NM_000270 | ENSG00000198805 | Up-regulated in Psoriasis |
| 201739_at | SGK1 | NM_005627 | ENSG00000118515 | Up-regulated in Psoriasis |
| 201754_at | COX6C | NM_004374 | ENSG00000164919 | Up-regulated in Psoriasis |
| 201858_s_at | SRGN | J03223 | ENSG00000122862 | Up-regulated in Psoriasis |
| 201859_at | SRGN | NM_002727 | ENSG00000122862 | Up-regulated in Psoriasis |
| 201860_s_at | PLAT | NM_000930 | ENSG00000104368 | Up-regulated in Psoriasis |
| 201884_at | CEACAM5 | NM_004363 | ENSG00000105388 | Up-regulated in Psoriasis |
| 201890_at | RRM2 | BE966236 | ENSG00000171848 | Up-regulated in Psoriasis |
| 201945_at | FURIN | NM_002569 | ENSG00000140564 | Up-regulated in Psoriasis |
| 201999_s_at | DYNLT1 | NM_006519 | ENSG00000146425 | Up-regulated in Psoriasis |
| 202081_at | IER2 | NM_004907 | ENSG00000160888 | Up-regulated in Psoriasis |
| 202082_s_at | SEC14L1 | AV748469 | ENSG00000129657 | Up-regulated in Psoriasis |
| 202083_s_at | SEC14L1 | AI017770 | ENSG00000129657 | Up-regulated in Psoriasis |
| 202084_s_at | SEC14L1 | NM_003003 | ENSG00000129657 | Up-regulated in Psoriasis |
| 202086_at | MX1 | NM_002462 | ENSG00000157601 | Up-regulated in Psoriasis |
| 202100_at | RALB | BG169673 | ENSG00000144118 | Up-regulated in Psoriasis |
| 202101_s_at | RALB | NM_002881 | ENSG00000144118 | Up-regulated in Psoriasis |
| 202112_at | VWF | NM_000552 | ENSG00000110799 | Up-regulated in Psoriasis |
| 202266_at | TDP2 | NM_016614 | ENSG00000111802 | Up-regulated in Psoriasis |
| 202269_x_at | GBP1 | BC002666 | ENSG00000117228 | Up-regulated in Psoriasis |
| 202270_at | GBP1 | NM_002053 | ENSG00000117228 | Up-regulated in Psoriasis |
| 202284_s_at | CDKN1A | NM_000389 | ENSG00000124762 | Up-regulated in Psoriasis |
| 202345_s_at | FABP5 | NM_001444 | ENSG00000164687 | Up-regulated in Psoriasis |
| 202376_at | SERPINA3 | NM_001085 | ENSG00000196136 | Up-regulated in Psoriasis |
| 202381_at | ADAM9 | NM_003816 | ENSG00000168615 | Up-regulated in Psoriasis |
| 202391_at | BASP1 | NM_006317 | ENSG00000176788 | Up-regulated in Psoriasis |
| 202411_at | IFI27 | NM_005532 | ENSG00000165949 | Up-regulated in Psoriasis |
| 202430_s_at | PLSCR1 | NM_021105 | ENSG00000188313 | Up-regulated in Psoriasis |
| 202446_s_at | PLSCR1 | AI825926 | ENSG00000188313 | Up-regulated in Psoriasis |
| 202459_s_at | LPIN2 | U55968 | ENSG00000101577 | Up-regulated in Psoriasis |
| 202460_s_at | LPIN2 | NM_014646 | ENSG00000101577 | Up-regulated in Psoriasis |
| 202497_x_at | SLC2A3 | AI631159 | ENSG00000059804 | Up-regulated in Psoriasis |
| 202498_s_at | SLC2A3 | BE550486 | ENSG00000059804 | Up-regulated in Psoriasis |
| 202499_s_at | SLC2A3 | NM_006931 | ENSG00000059804 | Up-regulated in Psoriasis |
| 202510_s_at | TNFAIP2 | NM_006291 | ENSG00000185215 | Up-regulated in Psoriasis |
| 202524_s_at | SPOCK2 | NM_014767 | ENSG00000107742 | Up-regulated in Psoriasis |
| 202525_at | PRSS8 | NM_002773 | ENSG00000052344 | Up-regulated in Psoriasis |
| 202531_at | IRF1 | NM_002198 | ENSG00000125347 | Up-regulated in Psoriasis |
| 202557_at | HSPA13 | AI718418 | ENSG00000155304 | Up-regulated in Psoriasis |
| 202558_s_at | HSPA13 | NM_006948 | ENSG00000155304 | Up-regulated in Psoriasis |
| 202575_at | CRABP2 | NM_001878 | ENSG00000143320 | Up-regulated in Psoriasis |
| 202594_at | LEPROTL1 | NM_015344 | ENSG00000104660 | Up-regulated in Psoriasis |
| 202595_s_at | LEPROTLI | AF161461 | ENSG00000104660 | Up-regulated in Psoriasis |
| 202625_at | LYN | AI356412 | ENSG00000254087 | Up-regulated in Psoriasis |

TABLE 14-continued

| AffyID | Gene Symbol | PublicID | EnsemblGeneID | Gene Regulation in Psoriasis |
|---|---|---|---|---|
| 202626_s_at | LYN | NM_002350 | ENSG00000254087 | Up-regulated in Psoriasis |
| 202637_s_at | ICAM1 | AI608725 | ENSG00000090339 | Up-regulated in Psoriasis |
| 202638_s_at | ICAM1 | NM_000201 | ENSG00000090339 | Up-regulated in Psoriasis |
| 202655_at | MANF | NM_006010 | ENSG00000145050 | Up-regulated in Psoriasis |
| 202687_s_at | TNFSF10 | U57059 | ENSG00000121858 | Up-regulated in Psoriasis |
| 202688_at | TNFSF10 | NM_003810 | ENSG00000121858 | Up-regulated in Psoriasis |
| 202728_s_at | LTBP1 | AI986120 | ENSG00000049323 | Up-regulated in Psoriasis |
| 202729_s_at | LTBP1 | NM_000627 | ENSG00000049323 | Up-regulated in Psoriasis |
| 202787_s_at | MAPKAPK3 | U43784 | ENSG00000114738 | Up-regulated in Psoriasis |
| 202788_at | MAPKAPK3 | NM_004635 | ENSG00000114738 | Up-regulated in Psoriasis |
| 202804_at | ABCC1 | AI539710 | ENSG00000103222 | Up-regulated in Psoriasis |
| 202805_s_at | ABCC1 | NM_004996 | ENSG00000103222 | Up-regulated in Psoriasis |
| 202831_at | GPX2 | NM_002083 | ENSG00000176153 | Up-regulated in Psoriasis |
| 202842_s_at | DNAJB9 | AL080081 | ENSG00000128590 | Up-regulated in Psoriasis |
| 202843_at | DNAJB9 | NM_012328 | ENSG00000128590 | Up-regulated in Psoriasis |
| 202859_x_at | CXCL8 | NM_000584 | ENSG00000169429 | Up-regulated in Psoriasis |
| 202869_at | OAS1 | NM_016816 | ENSG00000089127 | Up-regulated in Psoriasis |
| 202887_s_at | DDIT4 | NM_019058 | ENSG00000168209 | Up-regulated in Psoriasis |
| 202888_s_at | ANPEP | NM_001150 | ENSG00000166825 | Up-regulated in Psoriasis |
| 202901_x_at | CTSS | BC002642 | ENSG00000163131 | Up-regulated in Psoriasis |
| 202902_s_at | CTSS | NM_004079 | ENSG00000163131 | Up-regulated in Psoriasis |
| 202917_s_at | S100A8 | NM_002964 | ENSG00000143546 | Up-regulated in Psoriasis |
| 202934_at | HK2 | AI761561 | ENSG00000159399 | Up-regulated in Psoriasis |
| 202952_s_at | ADAM12 | NM_003474 | ENSG00000148848 | Up-regulated in Psoriasis |
| 202957_at | HCLS1 | NM_005335 | ENSG00000180353 | Up-regulated in Psoriasis |
| 202988_s_at | RGS1 | NM_002922 | ENSG00000090104 | Up-regulated in Psoriasis |
| 203002_at | AMOTL2 | NM_016201 | ENSG00000114019 | Up-regulated in Psoriasis |
| 203010_at | STAT5A | NM_003152 | ENSG00000126561 | Up-regulated in Psoriasis |
| 203021_at | SLPI | NM_003064 | ENSG00000124107 | Up-regulated in Psoriasis |
| 203132_at | RB1 | NM_000321 | ENSG00000139687 | Up-regulated in Psoriasis |
| 203153_at | IFIT1 | NM_001548 | ENSG00000185745 | Up-regulated in Psoriasis |
| 203180_at | ALDH1A3 | NM_000693 | ENSG00000184254 | Up-regulated in Psoriasis |
| 203201_at | PMM2 | NM_000303 | ENSG00000140650 | Up-regulated in Psoriasis |
| 203233_at | IL4R | NM_000418 | ENSG00000077238 | Up-regulated in Psoriasis |
| 203234_at | UPP1 | NM_003364 | ENSG00000183696 | Up-regulated in Psoriasis |
| 203252_at | CDK2AP2 | NM_005851 | ENSG00000167797 | Up-regulated in Psoriasis |
| 203256_at | CDH3 | NM_001793 | ENSG00000062038 | Up-regulated in Psoriasis |
| 203261_at | DCTN6 | NM_006571 | ENSG00000104671 | Up-regulated in Psoriasis |
| 203313_s_at | TGIF1 | NM_003244 | ENSG00000177426 | Up-regulated in Psoriasis |
| 203315_at | NCK2 | BC000103 | ENSG00000071051 | Up-regulated in Psoriasis |
| 203363_s_at | ATG13 | AU153525 | ENSG00000175224 | Up-regulated in Psoriasis |
| 203364_s_at | ATG13 | NM_014741 | ENSG00000175224 | Up-regulated in Psoriasis |
| 203367_at | DUSP14 | NM_007026 | ENSG00000276023 | Up-regulated in Psoriasis |
| 203369_x_at | PDLIM7 | AI825846 | ENSG00000196923 | Up-regulated in Psoriasis |
| 203370_s_at | PDLIM7 | NM_005451 | ENSG00000196923 | Up-regulated in Psoriasis |
| 203416_at | CD53 | NM_000560 | ENSG00000143119 | Up-regulated in Psoriasis |
| 203423_at | RBP1 | NM_002899 | ENSG00000114115 | Up-regulated in Psoriasis |
| 203470_s_at | PLEK | AI433595 | ENSG00000115956 | Up-regulated in Psoriasis |
| 203471_s_at | PLEK | NM_002664 | ENSG00000115956 | Up-regulated in Psoriasis |
| 203499_at | EPHA2 | NM_004431 | ENSG00000142627 | Up-regulated in Psoriasis |
| 203507_at | CD68 | NM_001251 | ENSG00000129226 | Up-regulated in Psoriasis |
| 203535_at | S100A9 | NM_002965 | ENSG00000163220 | Up-regulated in Psoriasis |
| 203550_s_at | FAM189B | NM_006589 | ENSG00000160767 | Up-regulated in Psoriasis |
| 203560_at | GGH | NM_003878 | ENSG00000137563 | Up-regulated in Psoriasis |
| 203595_s_at | IFIT5 | N47725 | ENSG00000152778 | Up-regulated in Psoriasis |
| 203596_s_at | IFIT5 | NM_012420 | ENSG00000152778 | Up-regulated in Psoriasis |
| 203663_s_at | COX5A | NM_004255 | ENSG00000178741 | Up-regulated in Psoriasis |
| 203665_at | HMOX1 | NM_002133 | ENSG00000100292 | Up-regulated in Psoriasis |
| 203691_at | PI3 | NM_002638 | ENSG00000124102 | Up-regulated in Psoriasis |
| 203710_at | ITPR1 | NM_002222 | ENSG00000150995 | Up-regulated in Psoriasis |
| 203740_at | MPHOSPH6 | NM_005792 | ENSG00000135698 | Up-regulated in Psoriasis |
| 203757_s_at | CEACAM6 | BC005008 | ENSG00000086548 | Up-regulated in Psoriasis |
| 203779_s_at | MPZL2 | NM_005797 | ENSG00000149573 | Up-regulated in Psoriasis |
| 203780_at | MPZL2 | AF275945 | ENSG00000149573 | Up-regulated in Psoriasis |
| 203797_at | VSNL1 | AF039555 | ENSG00000163032 | Up-regulated in Psoriasis |
| 203798_s_at | VSNL1 | NM_003385 | ENSG00000163032 | Up-regulated in Psoriasis |
| 203821_at | HBEGF | NM_001945 | ENSG00000113070 | Up-regulated in Psoriasis |
| 203858_s_at | COX10 | NM_001303 | ENSG00000006695 | Up-regulated in Psoriasis |
| 203894_at | TUBG2 | NM_016437 | ENSG00000037042 | Up-regulated in Psoriasis |
| 203897_at | LYRM1 | BE963444 | ENSG00000102897 | Up-regulated in Psoriasis |
| 203915_at | CXCL9 | NM_002416 | ENSG00000138755 | Up-regulated in Psoriasis |
| 203922_s_at | CYBB | AI308863 | ENSG00000165168 | Up-regulated in Psoriasis |
| 203923_s_at | CYBB | NM_000397 | ENSG00000165168 | Up-regulated in Psoriasis |
| 203978_at | NUBP1 | NM_002484 | ENSG00000103274 | Up-regulated in Psoriasis |
| 204014_at | DUSP4 | NM_001394 | ENSG00000120875 | Up-regulated in Psoriasis |
| 204015_s_at | DUSP4 | BC002671 | ENSG00000120875 | Up-regulated in Psoriasis |
| 204057_at | IRF8 | AI073984 | ENSG00000140968 | Up-regulated in Psoriasis |
| 204058_at | ME1 | AL049699 | ENSG00000065833 | Up-regulated in Psoriasis |

TABLE 14-continued

| AffyID | Gene Symbol | PublicID | EnsemblGeneID | Gene Regulation in Psoriasis |
|---|---|---|---|---|
| 204059_s_at | ME1 | NM_002395 | ENSG00000065833 | Up-regulated in Psoriasis |
| 204094_s_at | TSC22D2 | NM_014779 | ENSG00000196428 | Up-regulated in Psoriasis |
| 204095_s_at | ELL | AL521391 | ENSG00000105656 | Up-regulated in Psoriasis |
| 204096_s_at | ELL | AL136771 | ENSG00000105656 | Up-regulated in Psoriasis |
| 204116_at | IL2RG | NM_000206 | ENSG00000147168 | Up-regulated in Psoriasis |
| 204137_at | GPR137B | NM_003272 | ENSG00000077585 | Up-regulated in Psoriasis |
| 204153_s_at | MFNG | NM_002405 | ENSG00000100060 | Up-regulated in Psoriasis |
| 204166_at | SBNO2 | NM_014963 | ENSG00000064932 | Up-regulated in Psoriasis |
| 204169_at | IMPDH1 | NM_000883 | ENSG00000106348 | Up-regulated in Psoriasis |
| 204174_at | ALOX5AP | NM_001629 | ENSG00000132965 | Up-regulated in Psoriasis |
| 204205_at | APOBEC3G | NM_021822 | ENSG00000239713 | Up-regulated in Psoriasis |
| 204232_at | FCER1G | NM_004106 | ENSG00000158869 | Up-regulated in Psoriasis |
| 204351_at | S100P | NM_005980 | ENSG00000163993 | Up-regulated in Psoriasis |
| 204357_s_at | LIMK1 | NM_002314 | ENSG00000106683 | Up-regulated in Psoriasis |
| 204385_at | KYNU | NM_003937 | ENSG00000115919 | Up-regulated in Psoriasis |
| 204415_at | IFI6 | NM_022873 | ENSG00000126709 | Up-regulated in Psoriasis |
| 204420_at | FOSL1 | BG251266 | ENSG00000175592 | Up-regulated in Psoriasis |
| 204439_at | IFI44L | NM_006820 | ENSG00000137959 | Up-regulated in Psoriasis |
| 204440_at | CD83 | NM_004233 | ENSG00000112149 | Up-regulated in Psoriasis |
| 204465_s_at | INA | NM_004692 | ENSG00000148798 | Up-regulated in Psoriasis |
| 204470_at | CXCL1 | NM_001511 | ENSG00000163739 | Up-regulated in Psoriasis |
| 204502_at | SAMHD1 | NM_015474 | ENSG00000101347 | Up-regulated in Psoriasis |
| 204529_s_at | TOX | AI961231 | ENSG00000198846 | Up-regulated in Psoriasis |
| 204530_s_at | TOX | NM_014729 | ENSG00000198846 | Up-regulated in Psoriasis |
| 204546_at | KIAA0513 | NM_014732 | ENSG00000135709 | Up-regulated in Psoriasis |
| 204580_at | MMP12 | NM_002426 | ENSG00000262406 | Up-regulated in Psoriasis |

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

The invention claimed is:

1. A method of treating a human subject with psoriasis, comprising:

(a) obtaining RNA molecules from a lesional skin of the human subject with psoriasis by applying a microneedle device to the lesional skin of the human subject, wherein the microneedle device comprises one or more nucleic acids probes that are capable of hybridizing to the RNA molecules, wherein the human subject has not been administered an IL-23 inhibitor prior to the obtaining the RNA molecules;

(b) assaying the obtained RNA molecules in order to identify expression levels of MTCO1P12, MTATP6P1, CLSTN1, PDPN, LDLRAD2, AL158847.1, GSTM3, CRCT1, LCE6A, ITM2C, CRTAP, UCN2, TP63, EREG, GLRX, NREP, FCHSD1, DST, HOXA9, LAMB1, MXRA5, ZNF395, SNAI2, NPR2, SPAG8, GPSM1, TP53111, PACSIN3, TYR, USP2, PPIF, AGAP11, AL136982.1, AL136982.4, AL136982.2, AL136982.5, MGMT, HOXC6, PRIM1, LLPH, HAL, TXNRD1, AC089983.1, EID3, RNASE7, DAD1, JAG2, KIFC3, SMPD3, and PLCD3, by sequencing the obtained RNA molecules;

(c) predicting that the human subject with psoriasis will be responsive to the IL-23 inhibitor based on the expression levels in (b); and (d) based on (c), administering the IL-23 inhibitor to the human subject.

2. The method of claim 1, wherein a positive predictive value (PPV) of the method is greater than 90%.

3. The method of claim 1, wherein a positive predictive value (PPV) of the method is greater than 95%.

4. The method of claim 1, wherein a negative predictive value (NPV) of the method is greater than 50%.

5. The method of claim 1, wherein the human subject with psoriasis has a Psoriasis Area and Severity Index (PASI) score of at least 5.

6. The method of claim 5, wherein the PASI score decreases by at least 75% after treating with the IL-23 inhibitor.

7. The method of claim 1, wherein the IL-23 inhibitor is a biologic.

8. The method of claim 1, wherein the IL-23 inhibitor comprises an antibody.

9. The method of claim 1, wherein the IL-23 inhibitor is at least one drug selected from the group consisting of tildrakizumab, guselkumab, ustekinumab, and risankizumab.

10. The method of claim 1, wherein the IL-23 inhibitor is at least one drug selected from the group consisting of tildrakizumab, guselkumab, and risankizumab.

11. The method of claim 1, wherein the IL-23 inhibitor is at least one drug selected from the group consisting of tildrakizumab and guselkumab.

12. The method of claim 1, wherein the RNA molecules are mRNA molecules.

13. The method of claim 1, wherein (c) comprises applying a trained algorithm to the expression levels in (b) to predict that the human subject with psoriasis will be responsive to the IL-23 inhibitor, wherein an algorithm is trained using transcriptome profiles of responders and non-responders to the IL-23 inhibitor to provide the trained algorithm.

14. The method of claim 1, wherein a nucleic acids probe of the one or more nucleic acids probes comprises a homopolymeric sequence.

15. The method of claim 14, wherein the homopolymeric sequence comprises thymine or uracil.

16. The method of claim 14, wherein the homopolymeric sequence comprises two or more consecutive thymine residues.

17. The method of claim 14, wherein the homopolymeric sequence comprises at least 10 consecutive thymine residues.

18. The method of claim 14, wherein the homopolymeric sequence comprises at least 20 consecutive thymine residues.

19. The method of claim 12, wherein the one or more nucleic acids probes bind to poly-A tails of the mRNA molecules.

* * * * *